US012655185B2

(12) United States Patent
Bhandari et al.

(10) Patent No.: US 12,655,185 B2
(45) Date of Patent: Jun. 16, 2026

(54) PEPTIDE INHIBITORS OF INTERLEUKIN-23 AND THEIR USE TO TREAT INFLAMMATORY DISEASES

(71) Applicant: Protagonist Therapeutics, Inc., Newark, CA (US)

(72) Inventors: Ashok Bhandari, Pleasanton, CA (US); Xiaoli Cheng, Mountain View, CA (US); Larry C. Mattheakis, Cupertino, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 1329 days.

(21) Appl. No.: 16/319,958

(22) PCT Filed: Jul. 27, 2017

(86) PCT No.: PCT/US2017/044249

§ 371 (c)(1),
(2) Date: Jan. 23, 2019

(87) PCT Pub. No.: WO2018/022937

PCT Pub. Date: Feb. 1, 2018

(65) Prior Publication Data

US 2019/0270786 A1 Sep. 5, 2019

Related U.S. Application Data

(60) Provisional application No. 62/367,549, filed on Jul. 27, 2016.

(51) Int. Cl.

| | |
|---|---|
| ***C07K 14/54*** | (2006.01) |
| ***A61K 9/00*** | (2006.01) |
| ***A61K 38/00*** | (2006.01) |
| ***A61K 38/16*** | (2006.01) |
| ***A61K 47/60*** | (2017.01) |
| ***A61P 1/00*** | (2006.01) |
| ***A61P 17/06*** | (2006.01) |
| ***C07K 14/00*** | (2006.01) |
| ***C07K 19/00*** | (2006.01) |

(52) U.S. Cl.

CPC ............ *C07K 14/54* (2013.01); *A61K 9/0019* (2013.01); *A61K 9/0053* (2013.01); *A61K 38/16* (2013.01); *A61K 47/60* (2017.08); *A61P 1/00* (2018.01); *A61P 17/06* (2018.01); *C07K 14/00* (2013.01); *C07K 19/00* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 4,684,620 | A | 8/1987 | Hruby et al. |
| 4,724,229 | A | 2/1988 | Ali |
| 5,192,746 | A | 3/1993 | Lobl et al. |
| 5,293,050 | A | 3/1994 | Chapple-sokol et al. |
| 5,354,707 | A | 10/1994 | Chapple-sokol et al. |
| 5,494,897 | A | 2/1996 | Shikawa et al. |
| 5,569,741 | A | 10/1996 | Coy et al. |
| 5,990,084 | A | 11/1999 | Richter et al. |
| 6,087,334 | A | 7/2000 | Beeley et al. |
| 6,235,711 | B1 | 5/2001 | Dutta |
| 6,818,617 | B1 | 11/2004 | Niewiarowski |
| 7,534,764 | B2 | 5/2009 | Ganz et al. |
| 7,589,170 | B1 | 9/2009 | Smythe et al. |
| 7,718,598 | B1 | 5/2010 | Smythe et al. |
| 8,313,950 | B2 | 11/2012 | Rovin et al. |
| 8,435,941 | B2 | 5/2013 | Ganz et al. |
| 8,536,140 | B2 | 9/2013 | Clandinin et al. |
| 8,568,706 | B2 | 10/2013 | Grabstein et al. |
| 8,796,418 | B2 | 8/2014 | Walensky et al. |
| 8,946,150 | B2 | 2/2015 | Gallagher et al. |
| 8,999,935 | B2 | 4/2015 | Huang |
| 9,169,292 | B2 | 10/2015 | Gallagher et al. |
| 9,273,093 | B2 | 3/2016 | Bhandari et al. |
| 9,518,091 | B2 | 12/2016 | Bhandari et al. |
| 9,624,268 | B2 | 4/2017 | Bourne et al. |
| 9,714,270 | B2 | 7/2017 | Bhandari et al. |
| 9,809,623 | B2 | 11/2017 | Bhandari et al. |
| 9,822,157 | B2 | 11/2017 | Smythe et al. |
| 10,023,614 | B2 | 7/2018 | Bhandari et al. |
| 10,030,061 | B2 | 7/2018 | Smythe et al. |
| 10,035,824 | B2 | 7/2018 | Bhandari et al. |
| 10,059,744 | B2 | 8/2018 | Bhandari et al. |

(Continued)

FOREIGN PATENT DOCUMENTS

| | | | |
|---|---|---|---|
| CA | 2015761 | A1 | 11/1990 |
| CL | 2018000128 | A1 | 6/2018 |

(Continued)

OTHER PUBLICATIONS

Araghi et al. Designing helical peptide inhibitors of protein-protein Interactions. Current Opinion in Structural Biology 2016, 39:27-38.*
Webster et al. Engineered Two-Helix Small Proteins for Molecular Recognition. ChemBioChem 2009, 10, 1293-1296.*
Chang, et al., Role of disulfide bonds in the structure and activity of human insulin. Mol Cells (Dec. 2003); 16(3): 323-330.
Clark, et al., "The Engineering of an Orally Active Conotoxin for the Treatment of Neuropathic Pain." Angew Chem Int Ed (Sep. 2010); 49: 6545-6548.

(Continued)

*Primary Examiner* — Christopher M Babic
*Assistant Examiner* — Kimberly A Aron
(74) *Attorney, Agent, or Firm* — Cooley LLP

(57) ABSTRACT

The present invention provides novel peptide inhibitors of interleukin-23, and related methods of using these peptide inhibitors to treat or prevent a variety of diseases and disorders, including inflammatory bowel disease, Crohn's disease and psoriasis.

6 Claims, No Drawings

Specification includes a Sequence Listing.

(56) References Cited

U.S. PATENT DOCUMENTS

| | | | |
|---|---|---|---|
| 10,196,424 | B2 | 2/2019 | Bourne et al. |
| 10,278,957 | B2 | 5/2019 | Anandan et al. |
| 10,301,371 | B2 | 5/2019 | Bhandari et al. |
| 10,407,468 | B2 | 9/2019 | Bhandari et al. |
| 10,442,846 | B2 | 10/2019 | Smythe et al. |
| 10,501,515 | B2 | 12/2019 | Smythe et al. |
| 10,626,146 | B2 | 4/2020 | Bhandari et al. |
| 10,729,676 | B2 | 8/2020 | Anandan et al. |
| 10,787,490 | B2 | 9/2020 | Bhandari et al. |
| 10,941,183 | B2 | 3/2021 | Bhandari et al. |
| 11,041,000 | B2 | 6/2021 | Bhandari et al. |
| 11,111,272 | B2 | 9/2021 | Bhandari et al. |
| 2003/0166138 | A1 | 9/2003 | Kinsella et al. |
| 2003/0166514 | A1 | 9/2003 | Jones et al. |
| 2004/0052785 | A1 | 3/2004 | Goodman et al. |
| 2004/0123343 | A1 | 6/2004 | La Rosa et al. |
| 2004/0176293 | A1 | 9/2004 | Peterson et al. |
| 2006/0008848 | A1 | 1/2006 | Verdine et al. |
| 2006/0166881 | A1 | 7/2006 | Hotchkiss et al. |
| 2006/0183884 | A1 | 8/2006 | Blaschuk et al. |
| 2007/0032417 | A1 | 2/2007 | Baell |
| 2007/0166308 | A1 | 7/2007 | Pullen et al. |
| 2007/0191272 | A1 | 8/2007 | Stemmer et al. |
| 2007/0197430 | A1 | 8/2007 | Baell et al. |
| 2008/0019913 | A1 | 1/2008 | Polt et al. |
| 2008/0213277 | A1 | 9/2008 | Sasu et al. |
| 2008/0260820 | A1 | 10/2008 | Borrelly et al. |
| 2008/0300180 | A1 | 12/2008 | Schambye et al. |
| 2009/0053819 | A1 | 2/2009 | Seymour et al. |
| 2009/0170143 | A1 | 7/2009 | Uttenthal et al. |
| 2009/0257952 | A1 | 10/2009 | Cochran et al. |
| 2009/0325810 | A1 | 12/2009 | Lapointe et al. |
| 2010/0151487 | A1 | 6/2010 | Rovin et al. |
| 2010/0183617 | A1 | 7/2010 | Herr et al. |
| 2010/0190710 | A1 | 7/2010 | Chemtob et al. |
| 2010/0196441 | A1 | 8/2010 | Sondermeijer et al. |
| 2010/0272731 | A1 | 10/2010 | Presta et al. |
| 2010/0280098 | A1 | 11/2010 | Juliano et al. |
| 2011/0059087 | A1 | 3/2011 | Lewis et al. |
| 2011/0086024 | A1 | 4/2011 | Arthos et al. |
| 2011/0118186 | A1 | 5/2011 | Schteingart et al. |
| 2011/0142889 | A1 | 6/2011 | Lee et al. |
| 2011/0212104 | A1 | 9/2011 | Beaumont et al. |
| 2011/0282029 | A1 | 11/2011 | Holmes et al. |
| 2012/0021975 | A1 | 1/2012 | Hoffman et al. |
| 2012/0040894 | A1 | 2/2012 | Ganz et al. |
| 2012/0071422 | A1 | 3/2012 | Gallagher et al. |
| 2012/0115930 | A1 | 5/2012 | Monia et al. |
| 2013/0029907 | A1 | 1/2013 | Gallagher et al. |
| 2013/0137123 | A1 | 5/2013 | Cucchiara et al. |
| 2013/0172272 | A1 | 7/2013 | Gallagher et al. |
| 2013/0183755 | A1 | 7/2013 | Gallagher et al. |
| 2013/0310303 | A1 | 11/2013 | Eldar-Finkelman et al. |
| 2013/0338132 | A1 | 12/2013 | Koshiba et al. |
| 2014/0005128 | A1 | 1/2014 | Mo et al. |
| 2014/0193465 | A1 | 7/2014 | Bhandari et al. |
| 2014/0286953 | A1 | 9/2014 | Sasu et al. |
| 2014/0294901 | A1 | 10/2014 | Bhandari et al. |
| 2014/0294902 | A1 | 10/2014 | Bhandari et al. |
| 2014/0336110 | A1 | 11/2014 | Ganz et al. |
| 2015/0056301 | A1 | 2/2015 | Kawabe et al. |
| 2015/0118315 | A1 | 4/2015 | Wilson |
| 2015/0157692 | A1 | 6/2015 | Fu |
| 2015/0203555 | A1* | 7/2015 | Gellman ................ C07K 14/52 424/85.1 |
| 2015/0284429 | A1 | 10/2015 | Merutka |
| 2016/0031944 | A1 | 2/2016 | Bhandari et al. |
| 2016/0039878 | A1 | 2/2016 | Gallagher et al. |
| 2016/0145306 | A1 | 5/2016 | Bourne et al. |
| 2016/0152664 | A1 | 6/2016 | Bhandari et al. |
| 2016/0159862 | A1 | 6/2016 | Bhandari et al. |
| 2016/0199437 | A1 | 7/2016 | Wilson |
| 2016/0222076 | A1 | 8/2016 | Smythe et al. |
| 2016/0228491 | A1 | 8/2016 | Wilson |
| 2016/0368966 | A1 | 12/2016 | Bhandari et al. |
| 2017/0313754 | A1 | 11/2017 | Bourne et al. |
| 2017/0327541 | A1 | 11/2017 | Bhandari et al. |
| 2018/0022778 | A1 | 1/2018 | Bourne et al. |
| 2018/0079782 | A1 | 3/2018 | Bhandari et al. |
| 2018/0079783 | A1 | 3/2018 | Bhandari et al. |
| 2018/0099995 | A1 | 4/2018 | Bhandari et al. |
| 2018/0100004 | A1 | 4/2018 | Smythe et al. |
| 2018/0105572 | A1 | 4/2018 | Bhandari et al. |
| 2018/0148477 | A1 | 5/2018 | Bhandari et al. |
| 2019/0002500 | A1 | 1/2019 | Bhandari et al. |
| 2019/0002503 | A1 | 1/2019 | Bourne et al. |
| 2019/0016756 | A1 | 1/2019 | Bhandari et al. |
| 2019/0076400 | A1 | 3/2019 | Anandan et al. |
| 2019/0185535 | A1 | 6/2019 | Smythe et al. |
| 2019/0185536 | A1 | 6/2019 | Smythe et al. |
| 2019/0231746 | A1 | 8/2019 | Anandan et al. |
| 2019/0248870 | A1 | 8/2019 | Bhandari et al. |
| 2019/0264197 | A1 | 8/2019 | Barkan et al. |
| 2019/0300590 | A1 | 10/2019 | Bhandari et al. |
| 2019/0337983 | A1 | 11/2019 | Bhandari et al. |
| 2020/0017549 | A1 | 1/2020 | Bhandari et al. |
| 2020/0017566 | A1 | 1/2020 | Bourne et al. |
| 2020/0040037 | A1 | 2/2020 | Bhandari et al. |
| 2020/0064357 | A1 | 2/2020 | Cheng et al. |
| 2020/0207822 | A1 | 7/2020 | Bhandari et al. |
| 2020/0239516 | A1 | 7/2020 | Richelle et al. |
| 2020/0239523 | A1 | 7/2020 | Bhandari et al. |
| 2020/0361992 | A1 | 11/2020 | Bourne et al. |
| 2021/0061872 | A1 | 3/2021 | Liu et al. |
| 2021/0147483 | A1 | 5/2021 | Bourne et al. |
| 2021/0261622 | A1 | 8/2021 | Sun et al. |
| 2021/0363185 | A1 | 11/2021 | Bhandari et al. |
| 2021/0371466 | A1 | 12/2021 | Bhandari et al. |
| 2022/0041658 | A1 | 2/2022 | Bhandari et al. |

FOREIGN PATENT DOCUMENTS

| | | | |
|---|---|---|---|
| CL | 2018003322 | A1 | 1/2019 |
| CN | 101307085 | A | 11/2008 |
| CN | 101358201 | A | 2/2009 |
| DE | 10107707 | A1 | 8/2002 |
| EP | 0396526 | A2 | 11/1990 |
| JP | 2010-517529 | A | 5/2010 |
| JP | 2010-536364 | A | 12/2010 |
| JP | 2011-231085 | A | 11/2011 |
| JP | 2012-525124 | A | 10/2012 |
| JP | 2016-521257 | A | 7/2016 |
| JP | 2017530090 | A | 10/2017 |
| WO | WO 1992/017492 | A1 | 10/1992 |
| WO | WO-9411018 | A1 | 5/1994 |
| WO | WO-9617617 | A1 | 6/1996 |
| WO | WO 1997/007129 | A1 | 2/1997 |
| WO | WO 1997/025351 | A2 | 7/1997 |
| WO | WO 1998/008871 | A1 | 3/1998 |
| WO | WO 2000/055184 | A1 | 3/1998 |
| WO | WO-9833524 | A1 | 8/1998 |
| WO | WO 1999/002194 | A1 | 1/1999 |
| WO | WO 1999/026615 | A1 | 6/1999 |
| WO | WO 2000/006243 | A2 | 2/2000 |
| WO | WO 2000/009560 | A1 | 2/2000 |
| WO | WO 2000/018789 | A1 | 4/2000 |
| WO | WO 2000/018790 | A1 | 4/2000 |
| WO | WO 2000/023474 | A1 | 4/2000 |
| WO | WO 2000/055119 | A1 | 9/2000 |
| WO | WO 2000/061580 | A1 | 10/2000 |
| WO | WO 2001/068586 | A2 | 9/2001 |
| WO | WO 2003/066678 | A1 | 8/2003 |
| WO | WO 2004/011650 | A2 | 2/2004 |
| WO | WO 2004/092405 | A2 | 10/2004 |
| WO | WO 2006/032104 | A1 | 3/2006 |
| WO | WO-2007076524 | A2 | 7/2007 |
| WO | WO 2007/138291 | A2 | 12/2007 |
| WO | WO 2008/097461 | A2 | 8/2008 |
| WO | WO-2008101017 | A2 | 8/2008 |
| WO | WO 2008/134659 | A2 | 11/2008 |
| WO | WO 2008/140602 | A2 | 11/2008 |
| WO | WO 2009/002947 | A2 | 12/2008 |
| WO | WO 2009/027752 | A2 | 3/2009 |
| WO | WO-2010017598 | A1 | 2/2010 |

(56) References Cited

FOREIGN PATENT DOCUMENTS

| | | | |
|---|---|---|---|
| WO | WO 2010/065815 | A2 | 6/2010 |
| WO | WO 2010/116752 | A1 | 10/2010 |
| WO | WO 2010/124874 | A1 | 11/2010 |
| WO | WO 2011/091357 | A1 | 7/2011 |
| WO | WO 2011/149942 | A2 | 12/2011 |
| WO | WO 2012/052205 | A1 | 4/2012 |
| WO | WO 2013/086143 | A1 | 6/2013 |
| WO | WO 2014/059213 | A1 | 4/2014 |
| WO | WO 2014/127316 | A2 | 8/2014 |
| WO | WO 2014/145561 | A2 | 9/2014 |
| WO | WO 2014/165448 | A1 | 10/2014 |
| WO | WO 2014/165449 | A1 | 10/2014 |
| WO | WO 2014/210056 | A1 | 12/2014 |
| WO | WO 2015/054500 | A2 | 4/2015 |
| WO | WO 2015/157283 | A9 | 10/2015 |
| WO | WO 2015/176035 | A1 | 11/2015 |
| WO | WO 2015/183963 | A2 | 12/2015 |
| WO | WO 2015/200916 | A2 | 12/2015 |
| WO | WO 2016/004093 | A2 | 1/2016 |
| WO | WO 2016/011208 | A1 | 1/2016 |
| WO | WO 2016/054411 | A1 | 4/2016 |
| WO | WO 2016/054445 | A1 | 4/2016 |
| WO | WO 2016/109363 | A1 | 7/2016 |
| WO | WO 2016/115168 | A1 | 7/2016 |
| WO | WO 2016/195663 | A1 | 12/2016 |
| WO | WO 2016/200364 | A1 | 12/2016 |
| WO | WO 2017/011820 | A2 | 1/2017 |
| WO | WO 2017/117411 | A1 | 7/2017 |
| WO | WO 2017/165676 | A1 | 9/2017 |
| WO | WO 2018/022937 | A1 | 2/2018 |
| WO | WO-2018022917 | A1 | 2/2018 |
| WO | WO 2018/089693 | A2 | 5/2018 |
| WO | WO 2018/136646 | A1 | 7/2018 |
| WO | WO-2019051494 | A1 | 3/2019 |
| WO | WO 2019/157268 | A1 | 8/2019 |
| WO | WO 2019/246273 | A1 | 12/2019 |
| WO | WO-2019246349 | A1 | 12/2019 |
| WO | WO 2020/014646 | A1 | 1/2020 |
| WO | WO-2020198682 | A1 | 10/2020 |
| WO | WO 2021/007433 | A1 | 1/2021 |
| WO | WO-2021046246 | A1 | 3/2021 |
| WO | WO-2021142373 | A1 | 7/2021 |
| WO | WO-2021146441 | A1 | 7/2021 |
| WO | WO-2021146454 | A1 | 7/2021 |
| WO | WO-2021146458 | A1 | 7/2021 |
| WO | WO-2022026629 | A1 | 2/2022 |
| WO | WO-2022026631 | A1 | 2/2022 |
| WO | WO-2022026633 | A1 | 2/2022 |
| WO | WO-2022109328 | A1 | 5/2022 |
| WO | WO-2022212696 | A1 | 10/2022 |
| WO | WO-2022212698 | A1 | 10/2022 |
| WO | WO-2022212700 | A2 | 10/2022 |
| WO | WO-2022266060 | A1 | 12/2022 |
| WO | WO-2023288017 | A2 | 1/2023 |
| WO | WO-2023288019 | A2 | 1/2023 |
| WO | WO-2023288028 | A2 | 1/2023 |
| WO | WO-2023009891 | A2 | 2/2023 |
| WO | WO-2023150618 | A2 | 8/2023 |
| WO | WO-2023150630 | A2 | 8/2023 |
| WO | WO-2023240077 | A1 | 12/2023 |
| WO | WO-2024011188 | A1 | 1/2024 |
| WO | WO-2024110477 | A2 | 5/2024 |
| WO | WO-2025207760 | A1 | 10/2025 |

OTHER PUBLICATIONS

Craik, et al., "Potential therapeutic applications of the cyclotides and related cystine knot mini-proteins." Expert Opin Investig Drugs (May 2007); 16(5): 595-604.

De Vega, et al., "Modulation of Protein-Protein Interactions by Stabilizing/Mimicking Protein Secondary Structure Elements." Curr Top Med Chem (2007); 7(1): 33-62.

Dutton, et al., "A New Level of Conotoxin Diversity, a Non-native Disulfide Bond Connectivity in—Conotoxin AuIB Reduces Structural Definition but Increases Biological Activity." J Biol Chem (Oct. 2002); 277(50): 48849-48857.

Fass, D., "Disulfide bonding in protein biophysics." Annu Rev Biophys (2012); 41: 63-79. Epub Dec. 20, 2011.

Fosgerau and Hoffman, "Peptide therapeutics: current status and future directions." Drug Discovery Today (2015); 20(1): 122-128.

Foster "Deuterium Isotope Effects in Studies of Drug Metabolism", Trends Pharmacol. Sci. (1984); 5(12): 524-527.

Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-18, 19 pages.

Garcia, Josep et al., "D-Polyarginine Lipopeptides as Intestinal Permeation Enhancers". ChemMedChem Oct. 8, 2018; 13(19): 2045-2052. Epub Aug. 20, 2018.

Gombotz and Pettit, "Biodegradable Polymers for Protein and Peptide Drug Delivery". Bioconjugate Chem. (Jul. 1, 1995); 6(4): 332-351.

Gruschow, et al., "New pacidamycin antibiotics through precursor-directed biosynthesis". Chembiochem. Jan. 26, 2009; 10(2): 355-360.

Guerler and Knapp, "Novel protein folds and their nonsequential structural analogs." Protein Sci (Aug. 2008); 17(8): 1374-1382.

Guharoy and Chakrabarti, "Secondary structure based analysis and classification of biological interfaces: identification of binding motifs in protein-protein interactions." Bioinformatics (2007); 23(15): 1909-1918. Epub May 17, 2007.

Gupta, et al., "A classification of disulfide patterns and its relationship to protein structure and function." Protein Sci (Aug. 2004); 13(8): 2045-2058.

Hartig, et al., "Intramolecular disulphide bond arrangements in nonhomologous proteins." Protein Sci Publ Protein Soc (Feb. 2005); 14(2): 474-482.

Henikoff and Henikoff, "Amino acid substitution matrices from protein blocks." Proc Natl Acad Sci U S A (Nov. 1992); 89(Nov.); 10915-10919.

Liu, Shuang, "Radiolabeled Multimeric Cyclic Rgd Peptides as Integrin Alphavbeta3 Targeted Radiotracers For Tumor Imaging" School of Health Science, Purdue University, Molecular Pharmaceuticals (2006); 3(5):472-487.

Maher, Sam et al., "Safety and efficacy of sodium caprate in promoting oral drug absorption: from in vitro to the clinic". Advanced Drug Delivery Reviews Dec. 17, 2009; 61 (15): 1427-1449. Epub Oct. 1, 2009.

Maher, Sam et al., "Application of Permeation Enhancers in Oral Delivery of Macromolecules: An Update". Pharmaceutics Jan. 19, 2019; 11(1): 41, 23 pages.

Muheem, Abdul et al., "A review on the strategies for oral delivery of proteins and peptides and their clinical perspectives". Saudi Pharmaceutical Journal Jul. 2016; 24(4):413-428. Epub Jun. 16, 2014.

Rubinstein and Niv, "Peptidic modulators of protein-protein interactions: Progress and challenges in computational design." Biopolymers (2009); 91(7): 505-513.

Tsukada, et al., "An Anti-α-Fetoprotein Antibody-Daunorubicin Conjugate With a Novel Poly-L-glutamic Acid Derivative as Intermediate Drug Carrier ". J. Natl. Cancer Inst. (Sep. 1984); 73(3): 721-729.

White and Yudin, "Contemporary strategies for peptide macrocyclization." Nat Chem (Jun. 2011); 3(7): 509-524.

U.S. Appl. No. 14/714,198, filed May 15, 2015, Bhandari, et al.

U.S. Appl. No. 14/775,469, filed Mar. 17, 2014, Smythe, et al.

U.S. Appl. No. 14/800,627, filed Jul. 15, 2015, Bourne, et al.

U.S. Appl. No. 14/872,975, filed Oct. 1, 2015, Bhandari, et al.

U.S. Appl. No. 15/000,923, filed Jan. 19, 2016, Bhandari, et al.

U.S. Appl. No. 15/046,325, filed Feb. 17, 2016, Bhandari, et al.

U.S. Appl. No. 15/255,750, filed Sep. 2, 2016, Bhandari, et al.

U.S. Appl. No. 15/258,540, filed Sep. 7, 2016, Bhandari, et al.

U.S. Appl. No. 15/321,124, filed Dec. 21, 2016, Bourne, et al.

U.S. Appl. No. 15/442,229, filed Feb. 24, 2017, Bourne, et al.

U.S. Appl. No. 15/467,810, filed Mar. 23, 2017, Bhandari, et al.

U.S. Appl. No. 15/514,983, filed Mar. 28, 2017, Bhandari, et al.

U.S. Appl. No. 15/614,047, filed Jun. 5, 2017, Bhandari, et al.

(56) References Cited

OTHER PUBLICATIONS

U.S. Appl. No. 15/698,407, filed Sep. 7, 2017, Bhandari, et al.
U.S. Appl. No. 15/720,333, filed Sep. 29, 2017, Smythe, et al.
U.S. Appl. No. 15/828,214, filed Nov. 30, 2017, Smythe, et al.
U.S. Appl. No. 15/831,087, filed Dec. 4, 2017, Bhandari, et al.
U.S. Appl. No. 15/831,099, filed Dec. 4, 2017, Bhandari, et al.
U.S. Appl. No. 15/831,100, filed Dec. 4, 2017, Bhandari, et al.
U.S. Appl. No. 15/831,120, filed Dec. 4, 2017, Bhandari, et al.
U.S. Appl. No. 15/836,648, filed Dec. 8, 2017, Bhandari, et al.
U.S. Appl. No. 16/035,060, filed Jul. 13, 2018, Bhandari, et al.
U.S. Appl. No. 16/037,982, filed Jul. 17, 2018, Smythe, et al.
U.S. Appl. No. 16/039,813, filed Jul. 19, 2018, Bhandari, et al.
U.S. Appl. No. 16/113,072, filed Aug. 27, 2018, Bhandari, et al.
U.S. Appl. No. 16/128,352, filed Sep. 11, 2018, Anandan, et al.
U.S. Appl. No. 16/217,864, filed Dec. 12, 2018, Bourne, et al.
U.S. Appl. No. 16/282,908, filed Feb. 22, 2019, Bhandari, et al.
U.S. Appl. No. 16/417,075, filed May 20, 2019, Bhandari, et al.
U.S. Appl. No. 16/510,118, filed Jul. 12, 2019, Bhandari, et al.
U.S. Appl. No. 16/774,686, filed Jan. 28, 2020, Bhandari, et al.
U.S. Appl. No. 16/780,297, filed Feb. 3, 2020, Bhandari, et al.
U.S. Appl. No. 16/781,516 filed Filed Feb. 4, 2020, Bhandari, et al..
U.S. Appl. No. 16/839,368, filed Apr. 3, 2020, Smythe, et al.
U.S. Appl. No. 16/856,521, filed Apr. 23, 2020, Bhandari, et al.
U.S. Appl. No. 16/931,046, filed Jul. 16, 2020, Bhandari, et al.
U.S. Appl. No. 16/940,989, filed Jul. 28, 2020, Bhandari, et al.
U.S. Appl. No. 16/964,708, filed Jul. 24, 2020, Bourne, et al.
U.S. Appl. No. 17/001,428, filed Aug. 24, 2020, Bhandari, et al.
U.S. Appl. No. 17/011,844, filed Sep. 3, 2020, Liu, et al.
U.S. Appl. No. 17/061,336, filed Oct. 1, 2020, Bourne, et al.
U.S. Appl. No. 17/084,225, filed Oct. 29, 2020, Bourne, et al.
U.S. Appl. No. 17/099,308, filed Nov. 16, 2020, Smythe, et al.
U.S. Appl. No. 17/104,596, filed Nov. 25, 2020, Bhandari, et al.
U.S. Appl. No. 17/137,049, filed Dec. 29, 2020, Bhandari, et al.
U.S. Appl. No. 17/149,509, filed Jan. 14, 2021, Sun, et al.
U.S. Appl. No. 17/149,544, filed Jan. 14, 2021, Sun, et al.
U.S. Appl. No. 17/161,370, filed Jan. 28, 2021, Bhandari, et al.
Brayden, D.J., and Mrsny, R.J., "Oral peptide delivery: prioritizing the leading technologies". Therapeutic Delivery (2011); 2(12): 1567-1573.
Cherry, et al., "Vedolizumab: an a437 integrin antagonist for ulcerative colitis and Crohn's disease." Ther Adv Chronic Dis. (2015); 6(5): 224-233.
European Application No. 18741939.5, Partial Supplementary European Search Report dated Aug. 26, 2020, 13 pages.
European Application No. 18741939.5, Extended European Search Report dated Nov. 27, 2020, 11 pages.
European Application No. 17771175.1, Partial Supplementary European Search Report dated Nov. 25, 2019, 15 pages.
European Application No. 17771175.1, Extended European Search Report dated Mar. 4, 2020, 11 pages.
Gentilucci, et al., "Chemical Modifications Designed to Improve Peptide Stability: Incorporation of Non-Natural Amino Acids, Pseudo-Peptide Bonds, and Cyclization". Curr Pharm Des. (2010); 16(28): 3185-3203.
Görmer, et al., "Efficient Microwave-Assisted Synthesis of Unsymmetrical Disulfides", J. Org. Chem. (Feb. 1, 2010); 75(5): 1811-1813.
Kuchař, et al., "Human interleukin-23 receptor antagonists derived from an albumin-binding domain scaffold inhibit IL-23-dependent ex vivo expansion of IL-17-producing T-cells". Proteins (Jun. 2014); 82(6): 975-989. Epub Nov. 23, 2013.
Makharia, Govind K., "Current and emerging therapy for celiac disease", Frontiers in Medicine (Mar. 2014); vol. 1, Article 6, pp. 1-11.
PCT/US2017/023859, Invitation to Pay Additional Fees, mailed May 25, 2017, 9 pages.
PCT/US2017/023859, International Preliminary Report on Patentability, dated Sep. 25, 2018, 9 pages.
PCT/US2017/023859, International Search Report and Written Opinion, mailed Jul. 26, 2017, 14 pages.
PCT/US2017/060944, International Preliminary Report on Patentability dated May 21, 2019, 8 pages.
PCT/US2017/060944, International Search Report and Written Opinion mailed Feb. 2, 2020, 10 pages.
PCT/US2018/050480, International Preliminary Report on Patentability dated Mar. 17, 2020, 7 pages.
PCT/US2019/017192, International Search Report and Written Opinion, mailed Jun. 11, 2019, 13 pages.
PCT/US2019/041665, International Preliminary Report on Patentability, mailed Jan. 12, 2021, 7 pages.
PCT/US2020/041409, International Search Report and Written Opinion, mailed Dec. 3, 2020, 17 pages.
PCT/US2020/041409, Invitation to pay additional search fees, mailed Sep. 28, 2020, 2 pages.
Quiniou, et al., "Specific targeting of the IL-23 receptor, using a novel small peptide noncompetitive antagonist, decreases the inflammatory response". Am J Physiol Regul Integr Comp Physiol. (Nov. 15, 2014); 307(10): R1216-R1230. Epub Aug. 20, 2014.
U.S. Appl. No. 15/467,810, Notice of Allowability dated Mar. 13, 2019, 8 pages.
U.S. Appl. No. 16/067,568, Office Action mailed Apr. 2, 2020, 15 pages.
U.S. Appl. No. 16/478,733, Office Action mailed Sep. 9, 2020, 24 pages.
U.S. Appl. No. 16/510,118, Office Action mailed Sep. 4, 2020, 16 pages.
U.S. Appl. No. 17/001,428, Notice of Allowance mailed Feb. 10, 2021, 9 pages.
Chermahini et al., "Cyclic peptide nanocapsule as ion carrier for halides: a theoretical survey." Structural Chemistry (Oct. 2018); 29(5): 1351-1357.
Dyson, G., et al., "May's Chemistry of Synthetic Drugs." Fifth Edition, Longmans, London (1959); pp. 12-19.
Kong et al., "De novo development of proteolytically resistant therapeutic peptides for oral administration." Nat Biomed Eng. May 2020; 4(5): 560-571. doi: 10.1038/s41551-020-0556-3. Epub May 11, 2020.
Qi, Y., et al., "A Diaminodiacid (DADA) Strategy for the Development of Disulfide Surrogate Peptides." Chem Asian J. Sep. 15, 2020; 15(18): 2793-2802. doi: 10.1002/asia.202000609. Epub Aug. 11, 2020.
Sawyer, T.K., et al., "Macrocyclic a helical peptide therapeutic modality: A perspective of learnings and challenges." Bioorg Med Chem. Jun. 1, 2018; 26(10): 2807-2815. doi: 10.1016/j.bmc.2018.03.008. Epub Mar. 16, 2018.
Annis, et al., "[10] Disulfide bond formation in peptides". Methods Enzymol. (1997); 289: 198-221.
Cheng et al., "The Biomarker Profile of PTG-200, an Oral Peptide Antagonist of IL-23 Receptor, Tracks with Efficacy in a Preclinical Model of IBD". Gastroenterology, AGA Abstracts, vol. 152, Issue 5, Supplement 1, S31, Apr. 1, 2017.
Delgado et al., "The uses and properties of PEG-linked proteins". Critical Reviews in Therapeutic Drug Carrier Systems (Jan. 1, 1992); 9(3-4): 249-304.
Hruby, et al., "Recent Developments in the Design of Receptor Specific Opioid Peptides." Medicinal Research Reviews (1989); 9(3): 343-401.
Hu, et al., "Synthesis and biological evaluations of novel endomorphin analogues containing α-hydroxy-β-phenylalanine (AHPBA) displaying mixed μ/δopioid receptor agonist and δ opioid receptor antagonist activities". European Journal of Medicinal Chemistry (Mar. 6, 2015); 92: 270-281. Epub Dec. 29, 2014.
Hudecz, et al., "Synthesis, conformation, biodistribution and in vitro cytotoxicity of daunomycin-branched polypeptide conjugates". Bioconjugate Chem. (Jan. 1, 1992); 3(1): 49-57.
Liu and Wang, "Endomorphins: potential roles and therapeutic indications in the development of opioid peptide analgesic drugs". Med Res Rev. (May 2012); 32(3): 536-580. Epub Feb. 1, 2011.
Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.

(56) References Cited

OTHER PUBLICATIONS

Longobardo, et al., "Incorporation of ß-amino acids in bioactive peptides: a β- casomorphin case study." Peptides 2002, Abstract P A97, Proceedings of the European Peptide Symposium, 27th, Sorrento, Italy, Aug. 31-Sep. 6, 2002 (2002), 198-199.
Maeda, et al., "Conjugates of anticancer agents and polymers: advantages of macromolecular therapeutics in vivo". Bioconjugate Chem. (Sep./Oct. 1992); 3(5): 351-362.
U.S. Appl. No. 17/149,544 entitled "Peptide inhibitors of INTERLEUKIN-23 receptor and their use to treat inflammatory diseases" filed Jan. 14, 2021, 174 pages.
Witt, Dariusz, "Recent developments in disulfide bond formation". Synthesis (2008); 16: 2491-2509.
Zalipsky, Samuel, "Functionalized Poly(ethylene glycols) for Preparation of Biologically Relevant Conjugates". Bioconjugate Chem. (1995); 6(2): 150-165.
U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/745,371, filed Jan. 16, 2018, Bhandari, et al.
U.S. Appl. No. 16/282,920, filed Feb. 22, 2019, Bhandari, et al.
U.S. Appl. No. 16/348,293, filed May 8, 2019, Cheng, et al.
U.S. Appl. No. 16/376,565, filed Apr. 5, 2019, Bhandari, et al.
U.S. Appl. No. 16/382,783, filed Apr. 12, 2019, Bhandari, et al.
U.S. Appl. No. 16/439,435, filed Jun. 12, 2019, Bourne, et al.
U.S. Appl. No. 16/478,733, filed Jul. 29, 2019, Bhandari, et al.
U.S. Appl. No. 16/553,486, filed Aug. 28, 2019, Smythe, et al.
U.S. Appl. No. 16/656,339, filed Oct. 17, 2019, Bhandari, et al.
U.S. Appl. No. 16/689,884, filed Nov. 20, 2019, Bhandari, et al.
U.S. Appl. No. 16/700,659, filed Dec. 2, 2019, Bhandari, et al.
Adams and Macmillan, "Investigation of peptide thioester formation via N→Se acyl transfer." Journal of Peptide Science (2013); 19 (2): 65-73.
Andreu, et al., "Formation of Disulfide Bonds in Synthetic Peptides and Proteins" in Synthetic Peptides and Proteins. In: Pennington M.W., Dunn B.M. (eds) Peptide Synthesis Protocols. Methods in Molecular Biology (1994); 35: 91-169.
Ashby, et al., "Plasma hepcidin levels are elevated but responsive to erythropoietin therapy in renal disease." Kidney International (2009); 75 (9): 976-981.
Balasubramanian and Kuppuswamy, "RGD-containing Peptides Activate S6K1 through $\beta_3$ Integrin in Adult Cardiac Muscle Cells", J Biol Chem. (Oct. 24, 2003); 278(43): 42214-42224. Epub Aug. 9, 2003.
Boer, J., et al., "Design and Synthesis of Potent and Selective $\alpha_4\beta_7$ Integrin Antagonists." J. Med. Chem. (2001); 44 (16): 2586-2592.
Bowie, et al., "Deciphering the Message in Protein Sequences: Tolerance to Amino Acid Substitutions." Science (1990); 247: 1306-1310.
Chatterjee, J. et al., "N-Methylation of Peptides: a New Perspective in Medicinal Chemistry", Accounts of Chemical Research, 41(10): 1331-1342 (2008).
Clark, et al., "Understanding the Structure/Activity Relationships of the Iron Regulatory Peptide Hepcidin." Chem Biol. (Mar. 2011); 18(3): 336-343.
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from patent U.S. Pat. No. 8,313,950.", XP002761650, retrieved from EBI accession No. USPOP:AGA36544 Database accession No. AGA36544, 1 page.
Davies, J.S., "The Cyclization of Peptides and Depsipeptides", J Pept Sci. (Aug. 2003); 9(8): 471-501.
De Mast, et al., "Increased serum hepcidin and alterations in blood iron parameters associated with asymptomatic P. falciparum and P. vivax malaria." Haematologica (2010); 95 (7): 1068-1074.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective a4B7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report mailed Nov. 9, 2016, 9 pages.
European Application No. 14780207.8, Extended European Search Report mailed Feb. 17, 2017, 9 pages.
European Application No. 14780207.8, Partial Supplementary European Search Report mailed Nov. 16, 2016, 6 pages.
European Application No. 15792950.6, Extended European Search Report dated May 2, 2018, 10 pages.
European Application No. 15812513.8, Extended European Search Report dated Apr. 12, 2018, 11 pages.
European Application No. 15821351.2, Extended European Search Report dated Jan. 3, 2018, 6 pages.
European Application No. 15846131.9, Extended European Search Report dated Jan. 25, 2018, 8 pages.
European Application No. 15846983.3, Extended European Search Report dated Jun. 19, 2018, 10 pages.
European Application No. 15846983.3, Partial European Search Report dated Mar. 2, 2018, 11 pages.
European Application No. 16825301.1, Extended European Search Report dated Jan. 21, 2019, 6 pages.
Ganz and Nemeth, "Hepcidin and iron homeostasis." Biochimica et Biophysica Acta (BBA)—Molecular Cell Research (Sep. 2012); 1823 (9): 1434-1443.
Gee et al. "Cyclic Peptides as Non-carboxyl-terminal Ligands of Syntrophin PDZ Domains," The Journal of Biological Chemistry, 273(34): 21980-21987 (1998).
Girelli, Domenico, et al. "Hepcidin in the diagnosis of iron disorders." Blood (2016); 127.23 : 2809-2813.
Haanstra, et al., "Antagonizing the a4B1 Integrin, but No. a4B7, Inhibits Leukocytic Infiltration of the Central Nervous System in Rhesus Monkey Experimental Autoimmune Encephalomyelitis", Journal of Immunology, 90(5): 1961-1973 (2013).
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al. "Hepcidin revisited, disulfide connectivity, dynamics, and structure." Journal of Biological Chemistry (2009); 284.36: 24155-24167.
Kelleman, A. et al., "Incorporation of thioether building blocks into an $\alpha_v\beta_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.

(56) References Cited

OTHER PUBLICATIONS

Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Legge and Morieson, "On the prediction of partition coefficients and $R_F$ values of peptides." Aust. J. Biol. Sci. (1964); 17: 561-571.
Ley, Klaus, et al. "Integrin-based therapeutics: biological basis, clinical use and new drugs." Nature Reviews Drug Discovery (2016); 15.3: 173-183.
Li and Roller, "Cyclization Strategies in Peptide Derived Drug Design." Curr. Topics Med. Chem. (2002); 2: 325-341.
Liu, Shuang, "Radiolabeled Cyclic RGD Peptides as Integrin $\alpha_v\beta_3$-Targeted Radiotracers: Maximizing Binding Affinity via Bivalency." Bioconjugate Chem. (2009); 20 (12): 2199-2213.
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
Madsen, Kjeld, et al. "Structure-activity and protraction relationship of long-acting glucagon-like peptide-1 derivatives: importance of fatty acid length, polarity, and bulkiness." Journal of Medicinal Chemistry (2007); 50.24: 6126-6132.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Park, C.H., et al., "Hepcidin, a urinary antimicrobial peptide synthesized in the liver." J Biol Chem. (2001); 276(11): 7806-7810. Epub Dec. 11, 2000.
Parrow, et al., "Prospects for a hepcidin mimic to treat β-thalassemia and hemochromatosis." Expert Review of Hematology (2011); 4 (3): 233-235.
Pattarawarapan, "Selective Formation of Homo- and Heterobivalent Peptidomimetics." J. Med. Chem. (Aug. 2003); 46 (17): 3565-3567.
PCT/US2013/064439, International Preliminary Report on Patentability, dated Apr. 14, 2015, 8 pages.
PCT/US2013/064439, International Search Report and Written Opinion, mailed Jan. 24, 2014, 15 pages.
PCT/US2014/030352, International Preliminary Report on Patentability, dated Sep. 15, 2015, 7 pages.
PCT/US2014/030352, International Search Report and Written Opinion, mailed Nov. 28, 2014, 12 pages.
PCT/US2014/030352, Invitation to Pay Additional Fees, mailed Sep. 10, 2014, 2 pages.
PCT/US2014/032391, International Preliminary Report on Patentability, dated Oct. 6, 2015, 8 pages.
PCT/US2014/032391, International Search Report, mailed Aug. 7, 2014, 5 pages.
PCT/US2014/032391, Written Opinion, mailed Aug. 7, 2014, 7 pages.
PCT/US2014/032392, International Preliminary Report on Patentability, dated Oct. 6, 2015, 10 pages.
PCT/US2014/032392, International Search Report and Written Opinion, mailed Sep. 15, 2014, 15 pages.
PCT/US2015/031243, International Preliminary Report on Patentability, mailed Nov. 22, 2016, 8 pages.
PCT/US2015/031243, International Search Report and Written Opinion, mailed Aug. 5, 2015, 14 pages.
PCT/US2015/038370, International Preliminary Report on Patentability, mailed Dec. 27, 2016, 4 pages.
PCT/US2015/038370, International Search Report and Written Opinion, mailed Sep. 14, 2015, 5 pages.
PCT/US2015/040658, International Preliminary Report on Patentability, mailed Jan. 17, 2017, 5 pages.
PCT/US2015/040658, International Search Report and Written Opinion, mailed Oct. 28, 2015, 12 pages.
PCT/US2015/053558, International Preliminary Report on Patentability, mailed Apr. 4, 2017, 9 pages.
PCT/US2015/053558, International Search Report and Written Opinion, mailed Feb. 19, 2016, 16 pages.
PCT/US2015/053558, Invitation to Pay Additional Fees, mailed Dec. 16, 2015, 3 pages.
PCT/US2015/053603, International Preliminary Report on Patentability, dated Apr. 4, 2017, 8 pages.
PCT/US2015/053603, International Search Report and Written Opinion, mailed Feb. 12, 2016, 13 pages.
PCT/US2015/053603, Invitation to Pay Additional Fees, mailed Dec. 10, 2015, 3 pages.
PCT/US2016/042680, (2nd) International Search Report and Written Opinion, mailed Apr. 17, 2017, 13 pages.
PCT/US2016/042680, International Search Report and Written Opinion, mailed Jan. 13, 2017, 12 pages.
PCT/US2016/069255, International Preliminary Report on Patentability, dated Jul. 3, 2018, 7 pages.
PCT/US2016/069255, International Search Report and Written Opinion mailed Jun. 1, 2017, 11 pages.
PCT/US2016/069255, Invitation to Pay Additional Fees, mailed Mar. 30, 2017, 2 pages.
PCT/US2017/044249, International Preliminary Report on Patentability, dated Jan. 29, 2019, 9 pages.
PCT/US2017/044249, International Search Report and Written Opinion, mailed Nov. 21, 2017, 14 pages.
PCT/US2017/044249, Invitation to Pay Additional Fees, mailed Sep. 14, 2017, 3 pages.
PCT/US2018/050480, International Search Report and Written Opinion, mailed Jan. 29, 2019, 13 pages.
PCT/US2018/050480, Invitation to Pay Additional Fees, mailed Nov. 6, 2018, 3 pages.
PCT/US2018/014257, International Preliminary Report on Patentability, dated Jul. 23, 2019, 9 pages.
PCT/US2018/014257, International Search Report and Written Opinion, mailed May 14, 2018, 13 pages.
PCT/US2018/014257, Invitation to Pay Additional Fees, mailed Mar. 22, 2018, 2 pages.
PCT/US2019/017192, Invitation to Pay Additional Fees, mailed Apr. 16, 2019, 2 pages.
PCT/US2019/041665, International Search Report and Written Opinion mailed Dec. 19, 2019, 16 pages.
PCT/US2019/041665, Invitation to Pay Additional Fees, mailed Oct. 22, 2019, 3 pages.
Pelton, J.T. et al., "Somatostatin Analogs with Affinity for Opiate Receptors in Rat Brain Binding Assay", Peptides, 6(Suppl 1): 159-163 (1985).
Preza, G., et al., "Minihepcidins are rationally designed small peptides that mimic hepcidin activity in mice and may be useful for the treatment of iron overload", J Clin Invest (2011); 121(12): 4880-4888.
Ramos, E., et al., "Minihepcidins prevent iron overload in a hepcidin-deficient mouse model of severe hemochromatosis." Blood (Nov. 2012); 120(18): 3829-3836. Epub Sep. 18, 2012.
Rivera, Seth, et al. "Synthetic hepcidin causes rapid dose-dependent hypoferremia and is concentrated in ferroportin-containing organs." Blood (2005); 106.6: 2196-2199.
Rostovtsev, et al., "A Stepwise Huisgen Cycloaddition Process: Copper(I)-Catalyzed Regioselective "Ligation" of Azides and Terminal Alkynes". Angewandte Chemie Int. Ed. (Jul. 2, 2002); 41(14): 2596-2599.

(56) References Cited

OTHER PUBLICATIONS

Sasaki, et al., "D-Arg2-dermorphin tetrapeptide analogs: a potent and long-lasting analgesic activity after subcutaneous administration." Biochem Biophys Res Commun. (1984); 120 (1): 214-218.
Search Report and Written Opinion in Singaporean Application No. 11201609614Q, dated Mar. 12, 2018, 9 pages.
Search Report and Written Opinion in Singaporean Application No. 11201610799W, dated May 31, 2018, 4 pages.
Search Report and Written Opinion in Singaporean Application No. 11201700327W, dated Mar. 16, 2018, 10 pages.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Speers, et al., "Activity-Based Protein Profiling in Vivo Using a Copper(I)-Catalyzed Azide-Alkyne [3 +2] Cycloaddition". J. Am. Chem. Soc. (Mar. 28, 2003); 125(16): 4686-4687.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Tornøe, et al., "Peptidotriazoles on solid phase: [1,2,3]-triazoles by regiospecific copper(i)-catalyzed 1,3-dipolar cycloadditions of terminal alkynes to azides." J Org Chem. (May 3, 2002); 67(9): 3057-3064.
Tuvia, et al., "A Novel Suspension Formulation Enhances Intestinal Absorption of Macromolecules Via Transient and Reversible Transport Mechanisms". Pharm Res. (Feb. 21, 2014); 31(8): 2010-2021.
U.S. Appl. No. 14/050,349, Final Office Action dated Sep. 9, 2015, 17 pages.
U.S. Appl. No. 14/050,349, Non-Final Office Action dated Feb. 27, 2015, 14 pages.
U.S. Appl. No. 14/050,349, Notice of Allowance dated Jan. 12, 2016, 9 pages.
U.S. Appl. No. 14/229,784, Non-Final Office Action dated Aug. 13, 2015, 16 pages.
U.S. Appl. No. 14/229,784, Office Action dated Mar. 8, 2016, 6 pages.
U.S. Appl. No. 14/229,799, Non-Final Office Action dated Jul. 24, 2015, 19 pages.
U.S. Appl. No. 14/229,799, Office Action dated Mar. 4, 2016, 18 pages.
U.S. Appl. No. 14/714,198, Notice of Allowance mailed Mar. 17, 2017, 3 pages.
U.S. Appl. No. 14/714,198, Office Action mailed Nov. 7, 2016, 6 pages.
U.S. Appl. No. 14/775,469, Notice of Allowance mailed Aug. 10, 2017, 11 pages.
U.S. Appl. No. 14/775,469, Notice of Allowance mailed Sep. 5, 2017, 9 pages.
U.S. Appl. No. 14/775,469, Office Action mailed Apr. 11, 2017, 22 pages.
U.S. Appl. No. 14/800,627, Notice of Allowance mailed Feb. 15, 2017, 9 pages.
U.S. Appl. No. 14/800,627, Office Action mailed Aug. 25, 2016, 11 pages.
U.S. Appl. No. 14/872,975, Notice of Allowance mailed Aug. 16, 2017, 9 pages.
U.S. Appl. No. 14/872,975, Office Action mailed Dec. 27, 2016, 14 pages.
U.S. Appl. No. 15/046,325, Office Action mailed Aug. 1, 2016, 13 pages.
U.S. Appl. No. 15/442,229, Notice of Allowance dated Sep. 12, 2018, 9 pages.
U.S. Appl. No. 15/442,229, Office Action dated Apr. 20, 2018, 12 pages.
U.S. Appl. No. 15/514,983, Notice of Allowance dated Jan. 7, 2019, 6 pages.
U.S. Appl. No. 15/514,983, Office Action dated Nov. 2, 2018, 8 pages.
U.S. Appl. No. 15/614,047, Notice of Allowance dated Jun. 7, 2018, 8 pages.
U.S. Appl. No. 15/698,407, Office Action dated Apr. 25, 2019, 15 pages.
U.S. Appl. No. 15/698,407, Office Action dated Aug. 5, 2019, 10 pages.
U.S. Appl. No. 15/720,333, Office Action dated Aug. 28, 2018, 24 pages.
U.S. Appl. No. 15/745,371, Office Action dated Dec. 19, 2019, 22 pages.
U.S. Appl. No. 15/828,214, Notice of Allowance dated Jun. 11, 2018, 9 pages.
U.S. Appl. No. 15/828,214, Office Action dated May 15, 2018, 12 pages.
U.S. Appl. No. 15/831,087, Notice of Allowance dated May 11, 2018, 8 pages.
U.S. Appl. No. 15/831,087, Office Action dated Apr. 12, 2018, 10 pages.
U.S. Appl. No. 15/831,100, Notice of Allowance dated May 8, 2018, 8 pages.
U.S. Appl. No. 15/831,100, Office Action dated Apr. 12, 2018, 11 pages.
U.S. Appl. No. 15/836,648, Office Action dated Nov. 6, 2018, 7 pages.
U.S. Appl. No. 16/037,982, Office Action dated Mar. 22, 2019, 29 pages.
U.S. Appl. No. 16/039,813, Corrected Notice of Allowability mailed Jan. 31, 2020, 5 pages.
U.S. Appl. No. 16/039,813, Notice of Allowance mailed Nov. 7, 2019, 10 pages.
U.S. Appl. No. 16/039,813, Office Action dated Apr. 19, 2019, 11 pages.
U.S. Appl. No. 16/039,813, Office Action dated Aug. 22, 2019, 11 pages.
U.S. Appl. No. 16/128,352, Notice of Allowability dated Feb. 21, 2019, 2 pages.
U.S. Appl. No. 16/128,352, Notice of Allowance dated Feb. 6, 2019, 5 pages.
U.S. Appl. No. 16/289,451, Office Action dated Mar. 21, 2019, 21 pages.
Waitemata District Health Board, "Crushing Guide for Oral Medication in Residential Aged Care", 2 pages (2011).
Wang, et al., "Bioconjugation by Copper(I)-Catalyzed Azide-Alkyne [3 +2] Cycloaddition". J Am Chem Soc. (Mar. 19, 2003); 125(11): 3192-3193.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yampolsky and Stoltzfus, "The Exchangeability of Amino Acids in Proteins", Genetics (Aug. 2005); 170(4): 1459-1472. Epub Jun. 8, 2005.
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
European Application No. 19750312.1, Partial Supplementary European Search Report dated Nov. 29, 2021, 13 pages.

(56) References Cited

OTHER PUBLICATIONS

Hawe, et al., “Forced degradation of therapeutic proteins.” J Pharm Sci. (Mar. 2012); 101(3): 895-913. Epub Nov. 14, 2011.
PCT/US2020/041409, International Preliminary Report on Patentability, dated Jan. 11, 2022, 8 pages.
U.S. Appl. No. 16/510,118, Office Action mailed Mar. 18, 2021, 14 pages.
U.S. Appl. No. 16/510,118, Notice of Allowance mailed Sep. 13, 2021, 8 pages.
U.S. Appl. No. 17/061,336, Office Action mailed Jan. 12, 2022, 17 pages.
U.S. Appl. No. 17/099,308, Office Action mailed Jan. 3, 2022, 28 pages.
Duffy et al., “Virtual Screening Using Combinatorial Cyclic Peptide Libraries Reveals Protein Interfaces Readily Targetable by Cyclic Peptides”, J. Chem. Inf. Model., Feb. 10, 2015 (Feb. 10, 2015), 55, pp. 600-613.
Iwasaki K, et al., “Selective Thioether Macrocyclization of Peptides Having the N-terminal Chloroacetyl Group and Competing Two or Three Cysteine Residues in Translation,” Org Biomol Chem., Aug. 14, 2012, 10(30), pp. 5783-5786. doi: 10.1039/c2ob25306b. Epub Mar. 14, 2012.
Knerr PJ, et al., “Synthesis and Activity of Thioether-containing Analogues of the Complement Inhibitor Compstatin,” ACS Chem Biol., Jul. 15, 2011, 6(7), pp. 753-760. doi: 10.1021/cb2000378. Epub May 23, 2011.
Krueger et al., “IL-23 past, present, and future: a roadmap to advancing IL-23 science and therapy.” Front Immunol. Apr. 15, 2024:15:1331217. doi: 10.3389/fimmu.2024.1331217. eCollection 2024, 15 pages.
Tang et al., “Interleukin-23: as a drug target for autoimmune inflammatory diseases.” Immunology. Feb. 2012; 135(2):112-24. doi: 10.1111/j.1365-2567.2011.03522.x.

* cited by examiner

SEQUENCE LISTING

```
<160> NUMBER OF SEQ ID NOS: 38

<210> SEQ ID NO 1
<211> LENGTH: 33
<212> TYPE: PRT
<213> ORGANISM: Artificial Sequence
<220> FEATURE:
<223> OTHER INFORMATION: Synthesized peptide inhibitor of IL23

<400> SEQUENCE: 1

Tyr Met Gln Cys Ile Arg Arg Leu Ile Glu Ala Ala Leu Asp Pro Asn
1               5                   10                  15

Leu Asn Leu Glu Gln Arg Pro Ala Lys Ile Pro Ser Ile Thr Asp Asp
            20                  25                  30

Cys


<210> SEQ ID NO 2
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 2

Phe Asn Met Val Cys Gln Asp Arg Phe Tyr Thr Ala Ala Ala Trp Pro
1               5                   10                  15

Asn Leu Asn Glu Glu Phe Arg Asn Ala Phe Ile Leu Ser Leu Arg Asp
            20                  25                  30

Phe Cys


<210> SEQ ID NO 3
<211> LENGTH: 34
<212> TYPE: PRT
<213> ORGANISM: Artificial Sequence
```

<220> FEATURE:
<223> OTHER INFORMATION: Synthesized peptide inhibitor of IL23

<400> SEQUENCE: 3

Phe Asn Met Phe Cys Gln Arg Leu Phe Tyr Trp Ala Ala Ala Asn Pro
1 5 10 15

Asn Leu Asn Glu Glu Asp Arg Asn Ala Arg Ile Leu Ser Phe Arg Asp
20 25 30

Gly Cys

<210> SEQ ID NO 4
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 4

Phe Asn Met Val Cys Gln Arg Gly Phe Tyr Val Ala Ala Ala Asp Pro
1 5 10 15

Asn Leu Asn Glu Glu Phe Arg Asn Ala Leu Ile Leu Ser Leu Arg Asp
20 25 30

Phe Cys

<210> SEQ ID NO 5
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 5

Phe Asn Met Ile Cys Gln Glu Gly Phe Tyr Pro Ala Ala Ala Trp Pro
1 5 10 15

Asn Leu Asn Glu Glu Phe Arg Asn Ala Phe Ile Leu Ser Leu Arg Asp
20 25 30

Phe Cys

<210> SEQ ID NO 6
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 6

Phe Asn Met Ser Cys Gln Ile Arg Phe Tyr Leu Ala Ala Ala Asp Pro
1 5 10 15

Asn Leu Asn Glu Glu Glu Arg Asn Ala Leu Ile Lys Ser Leu Arg Asp
20 25 30

Met Cys

<210> SEQ ID NO 7
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 7

Phe Asn Met Leu Cys Gln Ile Arg Phe Tyr Ile Ala Ala Ala Leu Pro
1 5 10 15

Asn Leu Asn Glu Glu Asn Arg Asn Ala Asn Ile Lys Ser Ile Arg Asp
20 25 30

Arg Cys

<210> SEQ ID NO 8
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 8

Phe Asn Met Gln Cys Leu Arg Arg Met Val Glu Ala Gly Ile Asp Pro
1 5 10 15

Asn Leu Asn Ser Gly Gln Arg Trp Ala Lys Ile Arg Ser Ile Phe Asp
20 25 30

Asp Cys

<210> SEQ ID NO 9
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 9

Phe Asn Met Phe Cys Gln Leu Ala Phe Tyr Ser Ala Ala Ala Asp Pro
1 5 10 15

Asn Leu Asn Glu Glu Gln Arg Asn Ala Lys Ile Lys Ser Phe Arg Asp
20 25 30

Leu Cys

<210> SEQ ID NO 10
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 10

Phe Asn Met Gln Cys Leu Arg Arg Met Ser Glu Ala Gly Val Asp Pro
1 5 10 15

Asn Leu Asn Gln Glu Gln Arg Trp Ala Lys Ile Lys Ser Ile Met Asp
20 25 30

Asp Cys

<210> SEQ ID NO 11
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 11

Phe Asn Met Gln Cys Ala Arg Arg Met Ser Glu Ala Gly Val Asp Pro
1 5 10 15

Asn Leu Asn Gln Glu Gln Arg Trp Ala Lys Ile Lys Ser Ile Met Asp
20 25 30

Asp Cys

<210> SEQ ID NO 12
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 12

```
Phe Asn Met Gln Cys Leu Arg Arg Ala Ser Glu Ala Gly Val Asp Pro
1               5                   10                  15

Asn Leu Asn Gln Glu Gln Arg Trp Ala Lys Ile Lys Ser Ile Met Asp
            20                  25                  30

Asp Cys
```

<210> SEQ ID NO 13
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 13

```
Phe Asn Met Gln Cys Leu Arg Arg Met Ala Glu Ala Gly Val Asp Pro
1               5                   10                  15

Asn Leu Asn Gln Glu Gln Arg Trp Ala Lys Ile Lys Ser Ile Met Asp
            20                  25                  30

Asp Cys
```

<210> SEQ ID NO 14
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 14

```
Phe Asn Met Gln Cys Leu Arg Arg Met Ser Glu Ala Ala Val Asp Pro
1               5                   10                  15

Asn Leu Asn Gln Glu Gln Arg Trp Ala Lys Ile Lys Ser Ile Met Asp
            20                  25                  30

Asp Cys
```

<210> SEQ ID NO 15
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 15

```
Phe Asn Met Gln Cys Leu Arg Arg Met Ser Glu Ala Gly Ala Asp Pro
1               5                   10                  15

Asn Leu Asn Gln Glu Gln Arg Trp Ala Lys Ile Lys Ser Ile Met Asp
            20                  25                  30

Asp Cys
```

<210> SEQ ID NO 16
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 16

```
Phe Asn Met Gln Cys Leu Arg Arg Met Ser Glu Ala Gly Val Asp Ala
1               5                   10                  15

Asn Leu Asn Gln Glu Gln Arg Trp Ala Lys Ile Lys Ser Ile Met Asp
            20                  25                  30

Asp Cys
```

<210> SEQ ID NO 17
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 17

```
Phe Asn Met Gln Cys Leu Arg Arg Met Ser Glu Ala Gly Val Asp Pro
1               5                   10                  15

Asn Leu Ala Gln Glu Gln Arg Trp Ala Lys Ile Lys Ser Ile Met Asp
            20                  25                  30

Asp Cys
```

<210> SEQ ID NO 18
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 18

```
Phe Asn Met Gln Cys Leu Arg Arg Met Ser Glu Ala Gly Val Asp Pro
1               5                   10                  15

Asn Leu Asn Ala Glu Gln Arg Trp Ala Lys Ile Lys Ser Ile Met Asp
            20                  25                  30

Asp Cys
```

<210> SEQ ID NO 19
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 19

```
Phe Asn Met Gln Cys Leu Arg Arg Met Ser Glu Ala Gly Val Asp Pro
1               5                   10                  15

Asn Leu Asn Gln Glu Gln Ala Trp Ala Lys Ile Lys Ser Ile Met Asp
            20                  25                  30

Asp Cys
```

<210> SEQ ID NO 20
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 20

```
Phe Asn Met Gln Cys Leu Arg Arg Met Ser Glu Ala Gly Val Asp Pro
1               5                   10                  15

Asn Leu Asn Gln Glu Gln Arg Ala Ala Lys Ile Lys Ser Ile Met Asp
            20                  25                  30
```

-continued

Asp Cys

<210> SEQ ID NO 21
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 21

Phe Asn Met Gln Cys Leu Arg Arg Met Ser Glu Ala Gly Val Asp Pro
1 5 10 15

Asn Leu Asn Gln Glu Gln Arg Trp Ala Lys Ala Lys Ser Ile Met Asp
20 25 30

Asp Cys

<210> SEQ ID NO 22
<211> LENGTH: 34
<212> TYPE: PRT
<213> ORGANISM: Artificial Sequence
<220> FEATURE:
<223> OTHER INFORMATION: Synthesized peptide inhibitor of IL23

<400> SEQUENCE: 22

Phe Asn Met Gln Cys Leu Arg Arg Met Ser Glu Ala Gly Val Asp Pro
1 5 10 15

Asn Leu Asn Gln Glu Gln Arg Trp Ala Lys Ile Ala Ser Ile Met Asp
20 25 30

Asp Cys

<210> SEQ ID NO 23
<211> LENGTH: 39
<212> TYPE: PRT
<213> ORGANISM: Artificial Sequence
<220> FEATURE:
<223> OTHER INFORMATION: IL23 peptide inhibitor amino acid formula
<220> FEATURE:
<221> NAME/KEY: MISC_FEATURE
<222> LOCATION: (1)..(4)
<223> OTHER INFORMATION: Xaa is any amino acid or is absent
<220> FEATURE:
<221> NAME/KEY: MISC_FEATURE
<222> LOCATION: (5)..(5)
<223> OTHER INFORMATION: Xaa is an amino acid, an aliphatic acid, an alicyclic acid, or a modified 2-methyl aromatic acid each having a side chain with one or two carbons and capable of forming a thioether bond with X34
<220> FEATURE:
<221> NAME/KEY: MISC_FEATURE
<222> LOCATION: (6)..(6)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (7)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is Gly
<220> FEATURE:
<221> NAME/KEY: MISC_FEATURE
<222> LOCATION: (14)..(14)
<223> OTHER INFORMATION: Xaa is Val or Leu
<220> FEATURE:
<221> NAME/KEY: MISC_FEATURE
<222> LOCATION: (15)..(19)
<223> OTHER INFORMATION: Xaa is any amino acid
<220> FEATURE:

```
<221> NAME/KEY: MISC_FEATURE
<222> LOCATION: (20)..(20)
<223> OTHER INFORMATION: Xaa is Gln, Asn, Glu, Asp or Ser
<220> FEATURE:
<221> NAME/KEY: MISC_FEATURE
<222> LOCATION: (21)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is Cys, D-Cys, Pen, N-Me-Cys, hCys, D-Pen,
      D-hCys or hSerCl
<220> FEATURE:
<221> NAME/KEY: MISC_FEATURE
<222> LOCATION: (35)..(39)
<223> OTHER INFORMATION: Xaa is any amino acid or is absent

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35


<210> SEQ ID NO 24
<211> LENGTH: 30
<212> TYPE: PRT
<213> ORGANISM: Artificial Sequence
<220> FEATURE:
<223> OTHER INFORMATION: Consensus amino acid sequence of peptide
      inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
      alicyclic acid, or a modified 2-methyl aromatic acid having a side
      chain, each with one or two carbons and capable of forming a
      thioether bond with X30
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
      or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(29)
<223> OTHER INFORMATION: Xaa is amino acid
<220> FEATURE:
<221> NAME/KEY: MISC_FEATURE
<222> LOCATION: (30)..(30)
<223> OTHER INFORMATION: Xaa is Cys, D-Cys, Pen, D-Pen or hCys,
      hSer(Cl), N-Me-Cys, Pen(=O), or D-hCys
<220> FEATURE:
<221> NAME/KEY: MISC_FEATURE
```

<222> LOCATION: (30)..(30)
<223> OTHER INFORMATION: Xaa is Cys, D-Cys, Pen, D-Pen or h-Cys, hSer(Cl), N-Me-Cys or D-hCys

<400> SEQUENCE: 24

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa
20 25 30

<210> SEQ ID NO 25
<211> LENGTH: 29
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X29
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(28)
<223> OTHER INFORMATION: Xaa is amino acid
<220> FEATURE:
<221> NAME/KEY: MISC_FEATURE
<222> LOCATION: (29)..(29)
<223> OTHER INFORMATION: Xaa is Cys, D-Cys, Pen, D-Pen or hCys, hSer(Cl), N-Me-Cys, Pen(=O), or D-hCys

<400> SEQUENCE: 25

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa
20 25

<210> SEQ ID NO 26
<211> LENGTH: 28
<212> TYPE: PRT
<213> ORGANISM: Artificial Sequence
<220> FEATURE:
<223> OTHER INFORMATION: Consensus amino acid sequence of peptide inhibitor
<220> FEATURE:

<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X28
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(27)
<223> OTHER INFORMATION: Xaa is amino acid
<220> FEATURE:
<221> NAME/KEY: MISC_FEATURE
<222> LOCATION: (28)..(28)
<223> OTHER INFORMATION: Xaa is Cys, D-Cys, Pen, D-Pen or h-Cys, hSer(Cl), N-Me-Cys or D-hCys

<400> SEQUENCE: 26

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25
```

<210> SEQ ID NO 27
<211> LENGTH: 27
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X27
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE -continued
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(26)
<223> OTHER INFORMATION: Xaa is amino acid
<220> FEATURE:
<221> NAME/KEY: MISC_FEATURE
<222> LOCATION: (27)..(27)
<223> OTHER INFORMATION: Xaa is Cys, D-Cys, Pen, D-Pen or h-Cys, hSer(Cl), N-Me-Cys or D-hCys

<400> SEQUENCE: 27

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa
20 25

<210> SEQ ID NO 28
<211> LENGTH: 26
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X26
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(25)
<223> OTHER INFORMATION: Xaa is amino acid
<220> FEATURE:
<221> NAME/KEY: MISC_FEATURE
<222> LOCATION: (26)..(26)
<223> OTHER INFORMATION: Xaa is Cys, D-Cys, Pen, D-Pen or h-Cys, hSer(Cl), N-Me-Cys or D-hCys

<400> SEQUENCE: 28

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25


<210> SEQ ID NO 29
<211> LENGTH: 25
<212> TYPE: PRT
<213> ORGANISM: Artificial Sequence
<220> FEATURE:
<223> OTHER INFORMATION: Consensus amino acid sequence of peptide
      inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
      alicyclic acid, or a modified 2-methyl aromatic acid having a side
      chain, each with one or two carbons and capable of forming a
      thioether bond with X25
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
      or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(24)
<223> OTHER INFORMATION: Xaa is amino acid
<220> FEATURE:
<221> NAME/KEY: MISC_FEATURE
<222> LOCATION: (25)..(25)
<223> OTHER INFORMATION: Xaa is Cys, D-Cys, Pen, D-Pen or h-Cys,
      hSer(Cl), N-Me-Cys or D-hCys

<400> SEQUENCE: 29

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25


<210> SEQ ID NO 30
<211> LENGTH: 24
<212> TYPE: PRT
<213> ORGANISM: Artificial Sequence
<220> FEATURE:
<223> OTHER INFORMATION: Consensus amino acid sequence of peptide
      inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
      alicyclic acid, or a modified 2-methyl aromatic acid having a side
      chain, each with one or two carbons and capable of forming a
```

```
      thioether bond with X24
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
      or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(23)
<223> OTHER INFORMATION: Xaa is amino acid
<220> FEATURE:
<221> NAME/KEY: MISC_FEATURE
<222> LOCATION: (24)..(24)
<223> OTHER INFORMATION: Xaa is Cys, D-Cys, Pen, D-Pen or h-Cys,
      hSer(Cl), N-Me-Cys or D-hCys

<400> SEQUENCE: 30

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20


<210> SEQ ID NO 31
<211> LENGTH: 23
<212> TYPE: PRT
<213> ORGANISM: Artificial Sequence
<220> FEATURE:
<223> OTHER INFORMATION: Consensus amino acid sequence of peptide
      inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
      alicyclic acid, or a modified 2-methyl aromatic acid having a side
      chain, each with one or two carbons and capable of forming a
      thioether bond with X23
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
      or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
```

<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(22)
<223> OTHER INFORMATION: Xaa is amino acid
<220> FEATURE:
<221> NAME/KEY: MISC_FEATURE
<222> LOCATION: (23)..(23)
<223> OTHER INFORMATION: Xaa is Cys, D-Cys, Pen, D-Pen or h-Cys, hSer(Cl), N-Me-Cys or D-hCys

<400> SEQUENCE: 31

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20
```

<210> SEQ ID NO 32
<211> LENGTH: 22
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X22
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(21)
<223> OTHER INFORMATION: Xaa is amino acid
<220> FEATURE:
<221> NAME/KEY: MISC_FEATURE
<222> LOCATION: (22)..(22)
<223> OTHER INFORMATION: Xaa is Cys, D-Cys, Pen, D-Pen or h-Cys, hSer(Cl), N-Me-Cys or D-hCys

<400> SEQUENCE: 32

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
```

20

<210> SEQ ID NO 33
<211> LENGTH: 21
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X21
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(20)
<223> OTHER INFORMATION: Xaa is amino acid
<220> FEATURE:
<221> NAME/KEY: MISC_FEATURE
<222> LOCATION: (21)..(21)
<223> OTHER INFORMATION: Xaa is Cys, D-Cys, Pen, D-Pen or h-Cys, hSer(Cl), N-Me-Cys or D-hCys

<400> SEQUENCE: 33

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20
```

<210> SEQ ID NO 34
<211> LENGTH: 20
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X20
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(19)
<223> OTHER INFORMATION: Xaa is amino acid
<220> FEATURE:
<221> NAME/KEY: MISC_FEATURE
<222> LOCATION: (20)..(20)
<223> OTHER INFORMATION: Xaa is Cys, D-Cys, Pen, D-Pen or h-Cys,
hSer(Cl), N-Me-Cys or D-hCys

<400> SEQUENCE: 34

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```

<210> SEQ ID NO 35
<211> LENGTH: 19
<212> TYPE: PRT
<213> ORGANISM: Artificial Sequence
<220> FEATURE:
<223> OTHER INFORMATION: Consensus amino acid sequence of peptide
inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
alicyclic acid, or a modified 2-methyl aromatic acid having a side
chain, each with one or two carbons and capable of forming a
thioether bond with X19
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(18)
<223> OTHER INFORMATION: Xaa is amino acid
<220> FEATURE:
<221> NAME/KEY: MISC_FEATURE
<222> LOCATION: (19)..(19)
<223> OTHER INFORMATION: Xaa is Cys, D-Cys, Pen, D-Pen or h-Cys, hSer(Cl), N-Me-Cys or D-hCys

<400> SEQUENCE: 35

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

<210> SEQ ID NO 36
<211> LENGTH: 18
<212> TYPE: PRT
<213> ORGANISM: Artificial Sequence
<220> FEATURE:
<223> OTHER INFORMATION: Consensus amino acid sequence of peptide inhibitor
<220> FEATURE:
<221> NAME/KEY: MISC_FEATURE
<222> LOCATION: (1)..(1)
<223> OTHER INFORMATION: Xaa is an amino acid, an aliphatic acid, an alicyclic acid, or a modified 2-methyl aromatic acid having a side chain, each with one or two carbons and capable of forming a thioether bond with X18
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(17)
<223> OTHER INFORMATION: Xaa is amino acid
<220> FEATURE:
<221> NAME/KEY: MISC_FEATURE
<222> LOCATION: (18)..(18)
<223> OTHER INFORMATION: Xaa is Cys, D-Cys, Pen, D-Pen or h-Cys, hSer(Cl), N-Me-Cys or D-hCys

<400> SEQUENCE: 36

```
Xaa Xaa Xaa Xaa Xaa Xaa Xaa Xaa Xaa Xaa Xaa Xaa Xaa Xaa Xaa Xaa
1               5                   10                  15

Xaa Xaa
```

<210> SEQ ID NO 37
<211> LENGTH: 17
<212> TYPE: PRT
<213> ORGANISM: Artificial Sequence

```
<220> FEATURE:
<223> OTHER INFORMATION: Consensus amino acid sequence of peptide
      inhibitor
<220> FEATURE:
<221> NAME/KEY: MISC_FEATURE
<222> LOCATION: (1)..(1)
<223> OTHER INFORMATION: Xaa is an amino acid, an aliphatic acid, an
      alicyclic acid, or a modified 2-methyl aromatic acid having a side
      chain, each with one or two carbons and capable of forming a
      thioether bond with X18
<220> FEATURE:
<221> NAME/KEY: MISC_FEATURE
<222> LOCATION: (2)..(2)
<223> OTHER INFORMATION: Xaa is Leu, Ala, Val, Ile, hLeu, Cha, hCha, Asn
      or Gln
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Gly
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (11)..(15)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Gln, Asn, Glu, Asp or Ser
<220> FEATURE:
<221> NAME/KEY: MISC_FEATURE
<222> LOCATION: (17)..(17)
<223> OTHER INFORMATION: Xaa is Cys, D-Cys, Pen, D-Pen or h-Cys,
      hSer(Cl), N-Me-Cys or D-hCys

<400> SEQUENCE: 37

Xaa Xaa Xaa Xaa Xaa Xaa Xaa Xaa Xaa Xaa Xaa Xaa Xaa Xaa Xaa Xaa
1               5                   10                  15

Xaa


<210> SEQ ID NO 38
<211> LENGTH: 39
<212> TYPE: PRT
<213> ORGANISM: Artificial Sequence
<220> FEATURE:
<223> OTHER INFORMATION: IL23 peptide inhibitor amino acid formula
<220> FEATURE:
<221> NAME/KEY: MISC_FEATURE
<222> LOCATION: (1)..(4)
<223> OTHER INFORMATION: Xaa is any amino acid or absent
<220> FEATURE:
<221> NAME/KEY: MISC_FEATURE
<222> LOCATION: (5)..(5)
<223> OTHER INFORMATION: Xaa is an amino acid, an aliphatic acid, an
      alicyclic acid, or a modified 2-methyl aromatic acid, each having
      a side chain with one or two carbons and capable of forming a
      thioether bond with X34
<220> FEATURE:
<221> NAME/KEY: MISC_FEATURE
<222> LOCATION: (6)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is Cys, D-Cys, Pen, N-Me-Cys, hCys, D-Pen,
      D-hCys or hSerCl
<220> FEATURE:
<221> NAME/KEY: MISC_FEATURE
<222> LOCATION: (35)..(39)
<223> OTHER INFORMATION: Xaa is any amino acid or absent
```

-continued

```
<400> SEQUENCE: 38

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35
```

PEPTIDE INHIBITORS OF INTERLEUKIN-23 AND THEIR USE TO TREAT INFLAMMATORY DISEASES

CROSS REFERENCE TO RELATED APPLICATIONS

This application claims the benefit of International PCT Application No. PCT/US2017/044249, filed Jul. 27, 2017, which claims priority to U.S. Provisional Application No. 62/367,549, filed on Jul. 27, 2016; all of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is PRTH-003-01US_Seq_Listing.txt. The text file is 29,775 bytes, was created on Jan. 23, 2019, and is being submitted electronically via EFS-Web.

FIELD OF THE INVENTION

The present invention relates to novel peptide inhibitors of interleukin-23, and their use to treat or prevent a variety of diseases and disorders, including inflammatory bowel disease, Crohn's disease and psoriasis.

BACKGROUND

The interleukin-2 (IL-23) cytokine has been implicated as playing a crucial role in the pathogenesis of autoimmune inflammation and related diseases and disorders, such as multiple sclerosis, asthma, rheumatoid arthritis, inflammatory bowel diseases (IBDs), Crohn's disease, and psoriasis. It is believed that IL-23 mediates this effect by promoting the development of a pathogenic $CD4^+$ T cell population that produces IL-6, IL-17, and tumor necrosis factor (TNF). Production of IL-23 is enriched in the intestine, where it is believed to play a key role in regulating the balance between tolerance and immunity through T-cell-dependent and T-cell-independent pathways of intestinal inflammation through effects on T-helper 1 (Th 1)- and Th 17-associated cytokines, as well as restraining regulatory T-cell responses in the gut, favoring inflammation. In addition, polymorphisms in the IL-23 receptor (IL-23R) have been associated with susceptibility to IBDs, further establishing the critical role of the IL-23 pathway in intestinal homeostasis.

IL-23 is a heterodimer composed of a unique p19 subunit and the p40 subunit of IL-12, which is a cytokine involved in the development of interferon-γ (IFN-γ)-producing T helper 1 ($T_H1$) cells. Although IL-23 and IL-12 both contain the p40 subunit, they have different phenotypic properties. For example, animals deficient in IL-12 are susceptible to inflammatory autoimmune diseases, whereas IL-23 deficient animals are resistant, presumably due to a reduced number of $CD4^+$ T cells producing IL-6, IL-17, and TNF in the central nervous system (CNS) of IL-23-deficient animals. IL-23 binds to IL-23R, which is a heterodimeric receptor composed of IL-12Rβ1 and IL-23R subunits. Binding of IL-23 to IL-23R activates the Jak-stat signaling molecules, Jak2, Tyk2, and Stat1, Stat3, Stat4, and Stat5, although Stat4 activation is substantially weaker and different DNA-binding Stat complexes form in response to IL-23 as compared with IL-12. IL-23R associates constitutively with Jak2 and in a ligand-dependent manner with Stat3. In contrast to IL-12, which acts mainly on naive CD4(+) T cells, IL-23 preferentially acts on memory CD4(+) T cells.

Efforts have been made to identify therapeutic moieties that inhibit the IL-23 pathway, for use in treating IL-23-related diseases and disorders. A number of antibodies that bind to IL-23 or IL-23R have been identified, including ustekinumab, a humanized antibody that binds IL-23, which has been approved for the treatment of psoriasis. More recently, polypeptide inhibitors that bind to IL-23R and inhibit the binding of IL-23 to IL-23R have been identified (see, e.g., US Patent Application Publication No. US2013/0029907). While these findings are promising, challenges remain with respect to identifying stable and selective agents that preferentially target the IL-23 pathway in the intestine, which can be used for the treatment of intestinal inflammation and related disorders, such as IBDs and Crohn's disease.

Clearly, there remains a need in the art for new therapeutics targeting the IL-23 pathway, which may be used to treat and prevent IL-23-associated diseases, including those associated with autoimmune inflammation in the intestinal tract. The present invention addresses this need.

BRIEF SUMMARY OF THE INVENTION

The present invention provides peptide inhibitors of IL-23 and related methods.

In one embodiment, the peptide inhibitor has the structure of Formula I $$R^1\text{—X—}R^2 \quad \text{(I)}$$

or a pharmaceutically acceptable salt or solvate thereof, wherein $R^1$ is hydrogen, an C1-C6 alkyl, a C6-C12 aryl, a C6-C12 aryl C1-C6 alkyl, a C1-C20 alkanoyl 10 (optionally selected from acetyl, propionyl, formyl, benzoyl, trifluoroacetyl, isovaleric acid, isobutyric acid, octanoyl, lauroyl, hexadecanoyl, or γ-Glu-hexadecanoyl), and including PEGylated versions alone or as spacers of any of the foregoing;

$R^2$ is OH or $NH_2$; and

X is an amino acid sequence of 30-50 amino acids in length comprising the sequence of Formula Ib (SEQ ID NO:23):

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38-X39 (Ia), wherein X1 is absent or any amino acid;

X2 is absent or any amino acid;

X3 is absent or any amino acid;

X4 is absent or any amino acid;

X5 is an amino acid, an aliphatic acid, an alicyclic acid, or a modified 2-methyl aromatic acid, each comprising at least two carbons and capable of forming a thioether or disulfide bond with X34, wherein X5 is optionally selected from Cys, D-Cys, Pen, hCys, D-Pen, hSerCl, N-Me-Cys, D-hCys, hSer, hSer(Cl), 2-chloromethyl-benzoic acid, mercapto-propanoic acid, mercapto-butyric acid, 2-chloro-acetic acid, 3-choro-propanoic acid, 4-chloro-butyric acid, and 3-chloro-isobutyric acid, or an isostere of any of the foregoing amino acids;

X6 is any amino acid, wherein X6 is optionally Leu, Ala, Val, Ile, hLeu, Cha, hCha, Asn or Gln, or an isostere of any of the foregoing amino acids;

X7 is any amino acid;
X8 is any amino acid;
X9 is any amino acid;
X10 is any amino acid;
X11 is any amino acid;
X12 is any amino acid;
X13 is any amino acid, wherein X13 is optionally Gly or an isostere thereof;
X14 is Val or Leu, or an isostere of any of the foregoing;
X15 is any amino acid;
X16 is any amino acid;
X17 is any amino acid;
X18 is any amino acid;
X19 is any amino acid;
X20 is an amino acid, wherein X20 is optionally Gln, Asn, Glu. Asp or Ser, or an isostere of any of the foregoing;
X21 is any amino acid;
X22 is any amino acid;
X23 is any amino acid;
X24 is any amino acid;
X25 is any amino acid;
X26 is any amino acid;
X27 is any amino acid;
X28 is any amino acid;
X29 is any amino acid;
X30 is any amino acid;
X31 is any amino acid;
X32 is any amino acid;
X33 is any amino acid;
X34 is Cys, D-Cys, Pen, N-Me-Cys, hCys, D-Pen, D-hCys, hSer or hSerCl, or an isostere of any of the foregoing;
X35 is absent or any amino acid;
X36 is absent or any amino acid;
X37 is absent or any amino acid;
X38 is absent or any amino acid; and
X39 is absent or any amino acid.

In particular embodiments, the peptide inhibitor comprises a disulfide bond or a thioether bond between X5 and X34. In certain embodiments, each of X5 and X34 are selected from Cys, D-Cys, Pen, hCys, D-Pen, N-Me-Cys, and D-hCys; and there is a disulfide bond between X5 and X34. In certain embodiments, X5 is selected from Cys. D-Cys, Pen, hCys, D-Pen, N-Me-Cys, D-hCys, hSer, hSer (Cl), 2-chloromethylbenzoic acid, mercapto-propanoic acid, mercapto-butyric acid, 2-chloro-acetic acid, 3-choro-propanoic acid, 4-chloro-butyric acid, and 3-chloro-isobutyric acid; X34 is selected from Cys, D-Cys, Pen, N-Me-Cys, hCys, D-Pen, D-hCys, hSer or hSerCl; and there is a thioether bond between X5 and X34. In certain embodiments, X5 is an amino acid, an aliphatic acid, an alicyclic acid, or a modified 2-methyl aromatic acid, each having a side chain with one or two carbons and capable of forming a thioether or disulfide bond with X34.

In particular embodiments, the peptide inhibitor comprises a conjugated chemical substitutent that enhances stability of the peptide inhibitor, e.g., a linear or branched PEG.

In certain embodiments, the peptide inhibitor comprises an amino acid sequence set forth in Table 2 or SEQ ID NOs: 1-22, or having at least 80%, at least 90%, at least 95%, at least 98%/o identity to an amino acid sequence set forth in Table 2 or SEQ ID NOs: 1-22.

In particular embodiments, the peptide inhibitor binds to IL-23 and inhibits IL-23 binding to IL-23R.

In a related embodiment, the present invention includes a polynucleotide comprising a sequence encoding any of the peptide inhibitors disclosed herein. In particular embodiments, the present invention includes a vector comprising a polynucleotide comprising a sequence encoding any of the peptide inhibitors disclosed herein. In particular embodiments, the present invention includes a method of producing a peptide inhibitor described herein, comprising chemically synthesizing the peptide inhibitor, or recombinantly producing the peptide inhibitor using an expression vector to produce the peptide inhibitor in a host cell.

In another related embodiment, the present invention includes a pharmaceutical composition comprising a peptide inhibitor, polynucleotide or vector disclosed herein and a pharmaceutically acceptable carrier, diluent and excipient. In some embodiments, the pharmaceutical composition comprises an enteric coating. In some embodiments, the enteric coating protects and releases the pharmaceutical composition within a subject's lower gastrointestinal system.

In a further related embodiment, the present invention includes a method for treating or preventing inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, psoriasis, psoriatic arthritis, or graft versus host disease in a subject, comprising providing to the subject an effective amount of a peptide inhibitor or pharmaceutical composition disclosed herein. In some embodiments, the pharmaceutical composition is provided to the subject by an oral, parenteral, intravenous, peritoneal, intradermal, subcutaneous, intramuscular, intrathecal, inhalation, vaporization, nebulization, sublingual, buccal, rectal, vaginal, or topical route of administration. In certain embodiments for treating or preventing IBD, the IBD is ulcerative colitis or Crohn's disease, and the pharmaceutical composition is provided to the subject by an oral route of administration. In certain embodiments for treating psoriasis, the psoriasis is plaque psoriasis, guttate psoriasis, inverse psoriasis, pustular psoriasis, Palmo-Plantar Pustulosis, psoriasis vulgaris, or erythrodermic psoriasis, and the pharmaceutical composition is provided to the subject topically or by a parenteral or intravenous route of administration. In particular embodiments, the peptide inhibitor inhibits binding of an interleukin-23 (IL-23) to the interleukin-23 receptor (IL-23R).

DETAILED DESCRIPTION OF THE INVENTION

Definitions and Nomenclature

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "peptide," as used herein, refers broadly to a sequence of two or more amino acids joined together by peptide bonds. It should be understood that this term does not connote a specific length of a polymer of amino acids, nor is it intended to imply or distinguish whether the peptide is produced using recombinant techniques, chemical or enzymatic synthesis, or is naturally occurring.

The term "thioether," as used herein, refers to a cyclized, covalent bond formed between an upstream amino acid or aromatic/aliphatic acid group, and a downstream sulfur-containing amino acid, or isostere thereof, i.e., a C—S bond.

The recitations "sequence identity". "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, 1) or the identical amino acid residue (e.g., Ala, Pro. Ser. Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40° % more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. Another example of a conservative substitution with a residue normally not found in endogenous, mammalian peptides and proteins is the conservative substitution of Arg or Lys with, for example, omithine, canavanine, aminoethylcysteine or another basic amino acid. In some embodiments, one or more cysteines of a peptide analogue of the invention may be substituted with another residue, such as a serine. For further information concerning phenotypically silent substitutions in peptides and proteins, see, for example, Bowie et. al. Science 247, 1306-1310, 1990. In the scheme shown below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|---|---|---|---|
| A | N | H | M | F |
| S | D | R | L | Y |
| T | E | K | I | W |
| P | Q | | V | |
| G | | | C | |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|---|---|---|---|---|
| A | E | H | M | F |
| L | D | R | S | Y |
| I | | K | T | W |
| P | | | C | |
| G | | | N | |
| V | | | Q | |

All peptide sequences are written according to the generally accepted convention whereby the N-terminal amino acid residue is on the left and the C-terminal amino acid residue is on the right. As used herein, the term "α-N-terminal" refers to the free α-amino group of an amino acid in a peptide, and the term "α-C-terminal" refers to the free α-carboxylic acid terminus of an amino acid in a peptide.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of Chemical Moieties

| Abbreviation | Definition |
|---|---|
| Ac- | Acetyl |
| $NH_2$ | Free Amine |
| $CONH_2$ | Amide |
| COOH | Acid |
| PEG2K | PolyEthylene Glycol Mol wt of 2000 Da |
| PEG3.4K | PolyEthylene Glycol Mol wt of 3400 Da |
| PEG5K | PolyEthylene Glycol Mol wt of 5000 Da |
| Trifluorobutyric acid | Acylated with 4,4,4-Trifluorobutyric acid |
| 2-Methly-trifluorobutyric acid | Acylated with 2-methy-4,4,4-Butyric acid |
| Trifluorpentanoic acid | Acylated with 5,5,5-Trifluoropentnoic acid |
| Pen | Penicillamine |
| Cha | Cyclohexylalanine |
| hCha | Homocyclohexylalanine |
| Cyclobutyl | Cyclobutylalanine |
| N—Me-Cys | N-Methyl-Cystine |
| Pen(═O) | Penicillamine sulfoxide |
| hSer(Cl) | Homo-Serine chloride |

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of less common or non-naturally occurring amino acids, unless they are referred to by their full name (e.g. penicillamine, etc.), frequently employed three- or four-character codes are employed for residues thereof. D-amino acids are indicated by the letter "D" before the three letter abbreviation. "h" before the three letter amino acid abbreviations indicates the homo form. For example, "hSer" indicates homoserine.

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-", "$NH_2$" or "Ac" moiety at the amino terminus (N-terminus) of the sequence, and either an "—OH" moiety or an "—$NH_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—$NH_2$" moiety at the C-terminus of the sequence indicates a hydroxy group or an amino group, corresponding to the presence of an acid (COOH) or an amido ($CONH_2$) group at the C-terminus, respectively. In each sequence of the invention, a C-terminal "—OH" moiety may be substituted for a C-terminal "—$NH_2$" moiety, and vice-versa.

Furthermore, $R^1$ can in all sequences be substituted with isovaleric acid, isovaleryl, or an equivalent thereof. In some embodiments, wherein a peptide of the present invention is conjugated to an acidic compound such as, e.g., isovaleric acid, isobutyric acid, valeric acid, and the like, the presence of such a conjugation is referenced in the acid form. So, for example, but not to be limited in any way, instead of indicating a conjugation of isovaleric acid to a peptide by referencing isovaleroyl, in some embodiments, the present application may reference such a conjugation as isovaleric acid.

The term "DRP," as used herein, refers to disulfide rich peptides.

The term "amino acid" or "any amino acid" as used here refers to any and all amino acids, including naturally occurring amino acids (e.g., alpha-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($\beta^3$ and $\beta^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid. Examples of specific unnatural or modified amino acids include, but are not limited to, N-ε-acetyl-L-Lysine (Lys(Ac)), L-1-Napthylalanine (1-Nal), L-2-Napthylalanine (2-Nal), L-Citrulline (Cit), L-Norleucine (Nle), Cyclohexyl-L-alanine (Cha), L-homocyclohexylalanine (hCha), omithine, canavanine, aminoethyl cysteine, and L-homoLeucine (hLeu). It is also understood that amino acid residues that form bonds may be altered somewhat when bonded to each other as compared to when not bonded to each other. Reference to a particular amino acid is meant to encompass that amino acid in both its unbonded and bonded state. For example, the amino acid residue hSer or homoSerine(Cl) in its unbonded form may take the form of 2-aminobutyric acid (Abu) when participating in an intramolecular thioether bond according to the present invention. As such, the names hSer(Cl) and Abu are intended to indicate the same amino acids and may be used interchangeably.

The term "L-amino acid." as used herein, refers to the "L" isomeric form of a peptide, and conversely the term "D-amino acid" refers to the "D" isomeric form of a peptide. The amino acid residues described herein are preferred to be in the "L" isomeric form, however, residues in the "D" isomeric form can be substituted for any L-amino acid residue, as long as the desired functional is retained by the peptide. Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DAsp or D-Asp, DPhe or D-Phe) or in lower case in the conventional one-letter code (e.g., d or f).

The term "$NH_2$," as used herein, can refer to the free amino group present at the amino terminus of a polypeptide. The term "OH," as used herein, can refer to the free carboxy group present at the carboxy terminus of a peptide. Further, the term "Ac," as used herein, refers to Acetyl protection through acylation of the N-terminus of a polypeptide.

The term "carboxy," as used herein, refers to —$CO_2H$.

The term "isostere replacement." as used herein, refers to any amino acid or other analog moiety having chemical and/or structural properties similar to a specified amino acid. In particular embodiments, an "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Illustrative charged amino acid residues include lysine (+), arginine (+), aspartate (−) and glutamate (−). Illustrative polar amino acids include serine, threonine, asparagine, glutamine, histidine and tyrosine. Illustrative hydrophobic amino acids include alanine, valine, leucine, isoleucine, proline, phenylalanine, tryptophane, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. In certain embodiments, an isostere is a derivative of an amino acid, e.g., a derivative having one or more modified side chains as compared to the reference amino acid. In some embodiments, an isostere replacement is a conservative substitution.

The term "cyclized," as used herein, refers to a reaction in which one part of a polypeptide molecule becomes linked to another part of the polypeptide molecule to form a closed ring, such as by forming a disulfide bridge, a thioether bond, or other bond.

The term "pharmaceutically acceptable salt," as used herein, represents salts or zwitterionic forms of the peptides or compounds of the present invention which are water or oil-soluble or dispersible, which are suitable for treatment of diseases without undue toxicity, irritation, and allergic response: which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides, and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA. 2007, and in J. Pharm. Sci. 66: 2 (1977). Also, for a review on suitable salts, see *Handbook of Pharmaceutical Salts: Properties. Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "mammal" refers to any mammalian species such as a human, monkey, primate, mouse, rat, dog, cat, hamster, guinea pig, rabbit, livestock, and the like.

As used herein, a "therapeutically effective amount" of the peptide inhibitor of the invention is meant to describe a sufficient amount of the peptide inhibitor to treat an IL-23/IL-23-related disease, including but not limited to any of the diseases and disorders described herein (for example, to reduce inflammation associated with IBD). In particular embodiments, the therapeutically effective amount will achieve a desired benefit/risk ratio applicable to any medical treatment.

The present invention relates generally to peptides that have IL-23 antagonist activity. In certain embodiments, the present invention relates to various peptides comprising hetero- or homo-monomer subunits, that each form cyclized structures through disulfide or thioether bonds. The cyclized structure of the peptide inhibitors has been shown to increase potency and selectivity of the peptide inhibitors.

Peptide Inhibitors of IL-23

The present invention provides peptide inhibitors that bind to IL-23. In particular embodiments, the peptide inhibitors inhibit the binding of IL-23 to IL-23R and/or inhibit IL-23 signalling. In certain embodiments, the IL-23R is human IL-23R, and the IL-23 is human IL-23. In particular embodiments, the peptide inhibitors selectively inhibit the binding of IL-23 to IL-23R. In particular embodiments, they do not significantly or substantially inhibit binding of IL-23 to IL-12Rβ1. In certain embodiments, they do not significantly or substantially inhibit binding of IL-12 to IL-12Rβ1.

In certain embodiments, peptide inhibitors of the present invention inhibit or reduce binding between IL-23 and IL-23R. In certain embodiments, a peptide inhibitor of the present invention reduces IL-23 binding to IL-23R by at least 20%, at least 30%, at least 40%, at least 50%, at least 60%, at least 70%, at least 80%, or at least 90% as compared to a negative control peptide. Methods of determining binding are known in the art and include ELISA assays, as described in the accompanying Examples.

In certain embodiments, a peptide inhibitor of the present invention has an IC50 of <5 mM, <1 mM, <100 uM, <10 uM, <5 uM, <1 uM, 500 nM to 1000 nM, <500 nM, <250 nM, <100 nM, <50 nM, <25 nM, <10 nM, <5 nM, <2 nM, or <1 nM, e.g., for inhibiting binding of IL-23 to IL-23R (e.g., human IL-23 and human IL-23R). Methods of determining activity are known in the art and include any of those described in the accompanying Examples. In particular embodiments, a peptide inhibitor of the present invention has an IC50 of <1 mM, <100 uM, <10 uM, <5 uM, <1 uM, 500 nM to 1000 nM, <500 nM, <250 nM, <100 nM, <50 nM, <25 nM, <10 nM, <5 nM, <2 nM, <1 nM, or <5 mM, e.g., for inhibiting binding of IL-23 to IL-23R (e.g., human IL-23 and human IL-23R) as determined by an IL23-IL23R Competitive Binding ELISA, e.g., as described herein.

In particular embodiments, a peptide inhibitor of the present invention binds to IL-23. In particular embodiments, a peptide inhibitor selectively inhibits the binding of IL-23 to IL-23R as compared to the binding of IL-23 to IL-12R1. In particular embodiments, the peptide inhibitors inhibit the binding of IL-23 to IL-23R at an IC50 that is at least two times, at least three times, at least four times, at least five times, at least ten times, at least twenty times, at least fifty times, at least one hundred times, at least five hundred times, at least one thousand times, at least five thousand times, or at least ten thousand times lower that the peptide inhibitor's IC50 to inhibit the binding of IL-23 to IL-12Rβ1. In particular embodiments, a peptide inhibitor selectively inhibits the binding of IL-23 to IL-23R as compared to the binding of IL-12 to IL-12Rβ1. In some embodiments, the peptide inhibitors inhibit the binding of IL-23 to IL-23R at an IC50 that is at least two times, at least three times, at least four times, at least five times, at least ten times, at least twenty times, at least fifty times, at least one hundred times, at least five hundred times, at least one thousand times, at least five thousand times, or at least ten thousand times lower that the peptide inhibitor's IC50 to inhibit the binding of IL-12 to IL-12Rβ1.

In particular embodiments, a control peptide is a peptide having a related amino acid sequence (e.g., >80% or >90% sequence identity) as the peptide inhibitor. In particular embodiments, the control peptide differs from the peptide inhibitor of the present invention in that it either does not form a cyclized structure through disulfide or other bonds, or it does not comprise a conjugate for stabilization. In particular embodiments, the only difference between the peptide inhibitor and the control peptide is that the peptide inhibitor comprises one or more amino acid substitutions that introduce one or more amino acid residues (e.g., cysteine residues) into the peptide inhibitor, wherein the introduced residue(s) forms an intramolecular bond with another residue in the peptide inhibitor, e.g., where such bond did not previously exist. In particular embodiments, the only difference between the peptide inhibitor and the control peptide is that the peptide inhibitor comprises one or more amino acid substitutions that introduce one or more cysteine residues into the peptide inhibitor, wherein the introduced cysteine residue(s) forms an intrasulfide disulfide bond with another cysteine residue in the peptide inhibitor. In certain embodiments, a control peptide is an unrelated peptide.

In some embodiments, a peptide inhibitor of the present invention exhibits improved solubility or improved aggregation characteristics as compared to a control peptide. Solubility may be determined via any suitable method known in the art. In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a control peptide. In some embodiments, improved aggregation means the peptide has less aggregation in a given liquid under a given set of conditions than a control peptide.

In some embodiments, the peptide inhibitors of the present invention have increased stability as compared to a control peptide, e.g., greater than two-fold, greater than three-fold, greater than five-fold, greater than ten-fold, greater than twenty-fold greater stability as measured by any suitable method known in the art. In certain embodiments, the peptide inhibitors of the present invention have less degradation, e.g., greater than or about 10% less, greater than or about 20% less, greater than or about 30% less, greater than or about 40 less, or greater than or about 50% less than a control peptide. In some embodiments, degradation stability is determined via any suitable method known in the art. Methods of determining the stability of a peptide are known in the art. In certain embodiments, the stability is determined by measuring the half-life of the peptide. In some embodiments, the half-life is measured in vitro using any suitable method known in the art, e.g., in some embodiments, the stability of a peptide of the present invention is determined by incubating the peptide with pre-warmed human serum (Sigma) at 37° C. Samples are taken at various time points, typically up to 24 hours, and the stability of the sample is analyzed by separating the peptide from the serum proteins and then analyzing for the presence of the peptide of interest using LC-MS.

In particular embodiments, a peptide inhibitor of the present invention exhibits a longer half-life than a reference or control peptide. In particular embodiments, a peptide inhibitor of the present invention has a half-life under a given set of conditions (e.g., temperature, pH) of at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours, at least about 12 hours, at least about 18 hours, at least about 1 day, at least about 2 days, at least about 3 days, at least about 7 days, at least about 10 days, at least about two weeks, at least about three weeks, at least about 1 month, at least about 2 months, at least about 3 months, or more, or any intervening half-life or range in between. In come embodiments, a peptide inhibitor of the present invention has an in vivo serum or plasma half life of at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours, at least about 12 hours, at least about 18 hours, at least about 1 day, at least about 2 days, at least about 3 days, at least about 7 days, at least about 10 days, at least about two weeks, at least about three weeks, at least about 1 month, at least about 2 months, at least about 3 months, or more, or any intervening half-life or range in between. In some embodiments, the half-life of a peptide inhibitor of the present invention is extended due to its conjugation to one or more lipophilic substituent or half-life extension moiety, e.g., any of the lipophilic substituents or half-life extension moieties disclosed herein. In some embodiments, the half-life of a peptide inhibitor of the present invention is extended due to its conjugation to one or more polymeric moieties, e.g., any of the polymeric moieties or half-life extension moieties disclosed herein. In certain embodiments, a peptide inhibitor of the present invention has a half-life as described above under the given set of conditions wherein the temperature is about 25° C., about 4° C., or about 37° C. and the pH is a physiological pH, or a pH about 7.4.

In certain embodiments, peptide inhibitors of the present invention inhibit or reduce IL-23-mediated inflammation. In related embodiments, peptide inhibitors of the present invention inhibit or reduce IL-23-mediated secretion of one or more cytokines, e.g., by binding to IL-23, thus inhibiting IL-23 binding to its cognate cell surface receptor. In particular embodiments, peptide inhibitors of the present invention inhibit or reduce IL-23-mediated activation of Jak2, Tyk2, Stat1, Stat3, Stat4, or Stat5. Methods of determining inhibition of cytokine secretion and inhibition of signaling molecules are known in the art. For example, inhibition of IL-23/IL-23R signaling may be determined by measuring inhibition of phospho-Stat3 levels in cell lysates, as described in herein or in PCT Application Publication No. WO 2016/011208.

The present invention provides various peptide inhibitors that bind or associate with the IL-23, in vitro or in vivo, to inhibit, disrupt or block binding between IL-23 and IL-23R.

The various peptide inhibitors of the invention may be constructed solely of natural amino acids. Alternatively, the peptide inhibitors may include non-natural amino acids including, but not limited to, modified amino acids. In certain embodiments, modified amino acids include natural amino acids that have been chemically modified to include a group, groups, or chemical moiety not naturally present on the amino acid. The peptide inhibitors of the invention may include D-amino acids. Still further, the peptide inhibitors of the invention may include amino acid analogs. One having skill in the art will appreciate that other modified or unnatural amino acids, and various other substitutions of natural amino acids with modified or unnatural amino acids, may be made to achieve similar desired results, and that such substitutions are within the teaching and spirit of the present invention.

The present invention includes any of the peptide inhibitors described herein, e.g., in a free or a salt form.

The present invention also includes peptides having an amino acid sequence of at least 70%, at least 75%, at least 80%, at least 85%, at least 90%, at least 95%, at least 98%, or at least 99% sequence identity to a peptide inhibitor described herein. In particular embodiments, these peptides inhibit binding of IL-23 to IL-23R to a degree at least 50%, at least 60%, at least 70%, at least 80%, or at least 90% as well as the reference peptide inhibitor.

The present invention also includes functional fragments of any of the peptide inhibitors described herein. In particular embodiments, the functional fragment comprises at least 10, at least 15, at least 20, at least 25 or at least 30 contiguous amino acid residues of a peptide inhibitor described herein. In particular embodiments, the functional fragment comprises about 10, about 15, about 20, about 25 or about 30 contiguous amino acid residues of a peptide inhibitor described herein. In particular embodiments, the functional fragment comprises between 10 and 30, between 15 and 30, between 20 and 30, or between 25 and 30 contiguous amino acid residues of a peptide inhibitor described herein. In particular embodiments, these peptides inhibit binding of IL-23 to IL-23R to a degree at least 50%, at least 60%, at least 70%, at least 80%, or at least 90% as well as the reference peptide inhibitor, i.e., the peptide inhibitor from which the functional fragment was derived.

In certain embodiments, a monomer subunit of a peptide inhibitor of the present invention comprises 30-50 amino acid residues. In particular embodiments, a monomer subunit of a peptide inhibitor of the present invention comprises 30-40 or about 34 amino acid residues.

In one embodiment, the present invention includes a peptide inhibitor of an interleukin-23, wherein the peptide inhibitor has the structure of Formula I:

$R^1$—X—$R^2$ (I)

or a pharmaceutically acceptable salt or solvate thereof, wherein $R^1$ is hydrogen, an C1-C6 alkyl, a C6-C12 aryl, a C6-C12 aryl C1-C6 alkyl, a C1-C20 alkanoyl (e.g., methyl, acetyl, formyl, propionyl, benzoyl, trifluoroacetyl, isovaleric acid, isobutyric acid, octanoic acid, octanoyl, lauric acid, lauroyl, hexadecanoic acid, hexadecanoyl, γ-Glu-hexadecanoic acid, or γ-Glu-hexadecanoyl), and including PEGylated versions alone or as spacers of any of the foregoing;

$R^2$ is OH or $NH_2$; and

X is an amino acid sequence comprising the sequence of Formula Ia (SEQ ID NO:38):

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38-X39 (Ia), wherein X1 is absent or any amino acid;

X2 is absent or any amino acid;

X3 is absent or any amino acid;

X4 is absent or any amino acid;

X5 is an amino acid, an aliphatic acid, an alicyclic acid, or a modified 2-methyl aromatic acid, each comprising at least two carbons and capable of forming a thioether or disulfide bond with X34, wherein X5 is optionally selected from Cys, D-Cys, Pen, hCys, D-Pen. N-Me-Cys, D-hCys, hSer, hSer(Cl), 2-chloromethylbenzoic acid, mercapto-propanoic acid, mercapto-butyric acid, 2-chloro-acetic acid, 3-choro-propanoic acid, 4-chloro-butyric acid, and 3-chloro-isobutyric acid, or an isostere of any of the foregoing amino acids;

X6 is any amino acid;

X7 is any amino acid;

X8 is any amino acid;

X9 is any amino acid;

X10 is any amino acid;

X11 is any amino acid;

X12 is any amino acid;

X13 is any amino acid;

X14 is any amino acid;

X15 is any amino acid;

X6 is any amino acid;

X17 is any amino acid;

X18 is any amino acid;

X19 is any amino acid;

X20 is any amino acid;

X21 is any amino acid;

X22 is any amino acid;

X23 is any amino acid;

X24 is any amino acid;

X25 is any amino acid;

X26 is any amino acid;

X27 is any amino acid;

X28 is any amino acid;

X29 is any amino acid;

X30 is any amino acid;

X31 is any amino acid;

X32 is any amino acid;

X33 is any amino acid;

X34 is Cys, D-Cys, Pen, hCys, D-Pen, N-Me-Cys, D-hCys, hSer, or hSer(Cl), or an isostere of any of the foregoing;

X35 is absent or any amino acid;

X36 is absent or any amino acid;

X37 is absent or any amino acid;

X38 is absent or any amino acid; and

X39 is absent or any amino acid.

In particular embodiments, X5 is capable of forming a thioether bond with X34. In particular embodiments, there is a disulfide bond or thioether bond between X5 and X34. In particular embodiments. X34 is Cys. D-Cys. Pen, hCys, D-Pen. N-Me-Cys, D-hCys, hSer, or hSer(Cl). In particular embodiments of Formula (Ia), X5 is an amino acid, an aliphatic acid, an alicyclic acid, or a modified 2-methyl aromatic acid, each comprising at least two carbons and capable of forming a thioether or disulfide bond with X34, wherein X5 is optionally selected from Cys, D-Cys, Pen, hCys. D-Pen, N-Me-Cys, D-hCys, hSer, hSer(Cl), 2-chloromethylbenzoic acid, mercapto-propanoic acid, mercapto-butyric acid, 2-chloro-acetic acid, 3-choro-propanoic acid, 4-chloro-butyric acid, and 3-chloro-isobutyric acid.

In certain embodiments of peptide inhibitors of Formula (I), X is an amino acid sequence comprising the sequence of Formula Ib (SEQ ID NO:23):

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38-X39 (Ib)

wherein

X1 is absent or any amino acid;

X2 is absent or any amino acid;

X3 is absent or any amino acid;

X4 is absent or any amino acid;

X5 is an amino acid, an aliphatic acid, an alicyclic acid, or a modified 2-methyl aromatic acid, each comprising at least two carbons and capable of forming a thioether or disulfide bond with X34, wherein X5 is optionally selected from Cys, D-Cys, Pen, hCys, D-Pen, N-Me-Cys, D-hCys, hSer, hSer(Cl), 2-chloromethylbenzoic acid, mercapto-propanoic acid, mercapto-butyric acid, 2-chloro-acetic acid, 3-choro-propanoic acid, 4-chloro-butyric acid, and 3-chloro-isobutyric acid, or an isostere of any of the foregoing amino acids;

X6 is Leu, Ala, Val, Ile, hLeu, Cha, hCha, Asn or Gln, or an isostere of any of the foregoing;

X7 is any amino acid;

X8 is any amino acid;

X9 is any amino acid;

X10 is any amino acid;

X11 is any amino acid;

X12 is any amino acid;

X13 is Gly, or an isostere thereof;

X14 is Val or Leu, or an isostere of any of the foregoing;

X15 is any amino acid;

X16 is any amino acid;

X17 is any amino acid;

X18 is any amino acid;

X19 is any amino acid;

X20 is Gln, Asn, Glu, Asp or Ser, or an isostere of any of the foregoing;

X21 is any amino acid;

X22 is any amino acid;

X23 is any amino acid;

X24 is any amino acid;

X25 is any amino acid;

X26 is any amino acid;

X27 is any amino acid;

X28 is any amino acid;

X29 is any amino acid;

X30 is any amino acid;

X31 is any amino acid;

X32 is any amino acid;

X33 is any amino acid;

X34 is Cys, D-Cys, Pen, N-Me-Cys, hCys, D-Pen, D-hCys, hSer or hSerCl, or an isostere of any of the foregoing;

X35 is absent or any amino acid;

X36 is absent or any amino acid;

X37 is absent or any amino acid;

X38 is absent or any amino acid; and

X39 is absent or any amino acid.

In particular embodiments of Formula (Ib), X5 is an amino acid, an aliphatic acid, an alicyclic acid, or a modified 2-methyl aromatic acid, each comprising at least two carbons and capable of forming a thioether or disulfide bond with X34, wherein X5 is optionally selected from Cys. D-Cys. Pen, hCys, D-Pen, N-Me-Cys, D-hCys, hSer, hSer (Cl), 2-chloromethylbenzoic acid, mercapto-propanoic acid, mercapto-butyric acid, 2-chloro-acetic acid, 3-choro-propanoic acid, 4-chloro-butyric acid, and 3-chloro-isobutyric acid. In particular embodiments of Formula (Ib). X6 is Leu, Ala, Val, Ile, hLeu, Cha, hCha, Asn or Gln; X13 is Gly; X14 is Val or Leu; X20 is Gln, Asn, Glu. Asp or Ser; and/or X34 is Cys, D-Cys, Pen, N-Me-Cys, hCys, D-Pen, D-hCys, hSer or hSerCl.

In certain embodiments of Formula (Ia) or Formula (Ib), X5 is an amino acid, an aliphatic acid, an alicyclic acid, or a modified 2-methyl aromatic acid, having a side chain with one or two carbons and capable of forming a thioether or disulfide bond with X34. In particular embodiments of Formula (Ia) or Formula (Ib), X5 is capable of forming a thioether bond with X34. In certain embodiments, there is a disulfide or thioether bond between X5 and X34. In particular embodiments, X34 is Cys, D-Cys, Pen, hCys, D-Pen, N-Me-Cys, D-hCys, hSer, or hSer(Cl).

In certain embodiments, the present invention includes a peptide inhibitor comprising the amino acid sequence set forth in Formula (Ia) or Formula (Ib). In particular embodiments, the peptide inhibitor comprises a disulfide or thioether bond between X4 and X35. In certain embodiment, the peptide inhibitor binds to IL-23. In certain embodiments, the peptide inhibitor inhibits binding of IL-23 to IL-23R.

In certain embodiments of peptide inhibitors of Formula (Ia) or Formula (Ib), there is a disulfide bond between X5 and X34. In particular embodiments of Formula (Ia) or Formula (Ib), there is a disulfide bond between X5 and X34; X34 is Cys, D-Cys, Pen, N-Me-Cys, hCys, or D-Pen; and X5 is Cys, D-Cys, N-Me-Cys, Pen, hCys, or D-Pen. In particular embodiments, there is a disulfide bond between X5 and X34, and both X5 and X34 are independently selected from Cys. N-Me-Cys, D-Cys, hCys, Pen. D-Pen, and D-hCys.

In some embodiments of peptide inhibitors of Formula (Ia) or Formula (Ib), there is a thioether bond between X5 and X34. In certain embodiments, there is a thioether bond between X5 and X34; X5 is an amino acid, an aliphatic acid, an alicyclic acid, or a modified 2-methyl aromatic acid, each comprising at least two carbons and capable of forming a thioether bond with X34; and X34 is Cys, N-Me-Cys, D-Cys, hCys, Pen, D-Pen, D-hCys, hSer, or hSerCl. In certain embodiments, there is a thioether bond between X5 and X34; X5 is Cys, N-Me-Cys. D-Cys, hCys, Pen, D-Pen. D-hCys, hSer, or hSerCl: and X34 is Cys, N-Me-Cys, D-Cys, hCys, Pen, D-Pen, D-hCys, hSer, or hSerCl. In certain embodiments of Formula (Ia) or Formula (Ib), X5 is an amino acid, an aliphatic acid, an alicyclic acid, or a modified 2-methyl aromatic acid, having a side chain with one or two carbons and capable of forming a thioether or disulfide bond with X34.

In some embodiments of peptide inhibitors of Formula (Ia) or Formula (Ib), $R^1$ is hydrogen, an C1-C6 alkyl, a C6-C12 aryl, a C6-C12 aryl C1-C6 alkyl, a C1-C20 alkanoyl (optionally selected from methyl, acetyl, formyl, benzoyl, trifluoroacetyl, isovaleric acid, isobutyric acid, octanoic acid, lauric acid, hexadecanoic acid, or γ-Glu-hexadecanoic acid. In some embodiments of peptide inhibitors of Formula (Ia) or Formula (Ib), $R^1$ is hydrogen, an C1-C6 alkyl, a C6-C12 aryl, a C6-C12 aryl C1-C6 alkyl, a C1-C20 alkanoyl (optionally selected from acetyl, formyl, propionyl, benzoyl, trifluoroacetyl, isovaleric acid, isobutyric acid, octanoyl, lauroyl, hexadecanoyl, or γ-Glu-hexadecanoyl). In particular embodiments, the C1-C6 alkyl or C6-C12 aryl C1-C6 alkyl is linear or branched. In particular embodiments, the C1-C20 alkanoyl is any linear alkanoyl or any branched alkanoyl group.

In certain embodiments of Formula (Ia) or Formula (Ib), X5 is hSer, 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, or hSer(Cl). In some embodiments of Formula (Ia) or Formula (Ib), X34 is hSer, hSer(Cl), Cys, Pen, hCys, D-Pen, D-Cys or D-hCys. In particular embodiments of Formula (Ia) or Formula (Ib), X5 is hSer, 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, or hSer(Cl); and X34 is hSer, hSer(Cl), Cys, Pen, hCys, D-Pen, D-Cys or D-hCys; and there is a thioether bond between X5 and X34.

In particular embodiments of Formula (Ia) or Formula (Ib), X1, X2. X3 and/or X4 are any amino acid. In particular embodiments of Formula (Ia) or Formula (Ib), X36, X37, X38 and/or X39 are any amino acid.

In particular embodiments of Formula (Ia) or Formula (Ib), X5 is Cys, X6 is Leu, X13 is Gly, X14 is Val, or X20 is Gln. In particular embodiments, X5 is Cys, X6 is Leu, X13 is Gly, X14 is Val, and X20 is Gln. In certain embodiments of Formula (Ia) or Formula (Ib), two or more, three or more, four or more or five or more of the following are present: X5 is Cys; X6 is Leu; X13 is Gly X14 is Val; and X20 is Gln.

In particular embodiments of Formula (Ia), any of X1-X4, X6-X33, or X35-X29 are Lys. In particular embodiments of Formula (Ib), any of X1-X4, X7-X12, X15-X19, X21-X33, or X35-X39 are Lys.

In various embodiments of any of the peptide inhibitors described herein, including those of Formula (Ia) and Formula (Ib), any of the recited amino acids may be substituted by an isostere thereof.

In particular embodiments of Formula (Ia) or Formula (Ib), the amino acid sequence comprises one or more, two or more, three or more, four or more, five or more, six or more, seven or more, eight or more, nine or more, ten or more, eleven or more, twelve or more, fifteen or more, twenty or more, twenty-five or more, thirty or more, or all of the following:

X1 is Phe, Tyr, Trp, I-Nal, 2-Nal, or an aromatic amino acid, or an isostere of any of the foregoing;

X2 is Asn, Gln, Lys (Ac), Cit, or His, or an isostere of any of the foregoing;

X3 is Met, Ser, Thr, Cys, Asn, Gln, or Nle, or an isostere of any of the foregoing;

X4 is Gln, Asn, Lys (Ac), Cit, or His, or an isostere of any of the foregoing;

X5 is Cys, D-Cys, Pen, hCys, D-Pen, N-Me-Cys, or D-hCys, or an isostere of any of the foregoing;
X6 is Leu, Ala, Val, Ile, hLeu, Cha, hCha, Asn or Gln, or an isostere of any of the foregoing;
X7 is Arg, Leu, Omithine, Canavanine, aminoethyl cysteine, Ala, Val, Ile, hLeu, Cha, hCha, Asn or Gln, or an isostere of any of the foregoing;
X8 is Arg, Leu, Ala, Ornithine, Canavanine, aminoethyl cysteine, Val, Ile, hLeu, Cha, hCha, Asn or Gln, or an isostere of any of the foregoing;
X9 is Met, Phe, Ala, Ser, Thr, Cys, Asn, Gln, Nle, Tyr, Trp, 1-Nal, 2-Nal, an aromatic amino acid, Val, Ile, hLeu, Cha, hCha, Asn or Gln, or an isostere of any of the foregoing;
X10 is Ser, Tyr, Ala, Thr, Cys, Asn, Gln, Nle, Trp, I-Nal, 2-Nal, an aromatic amino acid, Val, Ile, hLeu, Cha, hCha, Asn or Gln, or an isostere of any of the foregoing;
X11 is Glu, Trp, Ser, Asp, Asn, or Gln, or an isostere of any of the foregoing;
X12 is Ala, Val, Ile, hLeu, Cha, hCha, Asn or Gln, or an isostere of any of the foregoing;
X13 is Gly, Ala, Val, Ile, hLeu, Cha, hCha, Asn or Gln, or an isostere of any of the foregoing;
X14 is Val, Leu, Val, Ile, hLeu, Cha, hCha, Asn or Gln, or an isostere of any of the foregoing;
X15 is Asp, Asn, Glu, or Gln, or an isostere of any of the foregoing;
X16 is Pro, Ala, Leu, Ile, Val, hLeu, Cha, hCha, Asn or Gln, or an isostere of any of the foregoing;
X17 is Asn, Gln, Lys (Ac), Cit, His, or an isostere of any of the foregoing;
X18 is Leu, Ala, Val, Ile, hLeu, Cha, hCha, Asn or Gln, or an isostere of any of the foregoing;
X19 is Asn, Ala, Gln, Lys (Ac), Cit, or His, or an isostere of any of the foregoing;
X20 is Gln, Glu, or Asp, or an isostere of any of the foregoing;
X21 is Glu or Asp, or an isostere of any of the foregoing;
X22 is Gln, Asp, Glu, or Asn, or an isostere of any of the foregoing;
X23 is Arg, Ala, Leu, Ala, Omithine, Canavanine, aminoethyl cysteine, Val, Ile, hLeu, Cha, hCha, Asn or Gln, or an isostere of any of the foregoing;
X24 is Trp, Asn, Ala, Val, Ile, hLeu, Cha, hCha, Asn or Gln, or an isostere of any of the foregoing;
X25 is Ala, Ile, Val, Ile, hLeu, Cha, hCha, Asn or Gln, or an isostere of any of the foregoing;
X26 is Lys or Arg, or an isostere of any of the foregoing;
X27 is Ile, Ala, Val, hLeu, Cha, hCha, Asn or Gln, or an isostere of any of the foregoing;
X28 is Lys, Ala, Ile, Val, hLeu, Cha, hCha, Asn or Gln, or an isostere of any of the foregoing;
X29 is Ser, Thr, Cys, Asn, Gln, Nle, or Trp, or an isostere of any of the foregoing;
X30 is Ile, Phe, Val, hLeu, Cha, hCha, Asn or Gln; Tyr, Trp, 1-Nal, 2-Nal, or an aromatic amino acid, or an isostere of any of the foregoing;
X31 is Met, Arg, Ser, Thr, Cys, Asn, Gln, or Nle, or an isostere of any of the foregoing;
X32 is Asp or Glu, or an isostere of any of the foregoing;
X33 is Asp, Gly, Leu, Ala, Ile, Val, hLeu, Cha, hCha, Asn or Gln, or an isostere of any of the foregoing; and
X34 is Cys, D-Cys, Pen, hCys, D-Pen, N-Me-Cys, or D-hCys, or an isostere of any of the foregoing.

In particular embodiments of Formula (Ia) or Formula (Ib), the amino acid sequence comprises one or more, two or more, three or more, four or more, five or more, six or more, seven or more, eight or more, nine or more, ten or more, eleven or more, twelve or more, fifteen or more, twenty or more, twenty-five or more, thirty or more, or all of the following:

X1 is Phe, Tyr, Trp, 1-Nal, 2-Nal, or an aromatic amino acid;
X2 is Asn, Gln, Lys (Ac), Cit, or His;
X3 is Met, Ser, Thr, Cys, Asn, Gln, or Nle;
X4 is Gln, Asn, Lys (Ac), Cit, or His;
X5 is Cys, D-Cys, Pen, hCys, D-Pen, N-Me-Cys, or D-hCys;
X6 is Leu, Ala, Val, Ile, hLeu, Cha, hCha, Asn or Gln;
X7 is Arg, Leu, Ornithine, Canavanine, aminoethyl cysteine, Ala, Val, Ile, hLeu, Cha, hCha, Asn or Gln;
X8 is Arg, Leu, Ala, Ornithine, Canavanine, aminoethyl cysteine, Val, Ile, hLeu, Cha, hCha, Asn or Gln;
X9 is Met, Phe, Ala, Ser, Thr, Cys, Asn, Gln, Nle, Tyr, Trp, 1-Nal, 2-Nal, an aromatic amino acid, Val, Ile, hLeu, Cha, hCha, Asn or Gln;
X10 is Ser, Tyr. Ala, Thr, Cys, Asn, Gln, Nle, Trp, 1-Nal, 2-Nal, an aromatic amino acid, Val, Ile, hLeu, Cha, hCha, Asn or Gln;
X11 is Glu, Trp, Ser. Asp, Asn, or Gln;
X12 is Ala. Val, Ile, hLeu, Cha, hCha, Asn or Gln;
X13 is Gly, Ala, Val, Ile, hLeu, Cha, hCha, Asn or Gln;
X14 is Val, Leu, Val, Ile, hLeu, Cha, hCha, Asn or Gln;
X15 is Asp, Asn, Glu, or Gln;
X16 is Pro, Ala, Leu, Ile, Val, hLeu, Cha, hCha, Asn or Gln
X17 is Asn, Gln, Lys (Ac), Cit, His;
X18 is Leu, Ala, Val, Ile, hLeu, Cha, hCha, Asn or Gln;
X19 is Asn, Ala, Gln, Lys (Ac), Cit, or His;
X20 is Gln, Glu, or Asp;
X21 is Glu or Asp;
X22 is Gln, Asp, Glu, or Asn;
X23 is Arg, Ala, Leu, Ala, Ornithine, Canavanine, aminoethyl cysteine, Val, Ile, hLeu, Cha, hCha, Asn or Gln;
X24 is Trp, Asn, Ala, Val, Ile, hLeu, Cha, hCha, Asn or Gln;
X25 is Ala, Ile, Val, Ile, hLeu, Cha, hCha, Asn or Gln;
X26 is Lys or Arg;
X27 is Ile, Ala, Val, hLeu, Cha, hCha, Asn or Gln;
X28 is Lys, Ala, Ile. Val, hLeu, Cha, hCha, Asn or Gln;
X29 is Ser, Thr, Cys, Asn, Gln, Nle, or Trp;
X30 is Ile, Phe, Val, hLeu, Cha, hCha, Asn or Gln; Tyr, Trp, 1-Nal, 2-Nal, or an aromatic amino acid;
X31 is Met. Arg, Ser, Thr, Cys, Asn, Gln, or Nle, or an isostere of any of the foregoing;
X32 is Asp or Glu;
X33 is Asp, Gly, Leu, Ala, Ile, Val, hLeu, Cha, hCha, Asn or Gln; and
X34 is Cys, D-Cys. Pen, hCys. D-Pen, N-Me-Cys, or D-hCys.

In particular embodiments of Formula (Ia) or Formula (Ib), the amino acid sequence comprises one or more, two or more, three or more, four or more, five or more, six or more, seven or more, eight or more, nine or more, ten or more, eleven or more, twelve or more, fifteen or more, twenty or more, twenty-five or more, thirty or more, or all of the following:

X1 is Phe;
X2 is Asn;
X3 is Met;
X4 is Gln;
X5 is Cys;
X6 is Leu;

X7 is Arg or Leu;
X8 is Arg, Leu or Ala;
X9 is Met, Phe or Ala;
X10 is Ser, Tyr or Ala;
X11 is Glu, Trp or Ser;
X12 is Ala;
X13 is Gly or Ala;
X14 is Val or Leu;
X15 is Asp or Asn;
X16 is Pro or ala;
X17 is Asn;
X18 is Leu;
X19 is Asn or Ala;
X20 is Gln, Asn, Glu, Asp or Ser, optionally Gln or Glu;
X21 is Glu;
X22 is Gln or Asp;
X23 is Arg or Ala;
X24 is Trp, Asn or Ala;
X25 is Ala;
X26 is Lys or Arg;
X27 is Ile or Ala;
X28 is Lys or Ala;
X29 is Ser;
X30 is Ile or Phe;
X31 is Met or Arg;
X32 is Asp;
X33 is Asp. Gly or Leu; or
X34 is Cys.

In particular embodiments of Formula (Ia) or Formula (Ib), the amino acid sequence comprises one or more, two or more, three or more, four or more, five or more, six or more, seven or more, eight or more, nine or more, ten or more, eleven or more, twelve or more, fifteen or more, twenty or more, twenty-five or more, thirty or more, or all of the following:

X1 is Phe, or an isostere thereof;
X2 is Asn, or an isostere thereof;
X3 is Met, or an isostere thereof;
X4 is Gln, or an isostere thereof;
X5 is Cys, or an isostere thereof;
X6 is Leu or an isostere thereof;
X7 is Arg or Leu, or an isostere of any of the foregoing;
X8 is Arg, Leu or Ala, or an isostere of any of the foregoing;
X9 is Met, Phe or Ala, or an isostere of any of the foregoing;
X10 is Ser. Tyr or Ala, or an isostere of any of the foregoing;
X11 is Glu, Tip or Ser, or an isostere of any of the foregoing;
X12 is Ala, or an isostere thereof;
X13 is Gly or Ala, or an isostere of any of the foregoing;
X14 is Val or Leu, or an isostere of any of the foregoing;
X15 is Asp or Asn, or an isostere of any of the foregoing;
X16 is Pro or Ala, or an isostere of any of the foregoing;
X17 is Asn, or an isostere thereof;
X18 is Leu, or an isostere thereof;
X19 is Asn or Ala, or an isostere of any of the foregoing;
X20 is Gln, Asn, Glu, Asp or Ser, or an isostere of any of the foregoing, optionally Gln or Glu;
X21 is Glu, or an isostere thereof;
X22 is Gln or Asp, or an isostere of any of the foregoing;
X23 is Arg or Ala, or an isostere of any of the foregoing;
X24 is Trp, Asn or Ala, or an isostere of any of the foregoing;
X25 is Ala, or an isostere thereof;
X26 is Lys or Arg, or an isostere of any of the foregoing;
X27 is Ile or Ala, or an isostere of any of the foregoing;
X28 is Lys or Ala, or an isostere of any of the foregoing;
X29 is Ser, or an isostere thereof;
X30 is Ile or Phe, or an isostere of any of the foregoing;
X31 is Met or Arg, or an isostere of any of the foregoing;
X32 is Asp, or an isostere thereof;
X33 is Asp. Gly or Leu, or an isostere of any of the foregoing; or
X34 is Cys, or an isostere thereof.

In particular embodiments of Formula (Ia) or (Ib): X1, X2, X3 and X4 are absent or any amino acid; X5 is Cys, D-Cys, Pen or hCys; X6 is Leu, Ala, Val, Ile, hLeu, Cha, hCha, Asn or Gln: X7, X8, X9, X10, X11 and X12 are any amino acid; X13 is Gly; X14 is Val or Leu; X15, X16. X17, X18 and X19 are any amino acid; X20 is Gln, Asn, Glu, Asp or Ser; X21, X22, X23, X24, X25, X26, X27, X28, X29, X30, X31, X32, and X33 are any amino acid; X34 is Cys, D-Cys, Pen or hCys; and X35, X36, X37, X38 and X39 are absent or any amino acid. In particular embodiments, X5 and X34 are Cys. In particular embodiments, there is a disulfide bond between X5 and X34.

In particular embodiments of Formula (Ia) or Formula (Ib), the amino acid sequence comprises one or more, two or more, three or more, four or more, five or more, six or more, seven or more, eight or more, nine or more, ten or more, eleven or more, twelve or more, fifteen or more, twenty or more, twenty-five or more, or thirty or more of the following:

X1 is Phe;
X2 is Asn;
X3 is Met;
X4 is Gln;
X5 is Cys;
X6 is Leu;
X7 is Arg;
X8 is Arg;
X9 is Met;
X10 is Ser;
X11 is Trp;
X12 is Ala;
X13 is Gly;
X14 is Val;
X15 is Asp;
X16 is Pro
X17 is Asn;
X18 is Leu;
X19 is Asn;
X20 is Gln;
X21 is Glu;
X22 is Gln;
X23 is Arg;
X24 is Trp;
X25 is Ala;
X26 is Lys;
X27 is Ile;
X28 is Lys;
X29 is Ser;
X30 is Ile;
X31 is Met;
X32 is Asp;
X33 is Asp; or
X34 is Cys.

In certain embodiments of any of the peptide inhibitors disclosed herein, $R^1$ is acetyl (Ac).

In certain embodiments of any of the peptide inhibitors disclosed herein, $R^2$ is $NH_2$.

In particular embodiments, the present invention includes a peptide inhibitor comprising a consensus amino acid sequence of:

(SEQ ID NO: 24)
B1-B2-Z-Z-Z-Z-Z-B3-B4-Z-Z-Z-Z-B5-Z-Z-Z-Z-Z-Z-Z-Z-Z-Z-Z-B6;

(SEQ ID NO: 25)
B1-B2-Z-Z-Z-Z-Z-B3-B4-Z-Z-Z-Z-B5-Z-Z-Z-Z-Z-Z-Z-Z-Z-Z-B6;

(SEQ ID NO: 26)
B1-B2-Z-Z-Z-Z-Z-B3-B4-Z-Z-Z-Z-B5-Z-Z-Z-Z-Z-Z-Z-Z-Z-B6;

(SEQ ID NO: 27)
B1-B2-Z-Z-Z-Z-Z-B3-B4-Z-Z-Z-Z-B5-Z-Z-Z-Z-Z-Z-Z-Z-B6;

(SEQ ID NO: 28)
B1-B2-Z-Z-Z-Z-Z-B3-B4-Z-Z-Z-Z-B5-Z-Z-Z-Z-Z-Z-Z-B6;

(SEQ ID NO: 29)
B1-B2-Z-Z-Z-Z-Z-B3-B4-Z-Z-Z-Z-B5-Z-Z-Z-Z-Z-Z-B6;

(SEQ ID NO: 30)
B1-B2-Z-Z-Z-Z-Z-B3-B4-Z-Z-Z-Z-B5-Z-Z-Z-Z-Z-B6;

(SEQ ID NO: 31)
B1-B2-Z-Z-Z-Z-Z-B3-B4-Z-Z-Z-Z-B5-Z-Z-Z-Z-B6;

(SEQ ID NO: 32)
B1-B2-Z-Z-Z-Z-Z-B3-B4-Z-Z-Z-Z-B5-Z-Z-Z-Z-B6;

(SEQ ID NO: 33)
B1-B2-Z-Z-Z-Z-Z-B3-B4-Z-Z-Z-Z-B5-Z-Z-Z-B6;

(SEQ ID NO: 34)
B1-B2-Z-Z-Z-Z-Z-B3-B4-Z-Z-Z-Z-B5-Z-Z-B6;

(SEQ ID NO: 35)
B1-B2-Z-Z-Z-Z-Z-B3-B4-Z-Z-Z-Z-B5-Z-Z-B6;

(SEQ ID NO: 36)
B1-B2-Z-Z-Z-Z-Z-B3-B4-Z-Z-Z-Z-B5-Z-B6;
or (SEQ ID NO: 37)
B1-B2-Z-Z-Z-Z-Z-B3-B4-Z-Z-Z-Z-B5-B6, wherein Z is any amino acid;

B1 is an amino acid, an aliphatic acid, an alicyclic acid, or a modified 2-methyl aromatic acid comprising at least two carbons and capable of forming a thioether or disulfide bond with B6, wherein B1 is optionally selected from Cys, D-Cys, h-Cys, Pen, D-Pen, hSer, hSer(Cl), N-Me-Cys, and D-hCys, and isosteres thereof;

B2 is Leu, Ala, Val, Ile, hLeu, Cha, hCha, Asn or Gln, or an isostere of any of the foregoing;

B3 is Gly or an isostere thereof;

B4 is Val or Leu, or an isostere of any of the foregoing;

B5 is Gln, Asn, Glu, Asp or Ser, or an isostere of any of the foregoing; and

B6 is Cys, N-Me-Cys, D-Cys, hCys, Pen, D-Pen, D-hCys, hSer, or hSerCl, or an isostere of any of the foregoing.

In particular embodiments, B1 is an amino acid, an aliphatic acid, an alicyclic acid, or a modified 2-methyl aromatic acid comprising at least two carbons and capable of forming a thioether or disulfide bond with B6, wherein B1 is optionally selected from Cys, D-Cys, h-Cys, Pen. D-Pen, hSer, hSer(Cl), N-Me-Cys, and D-hCys; B2 is Leu, Ala, Val, Ile, hLeu, Cha, hCha, Asn or Gln: B3 is Gly: B4 is Val or Leu: B5 is Gln, Asn, Glu, Asp or Ser; and B6 is Cys, N-Me-Cys, D-Cys, hCys, Pen, D-Pen. D-hCys, hSer, or hSerCl In certain embodiments, two cysteine residues within the peptide inhibitor are linked by an intramolecular disulfide bond. In certain embodiments. B1 and B6 form a disulfide bond. In certain embodiments, B1 is Cys, D-Cys, Pen, N-Me-Cys, hCys, or D-Pen; B6 is Cys, D-Cys, Pen, N-Me-Cys, hCys, or D-Pen; and there is a disulfide bond between B1 and B6.

In some embodiments, there is a thioether bond between B1 and B6. In certain embodiments, there is a thioether bond between B1 and B6: B1 is an amino acid, an aliphatic acid, an alicyclic acid, or a modified 2-methyl aromatic acid having a side chain, each comprising at least two carbons and capable of forming a thioether bond with B6; and B6 is Cys, N-Me-Cys, D-Cys, hCys, Pen. D-Pen, D-hCys, hSer, or hSerCl. In certain embodiments, B1 is an amino acid, an aliphatic acid, an alicyclic acid, or a modified 2-methyl aromatic acid, having a side chain with one or two carbons and capable of forming a thioether or disulfide bond with X34; and B6 is Cys, N-Me-Cys, D-Cys, hCys. Pen, D-Pen, D-hCys, hSer, or hSerCl.

In certain embodiments, B1 is hSer, 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, or hSer(Cl). In some embodiments, B6 is hSer, hSer(Cl), Cys, Pen, hCys, D-Pen, D-Cys or D-hCys. In particular embodiments, B1 is hSer, 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, or hSer (Cl): and B6 is hSer, hSer(Cl), Cys, Pen, hCys, D-Pen, D-Cys or D-hCys; and there is a thioether or disulfide bond between B1 and B6.

In particular embodiments, the peptide inhibitor comprises an N-terminal Ac and/or a C-terminal $NH_2$ or OH group. In particular embodiments, the peptide inhibitor comprises a disulfide bond between B1 and B6. In particular embodiments, the peptide inhibitor comprises one or more additional N-terminal and/or C-terminal amino acid residues.

The present invention also includes any of the peptide inhibitors described herein in either a free or a salt form. Thus, embodiments of any of the peptide inhibitors described herein (and related methods of use thereof) include a pharmaceutically acceptable salt of the peptide inhibitor.

The present invention also contemplates dimers comprising two or more of any of the monomer peptide inhibitors described herein. The two peptide inhibitors may be dimerized via a linker bound to both monomer peptide inhibitors. In particular embodiments, the linker binds to each of the monomer peptide inhibitors at its N-terminus, C-terminus, or an internal amino acid residue. A variety of linkers are known and available in the art, which may be used to form dimer peptide inhibitors according to the present invention.

In certain embodiments, peptide inhibitors of the present invention, comprise one or more conjugated chemical substituents, such as lipophilic substituents and polymeric moieties, collectively referred to herein as half-life extension moieties. Without wishing to be bound by any particular theory, it is believed that the lipophilic substituent binds to albumin in the bloodstream, thereby shielding the peptide inhibitor from enzymatic degradation, and thus enhancing its half-life. In addition, it is believed that polymeric moieties enhance half-life and reduce clearance in the bloodstream, and in some cases enhance permeability through the epithelium and retention in the lamina propria. Moreover, it is also surmised that these substituents in some cases may enhance permeability through the epithelium and retention in the lamina propria. The skilled person will be well aware of suitable techniques for preparing the compounds employed in the context of the invention. For examples of non-limiting suitable chemistry, see, e.g., WO98/08871, WO00/55184, WO00/55119, Madsen et al (J. Med. Chem. 2007, 50, 6126-32), and Knudsen et al. 2000 (J. Med Chem. 43, 1664-1669, incorporated herein by reference in their entirety).

In certain embodiments, a peptide inhibitor of the present invention, comprising a conjugated half-life extension moiety, has an increased serum half-life following intravenous or subcutaneous administration as compared to the same analogue but lacking the conjugated half-life extension moiety. In particular embodiments, the serum half-life of a peptide inhibitor of the present invention following an intravenous or subcutaneous administration is at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours, at least about 12 hours, at least about 18 hours, at least about 1 day, at least about 2 days, at least about 3 days, at least about 7 days, at least about 10 days, at least about two weeks, at least about three weeks, at least about 1 month, or more.

In some embodiments, the stability of a peptide inhibitor is measured in vivo using any suitable method known in the art, e.g., in some embodiments, the stability of a peptide inhibitor is determined in vivo by administering the peptide or peptide dimer to a subject such as a human or any mammal (e.g., mouse) and then samples are taken from the subject via blood draw at various time points, typically up to 24 hours. Samples are then analyzed as described above in regard to the in vitro method of measuring half-life.

In one embodiment, the side chains of one or more amino acid residues (e.g., Lys residues) in a peptide inhibitor of the invention may be conjugated (e.g., covalently attached) to a lipophilic substituent and/or a half-life extension moiety. The lipophilic substituent and/or half-life extension moiety may be covalently bonded to an atom in the amino acid side chain, or alternatively may be conjugated to the amino acid side chain via one or more spacers. The spacer, when present, may provide spacing between the peptide analogue and the lipophilic substituent.

In certain embodiments, the lipophilic substituent and/or the half-life extension moiety may comprise a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A half-life extension moiety and/or a lipophilic substituent may be conjugated to any amino acid side chain in a peptide inhibitor of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asp, Glu, His, Lys, Arg, Ser, Thr, Tyr, or Cys. In certain embodiments, the half-life extension moiety and/or the lipophilic substituent is conjugated to Lys.

In particular embodiments, the half-life extension moiety is selected from one of those shown below:

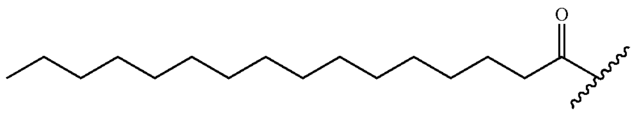

C16

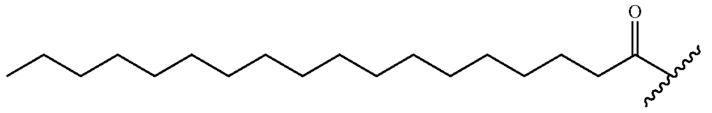

C18

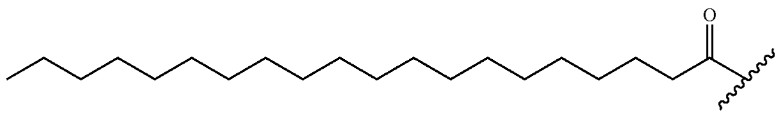

C20

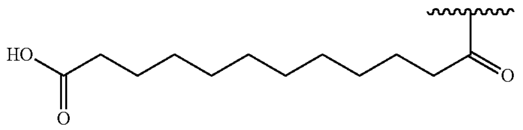

C12 diacid

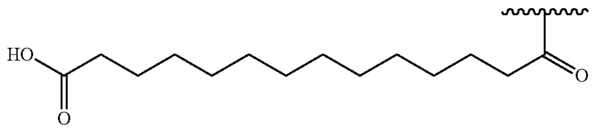

C14 diacid

-continued
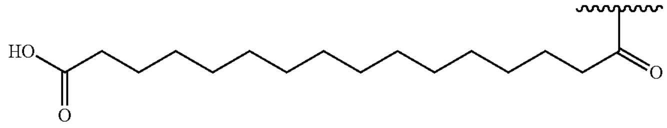
C16 diacid
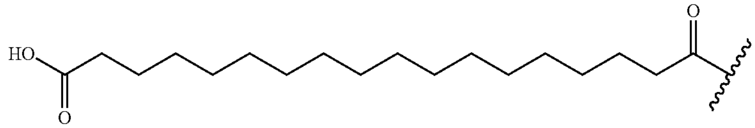
C18 diacid
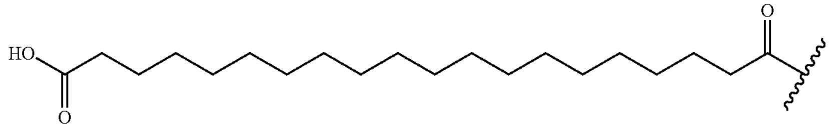
C20 diacid
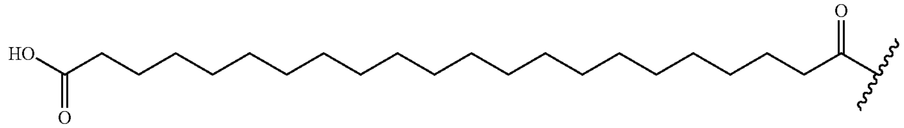
C22 diacid
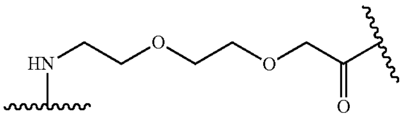
OEG
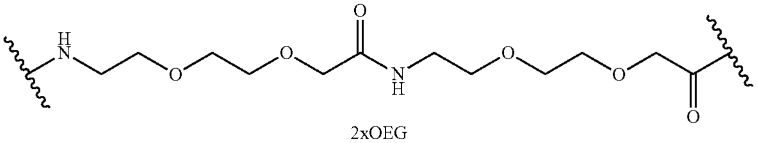
2xOEG
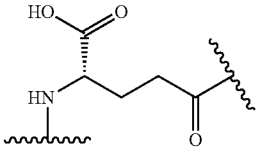
gGlu
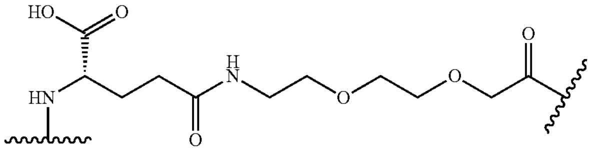
γGlu-OEG
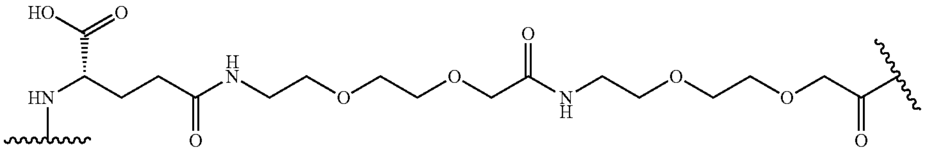
γGlu-2xOEG
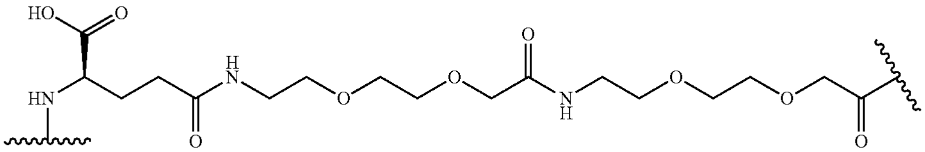
DγGlu-2xOEG
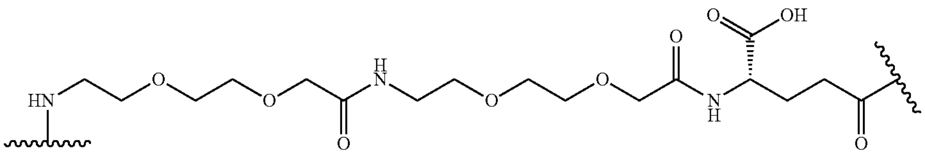
2xOEG-γGlu
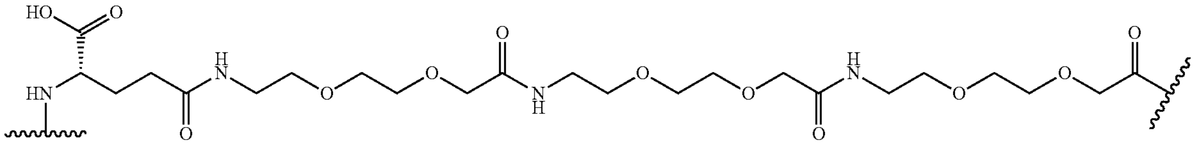
γGlu-3xOEG -continued

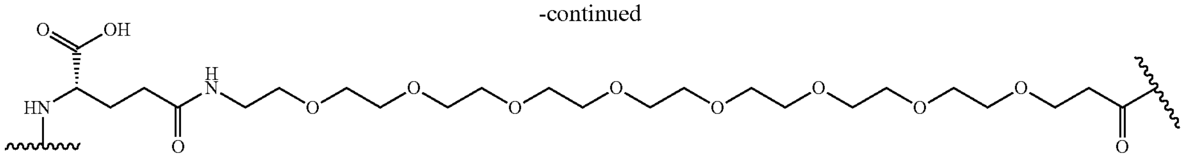

γGlu-8PEG

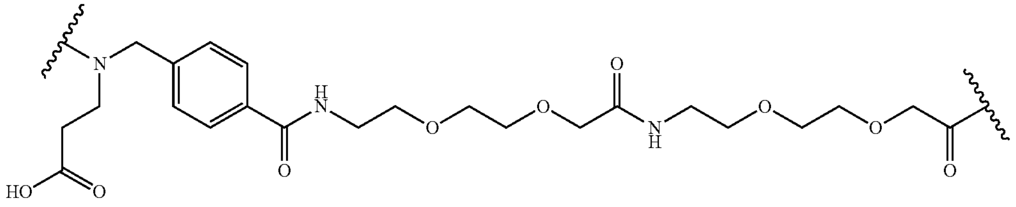

benzyl-βAla-2xOEG

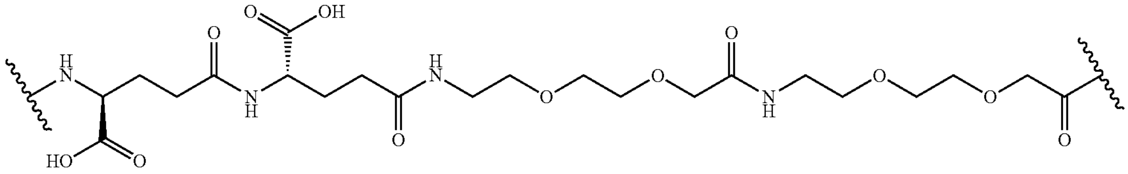

2xγGlu-2xOEG

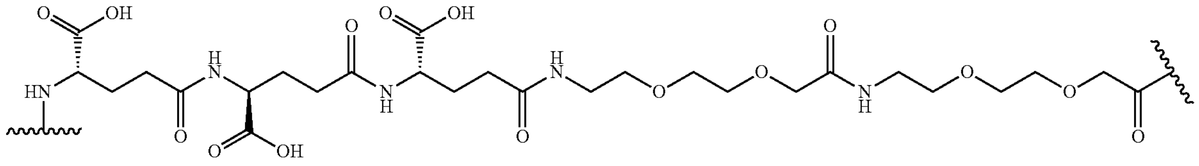

3xγGlu-2xOEG

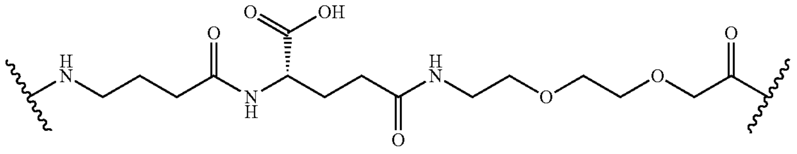

Abu-γGlu-OEG

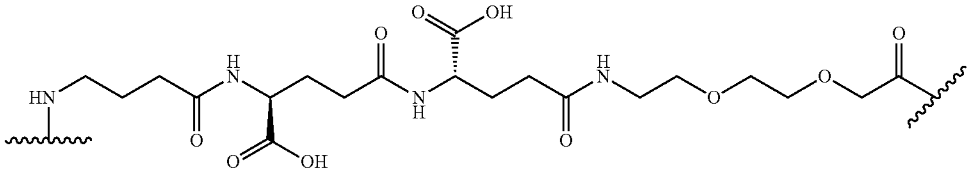

Abu-2γGlu-OEG

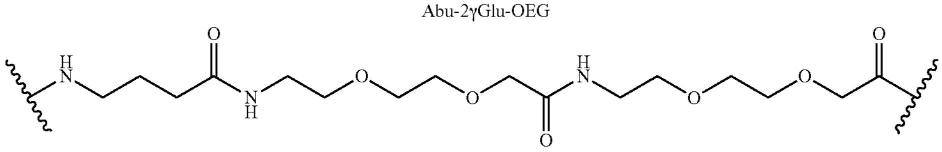

Abu-2xOEG

In particular embodiments, the half-life extension moiety is a PEG. As used herein, "Polyethylene glycol" or "PEG" is a polyether compound of general formula H—(O—CH2-CH2)$_n$-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or copolymers of PEG, a monomethyl-substituted polymer of PEG (mPEG), or polyoxyethylene glycerol (POG). See, for example, Int. J. Hematology 68:1 (1998), Bioconjugate Chem. 6:150 (1995); and Crit. Rev. Therap. Drug Carrier Sys. 9:249 (1992). Also encompassed are PEGs that are prepared for purpose of half-life extension, for example, mono-activated, alkoxy-terminated polyalkylene oxides (POAs) such as mono-methoxy-terminated polyethyelene glycols (mPEGs); bis activated polyethylene oxides (glycols) or other PEG derivatives are also contemplated. Suitable polymers will vary substantially by weights ranging from about 200 Daltons to about 80,000 Daltons are usually selected for the purposes of the present invention. In certain embodiments, PEGs having molecular weights from 200 Daltons to 80,000 Daltons are used. Different forms of PEG may also be used, depending on the initiator used for the polymerization process—a common initiator is a monofunctional methyl ether PEG, or methoxypoly(ethylene glycol), abbreviated mPEG. PEGs disclosed herein include both branched and linear PEGs.

Lower-molecular-weight PEGs are also available as pure oligomers, referred to as monodisperse, uniform, or discrete. These are used in certain embodiments of the present invention.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of covalently coupling a PEG structure to the peptide inhibitor of the invention, which is then referred to as a "PEGylated peptide inhibitor". In certain embodiments, the PEG of the PEGylated side chain is a PEG with a molecular weight from about 200 to about 80,000. In some embodiments, a spacer of a peptide of Formula I is PEGylated. In certain embodiments, the PEG of a PEGylated spacer is PEG3, PEG4, PEG5, PEG6. PEG7, PEG8, PEG9, PEG10, or PEG11. In certain embodiments, the PEG of a PEGylated spacer is PEG3 or PEG8.

Other suitable polymeric moieties that may be used include poly-amino acids such as poly-lysine, poly-aspartic acid and poly-glutamic acid (see for example Gombotz, et al. (1995), Bioconjugate Chem., vol. 6: 332-351: Hudecz, et al. (1992), Bioconjugate Chem., vol. 3, 49-57 and Tsukada, et al. (1984), J. Natl. Cancer Inst., vol. 73: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a peptide inhibitor of the invention may comprise two or more such half-life extension moieties or polymeric moieties, in which case the total molecular weight of all such moieties will generally fall within the ranges provided above.

In some embodiments, the half-life extension moiety or polymeric moiety may be coupled (by covalent linkage) to an amino, carboxyl or thiol group of an amino acid side chain. Certain examples are the thiol group of Cys residues and the epsilon amino group of Lys residues, and the carboxyl groups of Asp and Glu residues may also be involved.

In particular embodiments, a peptide inhibitor of the present invention comprises a half-life extension moiety, which may be selected from but is not limited to the following: Ahx-Palm, PEG2-Palm, PEG11-Palm, isoGlu-Palm, dapa-Palm, isoGlu-Lauric acid, isoGlu-Mysteric acid, and isoGlu-Isovaleric acid.

In particular embodiments, a peptide inhibitor comprises a half-life extension moiety having the structure shown below, wherein n=0 to 24 or n=14 to 24:

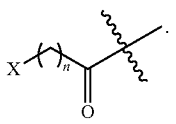

n = 0 to 24
X = $CH_3$, $CO_2H$, $NH_2$, OH

In certain embodiments, a peptide inhibitor of the present invention comprises a conjugated half-life extension moiety shown in Table 4.

TABLE 4

| Illustrative Half-Life Extension Moieties | |
|---|---|
| # | Half-Life Extension Moieties |
| C1 | 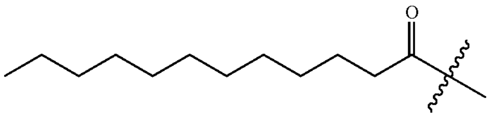 C12 (Lauric acid) |
| C2 | 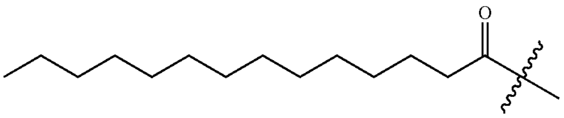 C14 (Mysteric acid) |

TABLE 4-continued
| Illustrative Half-Life Extension Moieties | |
|---|---|
| # | Half-Life Extension Moieties |
| C3 | 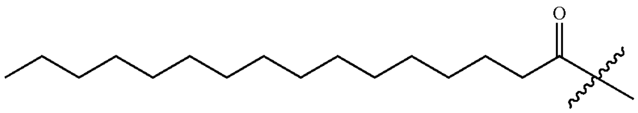 C16 (Palm or Palmitic acid) |
| C4 | 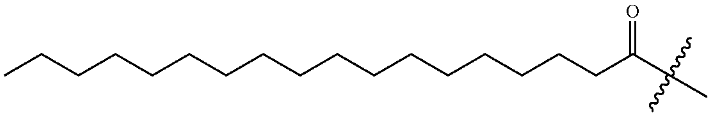 C18 (Stearic acid) |
| C5 | 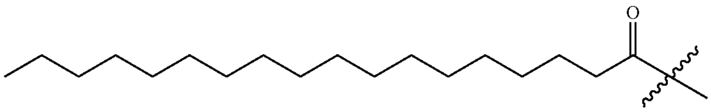 C20 |
| C6 | 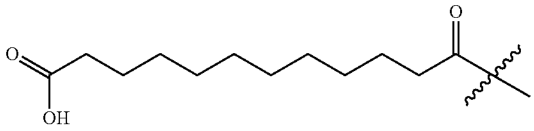 C12 diacid |
| C7 | 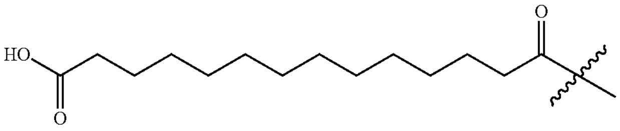 C14 diacid |
| C8 | 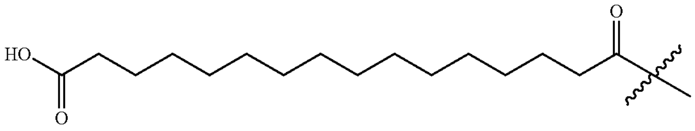 C16 diacid |
| C9 | 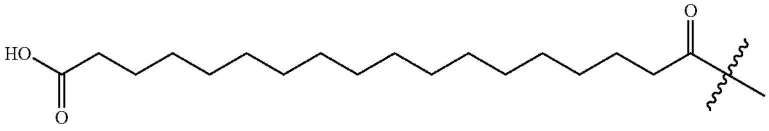 C18 diacid |
| C10 | 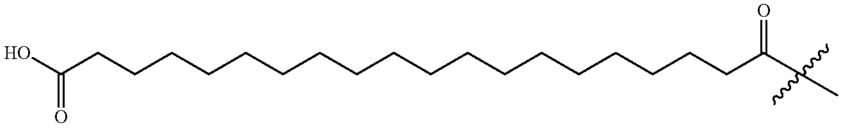 C20 diacid |

TABLE 4-continued

| Illustrative Half-Life Extension Moieties | |
|---|---|
| # | Half-Life Extension Moieties |
| C11 | 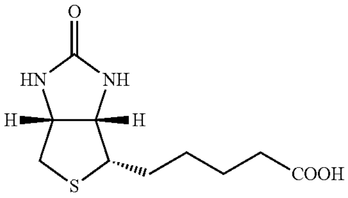<br>Biotin |
| C12 | 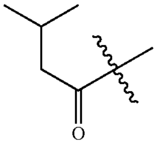<br>Isovaleric acid |
| C13 | PolyEthylene Glycol Mol wt of 10,000 Da<br>(PEG10K)<br>(branched and/or linear) |
| C14 | PolyEthylene Glycol Mol wt of 20,000 Da<br>(PEG20K)<br>(branched and/or linear) |
| C15 | PolyEthylene Glycol Mol wt of 40,000 Da<br>(PEG40K)<br>(branched and/or linear) |
| C16 | PolyEthylene Glycol Mol wt of 60,000 Da<br>(PEG60K)<br>(branched and/or linear) |
| C17 | PolyEthylene Glycol Mol wt of 80,000 Da<br>(PEG80K)<br>(branched and/or linear) |
| C18 | PolyEthylene Glycol<br>(branched and/or linear) |

In certain embodiments, a half-life extension moiety is conjugated directly to a peptide inhibitor, while in other embodiments, a half-life extension moiety is conjugated to a peptide inhibitor peptide via a linker moiety, e.g., any of those depicted in Table 1 or 5.

TABLE 5

| Illustrative Linker Moieties | |
|---|---|
| # | Linker Moiety |
| L1 | 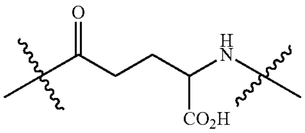<br>IsoGlu |
| L2 | 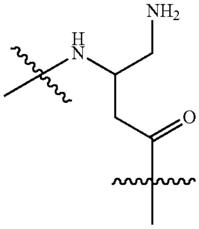<br>Dapa |

TABLE 5-continued
| Illustrative Linker Moieties | |
|---|---|
| # | Linker Moiety |
| L3 | 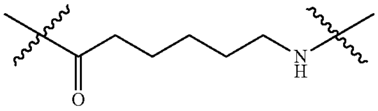 Ahx |
| L4 | Lipidic based linkers: 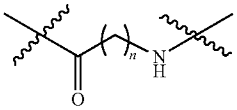 n = 1 to 24 |
| L5 | 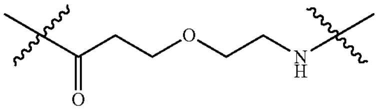 PEG1 |
| L6 | 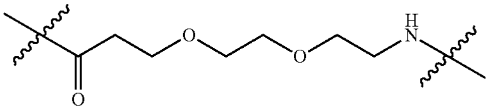 PEG2 |
| L7 | 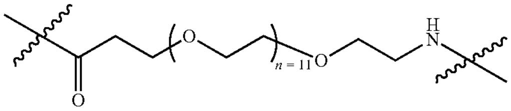 PEG11 (40 atoms) also known as PEG 12 |
| L8 | 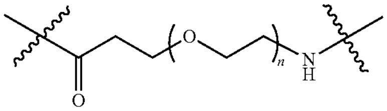 n = 1 to 25 PEG based linkers |
| L9 | 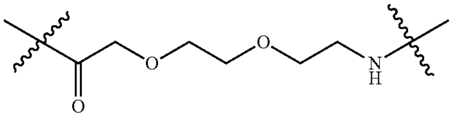 OEG |
| L10 | 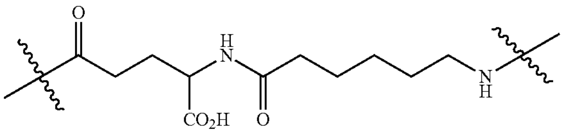 IsoGlu-Ahx |
| L11 | 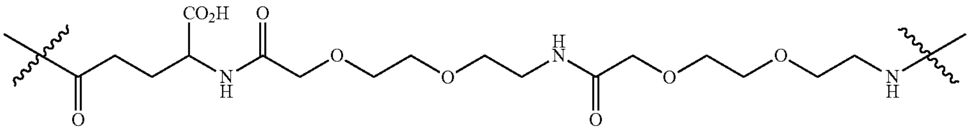 IsoGlu-OEG-OEG |

TABLE 5-continued

| Illustrative Linker Moieties | |
|---|---|
| # | Linker Moiety |
| L12 | 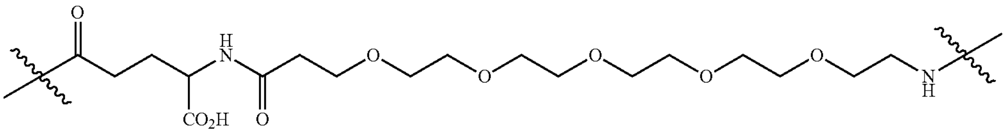 IsoGlu-PEG5 |
| L13 | 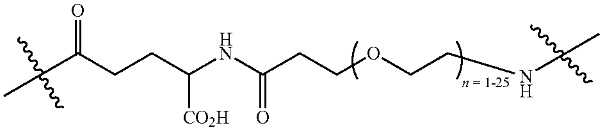 IsoGlu-PEGn |
| L14 | 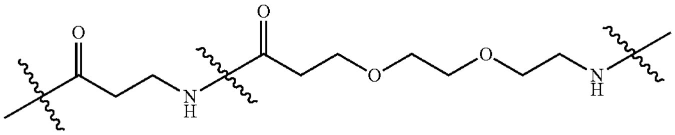 βAla-PEG2 |
| L15 | 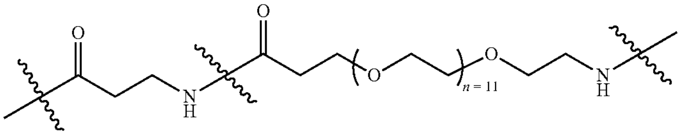 βAla-PEG11 (40 atoms) |

In particular embodiments, a peptide inhibitor of the present invention comprises any of the linker moieties shown in Table 5 and any of the half-life extension moieties shown in Table 4, including any of the following combinations shown in Table 6a:

TABLE 6a

Illustrative Combinations of Linkers and Half-Life Extension Moieties in Peptide Inhibitors

| Linker | Half-Life Extension Moiety | Linker | Half-Life Extension Moiety | Linker | Half-Life Extension Moiety |
|---|---|---|---|---|---|
| L1 | C1 | L1 | C2 | L1 | C3 |
| L2 | C1 | L2 | C2 | L2 | C3 |
| L3 | C1 | L3 | C2 | L3 | C3 |
| L4 | C1 | L4 | C2 | L4 | C3 |
| L5 | C1 | L5 | C2 | L5 | C3 |
| L6 | C1 | L6 | C2 | L6 | C3 |
| L7 | C1 | L7 | C2 | L7 | C3 |
| L8 | C1 | L8 | C2 | L8 | C3 |
| L9 | C1 | L9 | C2 | L9 | C3 |
| L10 | C1 | L10 | C2 | L10 | C3 |
| L11 | C1 | L11 | C2 | L11 | C3 |
| L12 | C1 | L12 | C2 | L12 | C3 |
| L13 | C1 | L13 | C2 | L13 | C3 |
| L14 | C1 | L14 | C2 | L14 | C3 |
| L15 | C1 | L15 | C2 | L15 | C3 |
| L1 | C4 | L1 | C5 | L1 | C6 |
| L2 | C4 | L2 | C5 | L2 | C6 |
| L3 | C4 | L3 | C5 | L3 | C6 |
| L4 | C4 | L4 | C5 | L4 | C6 |
| L5 | C4 | L5 | C5 | L5 | C6 |

TABLE 6a-continued

Illustrative Combinations of Linkers and Half-Life Extension Moieties in Peptide Inhibitors

| Linker | Half-Life Extension Moiety | Linker | Half-Life Extension Moiety | Linker | Half-Life Extension Moiety |
|---|---|---|---|---|---|
| L6 | C4 | L6 | C5 | L6 | C6 |
| L7 | C4 | L7 | C5 | L7 | C6 |
| L8 | C4 | L8 | C5 | L8 | C6 |
| L9 | C4 | L9 | C5 | L9 | C6 |
| L10 | C4 | L10 | C5 | L10 | C6 |
| L11 | C4 | L11 | C4 | L11 | C6 |
| L12 | C4 | L12 | C5 | L12 | C6 |
| L13 | C4 | L13 | C5 | L13 | C6 |
| L14 | C4 | L14 | C5 | L14 | C6 |
| L15 | C4 | L15 | C5 | L15 | C6 |
| L1 | C7 | L1 | C8 | L1 | C9 |
| L2 | C7 | L2 | C8 | L2 | C9 |
| L3 | C7 | L3 | C8 | L3 | C9 |
| L4 | C7 | L4 | C8 | L4 | C9 |
| L5 | C7 | L5 | C8 | L5 | C9 |
| L6 | C7 | L6 | C8 | L6 | C9 |
| L7 | C7 | L7 | C8 | L7 | C9 |
| L8 | C7 | L8 | C8 | L8 | C9 |
| L9 | C7 | L9 | C8 | L9 | C9 |
| L10 | C7 | L10 | C8 | L10 | C9 |
| L11 | C7 | L11 | C8 | L11 | C9 |
| L12 | C7 | L12 | C8 | L12 | C9 |
| L13 | C7 | L13 | C8 | L13 | C9 |
| L14 | C7 | L14 | C8 | L14 | C9 |
| L15 | C7 | L15 | C8 | L15 | C9 |
| L1 | C10 | L1 | C11 | L1 | C12 |
| L2 | C10 | L2 | C11 | L2 | C12 |

TABLE 6a-continued

Illustrative Combinations of Linkers and Half-Life Extension Moieties in Peptide Inhibitors

| Linker | Half-Life Extension Moiety | Linker | Half-Life Extension Moiety | Linker | Half-Life Extension Moiety |
|---|---|---|---|---|---|
| L3 | C10 | L3 | C11 | L3 | C12 |
| L4 | C10 | L4 | C11 | L4 | C12 |
| L5 | C10 | L5 | C11 | L5 | C12 |
| L6 | C10 | L6 | C11 | L6 | C12 |
| L7 | C10 | L7 | C11 | L7 | C12 |
| L8 | C10 | L8 | C11 | L8 | C12 |
| L9 | C10 | L9 | C11 | L9 | C12 |
| L10 | C10 | L10 | C11 | L10 | C12 |
| L11 | C10 | L11 | C11 | L11 | C12 |
| L12 | C10 | L12 | C11 | L12 | C12 |
| L13 | C10 | L13 | C11 | L13 | C12 |
| L14 | C10 | L14 | C11 | L14 | C12 |
| L15 | C10 | L15 | C11 | L15 | C12 |
| L1 | C13 | L1 | C14 | L1 | C15 |
| L2 | C13 | L2 | C14 | L2 | C15 |
| L3 | C13 | L3 | C14 | L3 | C15 |
| L4 | C13 | L4 | C14 | L4 | C15 |
| L5 | C13 | L5 | C14 | L5 | C15 |
| L6 | C13 | L6 | C14 | L6 | C15 |
| L7 | C13 | L7 | C14 | L7 | C15 |
| L8 | C13 | L8 | C14 | L8 | C15 |
| L9 | C13 | L9 | C14 | L9 | C15 |
| L10 | C13 | L10 | C14 | L10 | C15 |
| L11 | C13 | L11 | C14 | L11 | C15 |
| L12 | C13 | L12 | C14 | L12 | C15 |
| L13 | C13 | L13 | C14 | L13 | C15 |
| L14 | C13 | L14 | C14 | L14 | C15 |
| L15 | C13 | L15 | C14 | L15 | C15 |
| L1 | C16 | L1 | C17 | L1 | C18 |
| L2 | C16 | L2 | C17 | L2 | C18 |
| L3 | C16 | L3 | C17 | L3 | C18 |
| L4 | C16 | L4 | C17 | L4 | C18 |
| L5 | C16 | L5 | C17 | L5 | C18 |
| L6 | C16 | L6 | C17 | L6 | C18 |
| L7 | C16 | L7 | C17 | L7 | C18 |
| L8 | C16 | L8 | C17 | L8 | C18 |
| L9 | C16 | L9 | C17 | L9 | C18 |
| L10 | C16 | L10 | C17 | L10 | C18 |
| L11 | C16 | L11 | C17 | L11 | C18 |
| L12 | C16 | L12 | C17 | L12 | C18 |
| L13 | C16 | L13 | C17 | L13 | C18 |
| L14 | C16 | L14 | C17 | L14 | C18 |
| L15 | C16 | L15 | C17 | L15 | C18 |

In some embodiments, any of the amino acids present in a peptide inhibitor described herein, except for X5, X34, B1 and B6, is replaced by a Lysine, and the free amino acid of this Lysine is conjugated to a half-life extension moiety using a linker, e.g., any of the linkers shown in Table 5, any of the half-life extension moieties shown in Table 4, and/or any of the combinations shown in Table 6b.

In some embodiments, there may be multiple linkers present between the peptide the conjugated moiety, e.g., half-life extension moiety, e.g., as depicted in Table 6b.

TABLE 6b

Illustrative Combinations of Linkers and Half-Life Extension Moieties in Peptide Inhibitors

| Linker | Half-Life Extension Moiety |
|---|---|
| L1-L2 | C10 |
| L2-L5-L3 | C10 |
| L3-L8 | C10 |
| L1-L2-L3 | C10 |
| L5-L3-L3-L3 | C10 |
| L1-L2 | C8 |
| L2-L5-L3 | C8 |
| L3-L8 | C8 |
| L1-L2-L3 | C8 |
| L5-L3-L3-L3 | C8 |
| L1-L2 | PEG (e.g., C13, C14, C15, C16, C17 or C18) |
| L2-L5-L3 | PEG (e.g., C13, C14, C15, C16, C17 or C18) |
| L3-L8 | PEG (C13, C14, C15, C16, C17 or C18) |
| L1-L2-L3 | PEG (C13, C14, C15, C16, C17 or C18) |
| L5-L3-L3-L3 | PEG (C13, C14, C15, C16, C17 or C18) |

In certain embodiments, the half-life of a peptide inhibitor of the invention that includes a conjugated chemical substituent, i.e., a half-life extension moiety, is at least 100%, at least 120%, at least 150%, at least 200%, at least 250%, at least 300%, at least 400%, or at least 500% of the half-life of the same peptide inhibitor but without the conjugated chemical substituent. In certain embodiments, the lipophilic substituents and/or polypermic moieties enhance the permeability of the peptide inhibitor through the epithelium and/or its retention in the lamina propria. In certain embodiments, the permeability through the epithelium and/or the retention in the lamina propria of a peptide inhibitor of the invention that includes a conjugated chemical substituent is at 100%, at least 120%, at least 150%, at least 200%, at least 250%, at least 300%, at least 400%, or at least 500% of the half-life of the same peptide inhibitor but without the conjugated chemical substituent.

As discussed, in certain embodiments, the peptide inhibitors of the present invention may be modified, e.g., to enhance stability, increase permeability, or enhance drug like characteristics, through conjugation of a chemical moiety, e.g., a half-life extension moiety, to one or more amino acid side chain within the peptide. For example, the N(epsilon) of lysine N(epsilon), the β-carboxyl of aspartic, or the γ-carboxyl of glutamic acid may be appropriately functionalized. Thus, to produce the modified peptide, an amino acid within the peptide may be appropriately modified. Further, in some instances, the side chain is acylated with an acylating organic compound selected from the group consisting of: Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid glutaric acid or bile acids. One having skill is the art will appreciate that a series of conjugates can be linked, e.g., for example PEG4, isoglu and combinations thereof.

In certain embodiments, pharmaceutical compositions and formulations of the present invention comprise a compound as described herein and one or more permeation or absorption enhancer. Examples of absorption enhancers may include bile salts, fatty acids, surfactants (anionic, cationic, and nonanionic) chelators, Zonular OT, esters, cyclodextrin, dextran sulfate, azone, crown ethers, EDTA, sucrose esters, and phosphotidyl choline, for example. Although absorption enhancers are not typically carriers by themselves, they are also widely associated with other carriers to improve oral bioavailability by transporting of peptides and proteins across the intestinal mucosa. Such substances can be added to the formulation as excipients or incorporated to form non-specific interactions with the intended peptide inhibitor.

Dietary components and/or other naturally occurring substances affirmed as enhancing tight junction permeation and as Generally Recognized As Safe (GRAS) include, e.g., asglycerides, acylcamitines, bile salts, and medium chain fatty acids. Sodium salts of medium chain fatty acids (MCFAS) were also suggested to be permeation enhancers. The most extensively studied MCFAS is sodium caprate, a salt of capric acid, which comprises 2-3% of the fatty acids in the milk fat fraction. To date, sodium caprate is mainly used as an excipient in a suppository formulation (Doktacillin™) for improving rectal ampicillin absorption. The permeation properties of another dietary MCFAS, sodium caprylate (8-carbon), were shown in vitro to be lower when compared to sodium caprate. Sodium caprylate and a peptidic drug were formulated in an admixture with other excipients in oil to generate an oily suspension (OS) that enhanced permeability (Tuvia, S. et al., Pharmaceutical Research, Vol. 31, No. 8, pp. 2010-2021 (2014): incorporated herein by reference in its entirety).

For example, in one embodiment, a permeation enhancer is combined with a compound as described herein and, wherein the permeation enhancer comprises at least one of a medium-chain fatty acid, a long-chain fatty acid, a bile salt, an amphiphilic surfactant, and a chelating agent. In certain embodiments, medium-chain fatty acid salts promote absorption by increasing paracellular permeability of the intestinal epithelium. In one embodiment, a permeation enhancer comprising sodium N-[hydroxybenzoyl)amino] caprylate is used to form a weak noncovalent association with the peptide inhibitor of the instant invention, wherein the permeation enhancer favors membrane transport and further dissociation once reaching the blood circulation. In another embodiment, a peptide inhibitor of the present invention is conjugated to oligoarginine, thereby increasing cellular penetration of the peptide into various cell types. Further, in at least one embodiment a noncovalent bond is provided between a peptide inhibitor of the present invention and a permeation enhancer selected from the group consisting of a cyclodextrin (CD) and a dendrimers, wherein the permeation enhancer reduces peptide aggregation and increasing stability and solubility for the peptide inhibitor molecule.

In certain embodiments, a pharmaceutical composition or formulation comprises a peptide inhibitor of the present invention and a transient permeability enhancer (TPEs). Permeation enhancers and TPEs may be used to increase orally bioavailability or the peptide inhibitor. One example of a TPE that may be used is an oily suspension formulation that disperses a powder containing sodium caprylate and a therapeutic agent (Tuvia, S. et al., Pharmaceutical Research, Vol. 31, No. 8, pp. 2010-2021 (2014) incorporated herein by reference in its entirety).

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two step process. As used herein, for a single oxidation step, the trityl protecting group is often employed during assembly, allowing deprotection during cleavage, followed by solution oxidation. When a second disulfide bond is required, one has the option of native or selective oxidation. For selective oxidation requiring orthogonal protecting groups, Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation, the trityl protecting group is used for all cysteines, allowing for natural folding of the peptide.

A skilled worker will be well aware of suitable techniques which can be used to perform the oxidation step.

Illustrative Peptide Inhibitors

Illustrative peptide inhibitors of the present invention are shown in Table 2. Table 2 provides the amino acid sequence of selected peptide inhibitors, and also indicates that these peptide inhibitors included an N-terminal Ac and a C-terminal $NH_2$ group. The peptide inhibitors include a disulfide bond between the Cys residues at X5 and X34. In other embodiments, the present invention includes peptides having the same sequence and conjugated chemical moiety (if present) but with a C-terminal OH group. According to the protocols discussed herein, a number of the peptide inhibitors shown in Table 2 were synthesized. Table 2 provides the IC50 values for selected monomer peptide inhibitors and peptide dimer inhibitors in inhibiting IL-23 binding to the IL-23R, or in inhibiting IL-23 signaling as determined by measuring changes in phospho-STAT3 levels, as described in the accompanying Examples.

In certain embodiments, peptide inhibitors of the present invention comprise an amino acid sequence shown in Tables 2 or 3, e.g., an amino acid sequence comprising X1-X33 or X1-X34. In some embodiments, the peptide inhibitors comprise a natural N-terminal $NH_2$ and/or a natural C-terminal COOH, while in other embodiments, they comprise a different chemical group or moiety at their N- and/or C-termini. In some embodiments, the N-terminus is Hy or Ac. In certain embodiments, the C-terminus is $NH_2$.

The present invention thus provides various peptide inhibitors which bind or associate with IL-23, to disrupt or block binding between IL-23 and IL-23R.

The peptide inhibitors of the present invention may be synthesized by many techniques that are known to those skilled in the art. In certain embodiments, monomer subunits are synthesized, purified, and dimerized using the techniques described in the accompanying Examples. In certain embodiments, the peptide inhibitors are produced synthetically, e.g., as described in Example 1. For peptides comprising a thioether bond, in one embodiment, the unpurified linear peptide may be dissolved in 50:50 ACN:water (2.5 mg/ml) then diluted to about 1 mg/mL in 0.1M Tris-HCl pH8.5 buffer and thioether bond formation monitored using LCMS.

In certain embodiments, the peptide inhibitors are produced recombinantly in a cell comprising an expression vector comprising a polynucleotide sequence encoding the peptide inhibitors.

In related embodiments, the present invention includes polynucleotides that encode any of the peptide sequences present in any of the peptide inhibitors described herein, including those having a sequence set forth in Formula Ia or Formula Ib, any of the consensus sequences described herein, or as shown in Table 2.

In addition, the present invention includes vectors, e.g., expression vectors, comprising a polynucleotide of the present invention. The invention also includes cells comprising an expression vector described herein, e.g., 293T cells or HEK cells.

Methods of Treatment

In certain embodiments, the present invention includes methods of inhibiting IL-23 binding to an IL-23R on a cell, comprising contacting the IL-23 with a peptide inhibitor of the present invention. In certain embodiments, the cell is a mammalian cell. In particular embodiments, the method is performed in vitro or in vivo. Inhibition of binding may be determined by a variety of routine experimental methods and assays known in the art.

In certain embodiments, the present invention includes methods of inhibiting IL-23 signaling by a cell, comprising contacting the IL-23 with a peptide inhibitor of the present invention. In certain embodiments, the cell is a mammalian cell. In particular embodiments, the method is performed in vitro or in vivo. In particular embodiments, the inhibition of IL-23 signalling may be determined by measuring changes in phospho-STAT3 levels in the cell.

In some embodiments, the present invention provides methods for treating a subject afflicted with a condition or indication associated with IL-23 or IL-23R (e.g., activation of the IL-23/IL-23R signaling pathway), wherein the method comprises administering to the subject a peptide inhibitor or pharmaceutical composition of the present invention. In one embodiment, a method is provided for treating a subject afflicted with a condition or indication characterized by inappropriate, deregulated, or increased IL-23 or IL-23R activity or signaling, comprising administering to the individual a peptide inhibitor or pharmaceutical composition of the present invention in an amount sufficient to inhibit (partially or fully) binding of IL-23 to IL-23R in the subject. In particular embodiments, the inhibition of IL-23 binding to IL-23R occurs in particular organs or tissues of the subject, e.g., the stomach, small intestine, large intestine, colon, or intestinal mucosa.

In some embodiments, methods of the present invention comprise treating a subject in need thereof by providing an effective amount of a peptide inhibitor or pharmaceutical composition of the present invention to a subject in need thereof. In particular embodiments, the subject in need thereof has been diagnosed with or has been determined to be at risk of developing a disease or disorder associated with IL-23/IL-23R. In particular embodiments, the subject is a mammal, e.g., a human. In related embodiments, the present invention provides a method of treating or preventing a disease or disorder in a subject in need thereof, comprising providing to the subject an effective amount of a peptide inhibitor or pharmaceutical composition of the present invention to a subject in need thereof In certain embodiments of methods described herein, the condition, indication, disease or disorder is autoimmune inflammation and related diseases and disorders, such as multiple sclerosis, asthma, rheumatoid arthritis, inflammatory bowel diseases (IBDs), juvenile IBD, adolescent IBD, Crohn's disease, sarcoidosis, Systemic Lupus Erythematosus, ankylosing spondylitis (axial spondyloarthritis), psoriatic arthritis, or psoriasis. In particular embodiments, the disease or disorder is psoriasis (e.g., plaque psoriasis, guttate psoriasis, inverse psoriasis, pustular psoriasis, Palmo-Plantar Pustulosis, psoriasis vulgaris, or erythrodermic psoriasis), atopic dermatitis, acne ectopica, ulcerative colitis, Crohn's disease, Celiac disease (nontropical Sprue), enteropathy associated with seronegative arthropathies, microscopic colitis, collagenous colitis, eosinophilic gastroenteritis/esophagitis, colitis associated with radio- or chemotherapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, Wiskott-Aldrich Syndrome, pouchitis resulting after proctocolectomy and ileoanal anastomosis, gastrointestinal cancer, pancreatitis, insulin-dependent diabetes mellitus, mastitis, cholecystitis, cholangitis, primary biliary cirrhosis, viral-associated enteropathy, pericholangitis, chronic bronchitis, chronic sinusitis, asthma, uveitis, or graft versus host disease.

In one aspect, the present invention provides a peptide inhibitor having a half-life of at least several hours to one day in vitro or in vivo (e.g., when administered to a human subject) sufficient for daily (q.d.) or twice daily (b.i.d.) dosing of a therapeutically effective amount. In another embodiment, the peptide inhibitor has a half-life of three days or longer sufficient for weekly (q.w.) dosing of a therapeutically effective amount. Further, in another embodiment, the peptide inhibitor has a half-life of eight days or longer sufficient for bi-weekly (b.i.w.) or monthly dosing of a therapeutically effective amount. In another embodiment, the peptide inhibitor is derivatized or modified such that is has a longer half-life as compared to the underivatized or unmodified peptide inhibitor. In another embodiment, the peptide inhibitor contains one or more chemical modifications to increase serum half-life.

In some embodiments, methods of the present invention comprise providing a peptide inhibitor of the present invention (i.e., a first therapeutic agent) to a subject in need thereof in combination with a second therapeutic agent. In certain embodiments, the second therapeutic agent is provided to the subject before and/or simultaneously or together with and/or after the pharmaceutical composition is administered to the subject. In particular embodiments, the second therapeutic agent is an anti-inflammatory agent. In certain embodiments, the second therapeutic agent is a non-steroidal anti-inflammatory drug, steroid, or immune modulating agent. In another embodiment, the method comprises administering to the subject a third therapeutic agent. In particular embodiments, the third therapeutic agent is an anti-inflammatory agent, e.g., a non-steroidal anti-inflammatory drug, steroid, or immune modulating agent.

In particular embodiments, the peptide inhibitor, or the pharmaceutical composition comprising a peptide inhibitor, is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. One embodiment of a biodegradable matrix is a matrix of one of either polylactide, polyglycolide, or polylactide co-glycolide (copolymers of lactic acid and glycolic acid).

In certain embodiments, the present invention includes pharmaceutical compositions comprising one or more peptide inhibitors of the present invention and a pharmaceutically acceptable carrier, diluent or excipient. A pharmaceutically acceptable carrier, diluent or excipient refers to a non-toxic solid, semi-solid or liquid filler, diluent, encapsulating material or formulation auxiliary of any type. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

In certain embodiments, the compositions are administered orally, parenterally, intracistemally, intravaginally, intraperitoneally, intrarectally, topically (e.g., as by powders, ointments, drops, suppository, or transdermal patch), by inhalation (such as intranasal spray), ocularly (such as intraocularly) or buccally. The term "parenteral" as used herein refers to modes of administration, which include intravenous, intramuscular, intraperitoneal, intrasternal, subcutaneous, intradermal and intraarticular injection and infusion. Accordingly, in certain embodiments, the compositions are formulated for delivery by any of these routes of administration.

In certain embodiments, pharmaceutical compositions for parenteral injection comprise pharmaceutically acceptable sterile aqueous or nonaqueous solutions, dispersions, suspensions or emulsions, or sterile powders, for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain adjuvants such as preservative, wetting agents, emulsifying agents, and dispersing agents. Prolonged absorption of an injectable pharmaceutical form may be brought about by the inclusion of agents which delay absorption, such as aluminum monostearate and gelatin.

Injectable depot forms include those made by forming microencapsule matrices of the peptide inhibitor in one or more biodegradable polymers such as polylactide-polyglycolide, poly(orthoesters), poly(anhydrides), and (poly)glycols, such as PEG. Depending upon the ratio of peptide to polymer and the nature of the particular polymer employed, the rate of release of the peptide inhibitor can be controlled. Depot injectable formulations are also prepared by entrapping the peptide inhibitor in liposomes or microemulsions compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes, e.g., administration to the skin or mucosa, including surfaces of the lung and eye. Compositions for topical lung administration, including those for inhalation and intranasal, may involve solutions and suspensions in aqueous and non-aqueous formulations and can be prepared as a dry powder which may be pressurized or non-pressurized. In non-pressurized powder compositions, the active ingredient may be finely divided form may be used in admixture with a larger-sized pharmaceutically acceptable inert carrier comprising particles having a size, for example, of up to 100 micrometers in diameter. Suitable inert carriers include sugars such as lactose.

Alternatively, the composition may be pressurized and contain a compressed gas, such as nitrogen or a liquefied gas propellant. The liquefied propellant medium and indeed the total composition may be such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A peptide inhibitor of the invention may be delivered in a pharmaceutically acceptable ophthalmic vehicle, such that the peptide inhibitor is maintained in contact with the ocular surface for a sufficient time period to allow the peptide inhibitor to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the peptide inhibitors of the invention may be injected directly into the vitreous and aqueous humour.

Compositions for rectal or vaginal administration include suppositories which may be prepared by mixing the peptide inhibitors of this invention with suitable non-irritating excipients or carriers such as cocoa butter, polyethylene glycol or a suppository wax, which are solid at room temperature but liquid at body temperature and, therefore, melt in the rectum or vaginal cavity and release the active compound.

Peptide inhibitors of the present invention may also be administered in liposomes or other lipid-based carriers. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a peptide inhibitor of the present invention, stabilizers, preservatives, excipients, and the like. In certain embodiments, the lipids comprise phospholipids, including the phosphatidyl cholines (lecithins) and serines, both natural and synthetic. Methods to form liposomes are known in the art.

Pharmaceutical compositions to be used in the invention suitable for parenteral administration may comprise sterile aqueous solutions and/or suspensions of the peptide inhibitors made isotonic with the blood of the recipient, generally using sodium chloride, glycerin, glucose, mannitol, sorbitol, and the like.

In some aspects, the invention provides a pharmaceutical composition for oral delivery. Compositions and peptide inhibitors of the instant invention may be prepared for oral administration according to any of the methods, techniques, and/or delivery vehicles described herein. Further, one having skill in the art will appreciate that the peptide inhibitors of the instant invention may be modified or integrated into a system or delivery vehicle that is not disclosed herein, yet is well known in the art and compatible for use in oral delivery of peptides.

In certain embodiments, formulations for oral administration may comprise adjuvants (e.g. resorcinols and/or nonionic surfactants such as polyoxyethylene oleyl ether and n-hexadecylpolyethylene ether) to artificially increase the permeability of the intestinal walls, and/or enzymatic inhibitors (e.g. pancreatic trypsin inhibitors, diisopropylfluorophosphate (DFF) or trasylol) to inhibit enzymatic degradation. In certain embodiments, the peptide inhibitor of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents. pH adjusting agents, sweetening agents, flavoring agents or perfuming agents.

In particular embodiments, oral dosage forms or unit doses compatible for use with the peptide inhibitors of the present invention may include a mixture of peptide inhibitor and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of peptide inhibitor, wherein the dosage form comprises at least one of a pill, a tablet, a capsule, a gel, a paste, a drink, a syrup, ointment, and suppository. In some instances, an oral dosage form is provided that is designed and configured to achieve delayed release of the peptide inhibitor in the subject's small intestine and/or colon.

In one embodiment, an oral pharmaceutical composition comprising a peptide inhibitor of the present invention comprises an enteric coating that is designed to delay release of the peptide inhibitor in the small intestine. In at least some embodiments, a pharmaceutical composition is provided which comprises a peptide inhibitor of the present invention and a protease inhibitor, such as aprotinin, in a delayed release pharmaceutical formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition comprising a peptide inhibitor of the present invention is provided in an enteric coating, the enteric coating being designed to protect and release the pharmaceutical composition in a controlled manner within the subject's lower gastrointestinal system, and to avoid systemic side effects. In addition to enteric coatings, the peptide inhibitors of the instant invention may be encapsulated, coated, engaged or otherwise associated within any compatible oral drug delivery system or component. For example, in some embodiments a peptide inhibitor of the present invention is provided in a lipid carrier system comprising at least one of polymeric hydrogels, nanoparticles, microspheres, micelles, and other lipid systems.

To overcome peptide degradation in the small intestine, some embodiments of the present invention comprise a hydrogel polymer carrier system in which a peptide inhibitor of the present invention is contained, whereby the hydrogel polymer protects the peptide inhibitor from proteolysis in the small intestine and/or colon. The peptide inhibitors of the present invention may further be formulated for compatible use with a carrier system that is designed to increase the dissolution kinetics and enhance intestinal absorption of the peptide. These methods include the use of liposomes, micelles and nanoparticles to increase GI tract permeation of peptides.

Various bioresponsive systems may also be combined with one or more peptide inhibitor of the present invention to provide a pharmaceutical agent for oral delivery. In some embodiments, a peptide inhibitor of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a peptide inhibitor disclosed herein, wherein the surface of the peptide inhibitor surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the peptide inhibitor.

Other embodiments comprise a method for oral delivery of a peptide inhibitor of the present invention, wherein the peptide inhibitor is provided to a subject in combination with permeation enhancers that promote the transport of the peptides across the intestinal mucosa by increasing paracellular or transcellular permeation. For example, in one embodiment, a permeation enhancer is combined with a peptide inhibitor, wherein the permeation enhancer comprises at least one of a long-chain fatty acid, a bile salt, an amphiphilic surfactant, and a chelating agent. In one embodiment, a permeation enhancer comprising sodium N-[hydroxybenzoyl)amino] caprylate is used to form a weak noncovalent association with the peptide inhibitor of the instant invention, wherein the permeation enhancer favors membrane transport and further dissociation once reaching the blood circulation. In another embodiment, a peptide inhibitor of the present invention is conjugated to oligoarginine, thereby increasing cellular penetration of the peptide into various cell types. Further, in at least one embodiment a noncovalent bond is provided between a peptide inhibitor of the present invention and a permeation enhancer selected from the group consisting of a cyclodextrin (CD) and a dendrimers, wherein the permeation enhancer reduces peptide aggregation and increasing stability and solubility for the peptide inhibitor molecule.

When used in at least one of the treatments or delivery systems described herein, a peptide inhibitor of the present invention may be employed in pure form or, where such forms exist, in pharmaceutically acceptable salt form.

The total daily usage of the peptide inhibitors and compositions of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific peptide inhibitor employed; e) the duration of the treatment; f) drugs used in combination or coincidental with the specific peptide inhibitor employed, and like factors well known in the medical arts.

In particular embodiments, the total daily dose of the peptide inhibitors of the invention to be administered to a human or other mammal host in single or divided doses may be in amounts, for example, from 0.0001 to 300 mg/kg body weight daily or 1 to 300 mg/kg body weight daily.

Non-Invasive Detection of Intestinal Inflammation

The peptide inhibitors of the invention may be used for detection, assessment and diagnosis of intestinal inflammation by microPET imaging, wherein the peptide inhibitor is labeled with a chelating group or a detectable label, as part of a non-invasive diagnostic procedure. In one embodiment, a peptide inhibitor is conjugated with a bifunctional chelator. In another embodiment, a peptide inhibitor is radiolabeled. The labeled peptide inhibitor is then administered to a subject orally or rectally. In one embodiment, the labeled peptide inhibitor is included in drinking water. Following uptake of the peptide inhibitor, microPET imaging may be used to visualize inflammation throughout the subject's bowels and digestive track.

EXAMPLES

Example 1

Synthesis of Peptides

Peptides were synthesized using the Merrifield solid phase synthesis techniques on a 12 channel multiplex Symphony® peptide synthesizer (Protein Technologies, Inc.) and were assembled using O-Benzotriazole-N,N,N',N'-tetramethyluroniumhexafluorophosphate (HBTU) and N,N-diisopropylethylamine (DIPEA) coupling conditions. Rink Amide MBHA resin was used for peptides with C-terminal amides and pre-loaded Wang Resin with N-α-Fmoc protected amino acids was used for peptides with C-terminal acids. The coupling reagents (HBTU and DIPEA premixed) and amino acid solutions were prepared in dimethylformamide (DMF) at a concentration of 100 mM. The peptides were assembled using standard Symphony® protocols. Pre-loaded Wang resin (250 mg, 0.14 mmol, 0.56 mmol/g loading, 100-200 mesh) or MBHA resin (250 mg, 0.15 mmol, 0.6 mmol/g loading, 100-200 mesh) was placed in each reaction vial and washed twice with 4 mL of DMF followed by 2×10 min treatments with 2.5 mL of 20% 4-methylpiperidine/DMF (conditions for Fmoc deprotection). Either the Wang resin or the Rink Amide MBHA resin was then washed three times with DMF (4 mL), followed by addition of 2.5 mL of amino acid and 2.5 mL of a HBTU-DIPEA mixture. After 45 min of reaction with frequent agitation, the resin was filtered and washed three times with DMF (4 mL). This process was then repeated.

The coupling reaction was carried out twice for the first 25 amino acids and three times for the remaining amino acids. The assembled peptide on resin was then cleaved using a 2 h treatment with cocktail reagent K[54]. The cleaved peptides were precipitated in cold (0° C.) diethyl ether, followed by washing two times with diethyl ether and air drying. The crude peptides were then submitted to an oxidation reaction in order to form the disulfide bridge. The crude peptide was dissolved in 50% acetonitrile/water at a concentration of 0.5 mg/mL. A saturated solution of iodine in methanol was added dropwise until a yellow color persisted. Excess iodine was quenched by the addition of solid ascorbic acid until the solution became colorless. The resulting solution was purified by preparative reverse-phase HPLC: Phenomenex® Luna C18 column (10 μm, 300 Å, 250×21.2 mm) using buffer A (0.1% trifluoracetic acid (TFA) in water), buffer B (0.1% TFA in acetonitrile) gradient 33%0-55% buffer B over 45 min, flow rate 20 mL/min, detection at 220 nm. Fractions containing the desired product were pooled and lyophilized to give a white solid.

Example 2

Characterization of Peptide Inhibition of Binding of Interleukin-23 to the Interleukin-23 Receptor Certain peptides were tested to identify peptides that inhibit the binding of IL-23 to human IL-23R or mouse IL-23R, and inhibit IL-23/IL-23R functional activity, as described below. The sequences of the peptides tested are shown in Table 2. Each of these peptides comprised a disulfide bond between X5 and X34, except for Peptide 1, which comprises a disulfide bond between X4 and X33.

IL23-IL23R Competitive Binding ELISA

Immulon® 4HBX plate was coated with 200 ng/well of IL23R_huFC and incubated overnight at 4° C. The wells were washed three times with PBST, blocked with PBS containing 5% PhosphoBLOCKER (Cell Biolabs #AKR-103) for 1 hour at room temperature, and washed again three times with PBST. Serial dilutions of test peptides and IL-23 at a final concentration of 0.9 nM diluted in PBS were added to each well and incubated for 2 hours at room temperature. After the wells were washed, bound IL-23 was detected by incubation with 50 ng/well of goat anti-p40 polyclonal antibodies (R&D Systems #AF309) diluted in PBS for 1 hour at room temperature. The wells were again washed four times with PBST. The secondary antibodies, HRP conjugated donkey anti-goat IgG (Jackson ImmunoResearch Laboratories #705-035-147) diluted 1:5000 in PBS, was then added and incubated for 30 minutes at room temperature. The plate was finally washed as above. Signals were visualized with TMB One Component HRP Membrane Substrate, quenched with 2 M sulfuric acid and read spectrophotometrically at 450 nm. IC50 values determined from these data are shown in Table 2. * indicates >10.000-100,000;  indicates >1,000-10,000; * indicates ≤1,000.

TABLE 2

Peptide Inhibitor IC50 Values for Inhibition of IL-23/IL-23R Binding

| Peptide No. (SEQ ID NO) | | X1 | X2 | X3 | X4 | X5 | X6 | X7 | X8 | X9 | X10 | X11 | X12 | X13 | X14 | X15 | X16 | X17 | X18 |
|---|---|---|---|---|---|---|---|---|---|---|---|---|---|---|---|---|---|---|---|
| 1 | Ac- | Y | M | Q | C | I | R | R | L | I | E | A | A | L | D | P | N | L | N |
| 2 | Ac- | F | N | M | V | C | Q | D | R | F | Y | T | A | A | A | W | P | N | L |
| 3 | Ac- | F | N | M | F | C | Q | R | L | F | Y | W | A | A | A | N | P | N | L |
| 4 | Ac- | F | N | M | V | C | Q | R | G | F | Y | V | A | A | A | D | P | N | L |
| 5 | Ac- | F | N | M | I | C | Q | E | G | F | Y | P | A | A | A | W | P | N | L |
| 6 | Ac- | F | N | M | S | C | Q | I | R | F | Y | L | A | A | A | D | P | N | L |
| 7 | Ac- | F | N | M | L | C | Q | I | R | F | Y | I | A | A | A | L | P | N | L |
| 8 | Ac- | F | N | M | Q | C | L | R | R | M | V | E | A | G | I | D | P | N | L |
| 9 | Ac- | F | N | M | F | C | Q | L | A | F | Y | S | A | A | A | D | P | N | L |
| 10 | Ac- | F | N | M | Q | C | L | R | R | M | S | E | A | G | V | D | P | N | L |
| 11 | Ac- | F | N | M | Q | C | A | R | R | M | S | E | A | G | V | D | P | N | L |
| 12 | Ac- | F | N | M | Q | C | L | R | R | A | S | E | A | G | V | D | P | N | L |
| 13 | Ac- | F | N | M | Q | C | L | R | R | M | A | E | A | G | V | D | P | N | L |
| 14 | Ac- | F | N | M | Q | C | L | R | R | M | S | E | A | A | V | D | P | N | L |
| 15 | Ac- | F | N | M | Q | C | L | R | R | M | S | E | A | G | A | D | P | N | L |
| 16 | Ac- | F | N | M | Q | C | L | R | R | M | S | E | A | G | V | D | A | N | L |
| 17 | Ac- | F | N | M | Q | C | L | R | R | M | S | E | A | G | V | D | P | N | L |
| 18 | Ac- | F | N | M | Q | C | L | R | R | M | S | E | A | G | V | D | P | N | L |
| 19 | Ac- | F | N | M | Q | C | L | R | R | M | S | E | A | G | V | D | P | N | L |
| 20 | Ac- | F | N | M | Q | C | L | R | R | M | S | E | A | G | V | D | P | N | L |
| 21 | Ac- | F | N | M | Q | C | L | R | R | M | S | E | A | G | V | D | P | N | L |
| 22 | Ac- | F | N | M | Q | C | L | R | R | M | S | E | A | G | V | D | P | N | L |

| Peptide No. (SEQ ID NO) | X19 | X20 | X21 | X22 | X23 | X24 | X25 | X26 | X27 | X28 | X29 | X30 | X31 | X32 | X33 | X34 | | IC50 IL23R_ huFC (uM) |
|---|---|---|---|---|---|---|---|---|---|---|---|---|---|---|---|---|---|---|
| 1 | L | E | Q | R | P | A | K | I | P | S | I | T | D | D | C | NH2 | | >100,000 |
| 2 | N | E | E | F | R | N | A | F | I | L | S | L | R | D | F | C | NH2 | >100,000 |
| 3 | N | E | E | D | R | N | A | R | I | L | S | F | R | D | G | C | NH2 | * |
| 4 | N | E | E | F | R | N | A | L | I | L | S | L | R | D | F | C | NH2 | >100,000 |
| 5 | N | E | E | F | R | N | A | F | I | L | S | L | R | D | F | C | NH2 | >100,000 |
| 6 | N | E | E | E | R | N | A | L | I | K | S | L | R | D | M | C | NH2 | >100,000 |
| 7 | N | E | E | N | R | N | A | N | I | K | S | I | R | D | R | C | NH2 | >100,000 |
| 8 | N | S | G | Q | R | W | A | K | I | R | S | I | F | D | D | C | NH2 | * |
| 9 | N | E | E | Q | R | N | A | K | I | K | S | F | R | D | L | C | NH2 | * |
| 10 | N | Q | E | Q | R | W | A | K | I | K | S | I | M | D | D | C | NH2 | ** |
| 11 | N | Q | E | Q | R | W | A | K | I | K | S | I | M | D | D | C | NH2 | >100,000 |
| 12 | N | Q | E | Q | R | W | A | K | I | K | S | I | M | D | D | C | NH2 | ** |
| 13 | N | Q | E | Q | R | W | A | K | I | K | S | I | M | D | D | C | NH2 | *** |
| 14 | N | Q | E | Q | R | W | A | K | I | K | S | I | M | D | D | C | NH2 | >100,000 |
| 15 | N | Q | E | Q | R | W | A | K | I | K | S | I | M | D | D | C | NH2 | >100,000 |
| 16 | N | Q | E | Q | R | W | A | K | I | K | S | I | M | D | D | C | NH2 | ** |
| 17 | A | Q | E | Q | R | W | A | K | I | K | S | I | M | D | D | C | NH2 | ** |
| 18 | N | A | E | Q | R | W | A | K | I | K | S | I | M | D | D | C | NH2 | >100,000 |
| 19 | N | Q | E | Q | A | W | A | K | I | K | S | I | M | D | D | C | NH2 | ** |
| 20 | N | Q | E | Q | R | A | A | K | I | K | S | I | M | D | D | C | NH2 | ** |
| 21 | N | Q | E | Q | R | W | A | K | A | K | S | I | M | D | D | C | NH2 | ** |
| 22 | N | Q | E | Q | R | W | A | K | I | A | S | I | M | D | D | C | NH2 | ** |

The ability of Peptide 10 to block binding of IL-23 to IL-12Rβ1 or binding of IL-12 to IL-12Rβ1 was also determined. Human IL-12Rβ1 ELISA assays were performed as follows: an assay plate was coated with 100 ng/well of human IL-12Rβ1_huFC and incubated overnight at 4° C. The wells were washed, blocked, and washed again. Serial dilutions of test peptides and either IL-23 or IL-12 at a fixed concentration corresponding to EC50 values were added to each well, and incubated for 2 hours at room temperature. After the wells were washed, bound IL-23 were detected with goat anti-p40 polyclonal antibodies followed by an HRP conjugated donkey anti-goat IgG, and bound IL-12 were detected with a biotin conjugated anti-p40 monoclonal antibody followed by HRP conjugated streptavidin. Signals were visualized with TMB One Component HRP Membrane Substrate and quenched with 2 M sulfuric acid.

Binding of Peptide 10 was selective, because it did not block binding of IL-23 to IL-12Rβ1 or binding of IL-12 to IL12Rβ1. Ustekinumab, which binds to the p40 subunit of IL-23, blocked binding of IL-23 to IL-12Rβ1, but not binding of IL-23 to IL-23R, as shown in Table 3. These results show that the binding properties of Peptide 10 and Ustekinumab are distinct, and suggest that Peptide 10 may be binding to the p19 subunit of IL-23 or some other site on IL-23 specific for IL-23R binding. Additionally, Peptide 10 did not block binding of IL-6 or IL-13 to IL-6R or IL-13Ra1, respectively (data not shown). Peptide 10 also blocked binding of mouse IL-23 to mouse IL-23R (data not shown), which indicates it can be used in an IL-23-dependent mouse efficacy assay.

TABLE 3

| Competition binding properties of Peptide 10 and Ustekinumab | | | | | |
|---|---|---|---|---|---|
| | Human IL23/IL23R huFc ELISA | Mouse IL23/IL23R huFc ELISA | Human IL23/IL12Rβ1 huFc ELISA | Human IL12/IL12Rβ1huFc ELISA | Mouse splenocyte assay |
| Peptide 10 | 3.3 uM | 3.6 uM | >100 uM | >100 uM | 1.6 uM |
| Ustekinumab | >100 ug/ml | | 0.14 ug/ml | | 0.06 ug/ml |

Mouse Splenocyte Assay

Frozen mouse splenocytes (Hooke Lab), suspended in RPMI Medium 1640 (Life technologies #22400-089) supplemented with 10% heat inactivated FBS (Life technologies #16140-071), 1×MEM Non-Essential Amino Acid Solution (Life technologies #11140-050), 1 mM sodium pyruvate (Life technologies #11360-070), 100 units of Penicillin-Streptomycin (Life technologies #15140-122, 0.05 mM 2-mercaptoethanol (Life technologies #21985-023) and recombinant human IL-2 (R&D Systems #202-IL-010/CF), were seeded at 4×10E5 cells/well in a 96 well tissue culture plate. Serial dilutions of test peptides and IL-23 at a final concentration of 20 ng/mL were preincubated in a separate assay plate for 60 minutes at 37° C. in a 5% $CO_2$ humidified incubator. Preincubated samples were then added to the culture plate containing splenocytes and incubated for an additional 67 hours at 37° C. in a 5% $CO_2$ humidified incubator. A sandwich ELISA kit for mouse IL17A (Biolegend #436204) was used to measure the amount of IL-17A in each sample supernatants, according to manufacturer's instructions. For Peptide 10, the IC50 was 1.6 uM. This assay indicates that Peptide 10 is active in inhibiting human IL-23-dependent release of IL-17 from mouse splenocytes.

All of the above U.S. patents, U.S. patent application publications, U.S. patent applications, foreign patents, foreign patent applications and non-patent publications referred to in this specification, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A monomer peptide inhibitor of an interleukin-23 comprising the amino acid sequence set forth in any one of SEQ ID NOs: 3, 8-10, 12, 13, 16, 17, and 19-22, wherein the peptide inhibitor comprises a disulfide bond between the two Cys amino acids of the peptide inhibitor, or a pharmaceutically acceptable salt thereof.

2. A polynucleotide comprising a sequence encoding the peptide inhibitor of claim 1.

3. A vector comprising the polynucleotide of claim 2.

4. A pharmaceutical composition comprising the peptide inhibitor or pharmaceutically acceptable salt thereof of claim 1.

5. The pharmaceutical composition of claim 4, further comprising an enteric coating.

6. The pharmaceutical composition of claim 5, wherein the enteric coating protects and releases the pharmaceutical composition within a subject's lower gastrointestinal system.

* * * * *